(12) United States Patent
Babu et al.

(10) Patent No.: US 6,410,594 B1
(45) Date of Patent: *Jun. 25, 2002

(54) SUBSTITUTED CYCLOPENTANE COMPOUNDS USEFUL AS NEURAMINIDASE INHIBITORS

(75) Inventors: Yarlagadda S. Babu; Pooran Chand; John A. Montgomery, all of Birmingham, AL (US)

(73) Assignee: Biocryst Pharmaceuticals, Inc., Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/202,351

(22) PCT Filed: Jun. 13, 1997

(86) PCT No.: PCT/US97/09309

§ 371 (c)(1),
(2), (4) Date: Jun. 9, 1999

(87) PCT Pub. No.: WO97/47194

PCT Pub. Date: Dec. 18, 1997

Related U.S. Application Data

(60) Provisional application No. 60/019,930, filed on Jun. 14, 1996, and provisional application No. 60/044,010, filed on May 2, 1997.

(51) Int. Cl.$^7$ .............................................. A61K 31/235
(52) U.S. Cl. ........................ 514/563; 514/613; 514/635; 562/504; 564/32; 564/193
(58) Field of Search ................. 514/563, 613, 514/635; 562/504; 564/32, 193

(56) References Cited

U.S. PATENT DOCUMENTS

| | | | |
|---|---|---|---|
| 4,426,391 A | 1/1984 | Alexander et al. | |
| 5,362,728 A | 11/1994 | Asberom et al. | 514/217 |
| 5,453,533 A | 9/1995 | Luo et al. | 560/142 |
| 5,602,277 A | 2/1997 | Babu et al. | 562/439 |
| 5,739,160 A | 4/1998 | Mittendorf et al. | 514/510 |
| 5,789,434 A | 8/1998 | Kluender et al. | 514/414 |

FOREIGN PATENT DOCUMENTS

| | | |
|---|---|---|
| EP | 0 130 119 A2 | 1/1985 |
| EP | 0 743 320 A2 | 11/1996 |
| JP | 49-185 | 1/1974 |
| JP | 59-163365 | 9/1984 |
| JP | 63-179835 | 7/1988 |
| JP | 05065255 | 3/1993 |
| WO | WO92/16541 | 10/1992 |
| WO | WO 98/34935 | 8/1998 |
| WO | WO 99/33781 | 7/1999 |
| WO | WO 99/54290 | 10/1999 |
| WO | WO 99/54299 | 10/1999 |

OTHER PUBLICATIONS

Rao et al, Synthesis of oxa– and thia–analogs of bicyclo [n.3.0] alkanes, Indian J. Chem., Sect. B (1987), 26B(10, 939–46, abstract.

Sakurai et al, Synthetic study of HIV–1 protease inhibitors, Pept. Chem. (1993), 31st, 185–8, abstract.

Allan et al, Synthesis of Analogues of GABA, XV Preparation and Resolution of Some Potent Cyclopentene and Cyclopentane Derivatives, Aust. J. Chem., 1986, 39, 855–864.

Collect. Czech. Chem. Commun. vol. 58 (1993) pp. 2159–2179.

Kogyo Kagaku Zashi vol. 60, No. 3 (1957) pp. 355–356.

Journal of Medical Chemistry, vol. 21, No. 3, pp. 245–248.

Tetrahedron vol. 51, No. 37, pp. 10259–10280 (1995).

Chem. Pharm. Bull. 38(12) pp. 3242–3248 (1990).

Chemical Abstracts. vol. 65 10460 c. (1966).

Chemical Abstracts. vol. 62 9031 d–e (1965).

Chemical Abstracts. vol. 65 15301 c (1966).

Bergmeier et al., "Chirospecific Synthesis of (1S, 3R)–1–Amino–3–(hydroxymethyl)cyclopentane, a Precursor for Carbocyclic Nucleoside Synthesis. Intramolecular Aziridine Cyclizations", J. Org. Chem., 1993, No. 58, pps. 5019–5022.

Mohamed–Chérif Boucemma et al, "Magnetic Resonance Studies of the Structure and the Red Photolysis Reactions of 2–Chloro–2–Nitrosonobornane", J. Chem. Soc, Perkin Trans. 2 (1995), pp. 1381–1387.*

Toshihiro Yamamoto et al, "Syntheses of Sialic Acid Isomers with Inhibitory Activity Against Neuraminidase", Tet. Lett., vol. 33 (1992), pp 5791–5794.*

* cited by examiner

Primary Examiner—Gary Geist
Assistant Examiner—Robert W. Deemie
(74) Attorney, Agent, or Firm—Connolly Bove Lodge & Hutz LLP

(57) ABSTRACT

Compounds represented by formula (I), and pharmaceutically acceptacle salts thereof; and their method of preparation are provided. Compounds of the above formula are influenza virus neuraminidase inhibitors and can be used in treating patients infected with influenza virus.

(I)

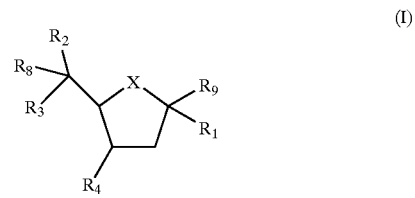

31 Claims, No Drawings

SUBSTITUTED CYCLOPENTANE COMPOUNDS USEFUL AS NEURAMINIDASE INHIBITORS

DESCRIPTION

This application claim benefit to provisional application 60/019,930 Jun. 14, 1996 and this application claim benefit to provisional application 60/044,010, May 2, 1997.

TECHNICAL FIELD

This invention relates to novel substituted cyclopentane compounds and derivatives thereof useful as neuraminidase inhibitors, to pharmaceutical compositions containing said compounds useful for the prevention, treatment or amelioration of viral, bacterial and other infections, and to methods of using said compounds. The present invention is also concerned with novel intermediates or precursors for producing the novel substituted cyclopentane compounds of the present invention.

BACKGROUND OF THE INVENTION

Despite the wealth of information available, influenza remains a potentially devastating disease of man, lower mammals, and birds. No effective vaccine exists and no cure is available once the infection has been initiated.

Influenza viruses consist of eight pieces of single stranded RNA, packaged in orderly fashion within the virion. Each piece codes for one of the major viral proteins. The replication complex is enclosed with a membrane composed of matrix protein associated with a lipid bilayer. Embedded in the lipid bilayer are two surface glycoprotein spikes, hemagglutinin (HA) and the enzyme neuraminidase (NA). All of the viral genes have been cloned and the three-dimensional structures of the surface glycoproteins have been determined.

Influenza viruses continually undergo antigenic variation in the two surface antigens, HA and NA, toward which neutralizing antibodies are directed. For this reason, vaccines and a subject's natural immune system have not been very effective. Attention is now being directed to finding other potential antiviral agents act ing at other sites of the virion. This invention is directed to novel compounds which are useful in inhibiting the viral surface enzyme NA.

Furthermore, many other organisms carry NA. Many of these NA-possessing organisms are also major pathogens of man and/or mammals, including *Vibraeo cholerae, Clostridium perfringes, Streptococcus pneumonia, Arthrobacter sialophilas*, and other viruses, such as parainfluenza virus, mumps virus, Newcastle disease virus, fowl plague virus, and Sendai virus. Compounds of this invention are also directed to inhibiting NA of these organisms.

In viruses, NA exists as a tetramer made of four roughly spherical subunits and a centrally-attached stalk containing a hydrophobic region by which it is embedded in the organism's membrane. Several roles have been suggested for NA. The enzyme catalyzes cleavage of the α-ketosidic linkage between terminal sialic acid and an adjacent sugar residue. Removal of the sialic acid lowers the viscosity and permits access of the virus to the epithelial cells. NA also destroys the HA receptor on the host cell, thus allowing elution of progeny virus particles from infected cells.

Research indicates that the active site for influenza neuraminidase remains substantially unchanged for the major strains of influenza. For example, a comparison of sequences from influenza A subtypes and influenza B shows conserved residues with crucial structural and functional roles. Even though the sequence homology is only about 30%, many of the catalytic residues are conserved. Furthermore, the three-dimensional structures of influenza A and B neuraminidases have been determined. Superposition of the various structures shows remarkable structural similarity of the active site. Since the active site amino acid residues are conserved in all known influenza A neuraminidases that have been sequenced so far, an inhibitor that is effective against different strains of influenza A and/or B neuraminidase can be designed based on the three-dimensional structure of a neuraminidase.

In general, the role of NA is thought to be for the mobility of the virus both to and from the site of infections. Compounds that inhibit neuraminidase's activity may protect a subject from infection and/or cure a subject once infection has set in. It is a further object of this invention to provide a method of using compounds of this invention for treating and/or curing a viral infection.

Analogs of neuraminic acid, such as 2-deoxy-2,3-didehydro-N-acetylneuraminic acid (DANA) and its derivatives are known to inhibit HA in vitro; however, these compounds are inactive in vivo. Palese and Schulman, in CHEMOPROPHYLAXIS AND VIRUS INFECTION OF THE UPPER RESPIRATORY TRACT, Vol. 1 (J. S. Oxford, Ed.), CRC Press, 1977, at PS 189–205.

Von Itzstein et al. (PCT Publication WO 91/16320) describes cyclohexane analogs of α-D-neuraminic acid of the formula

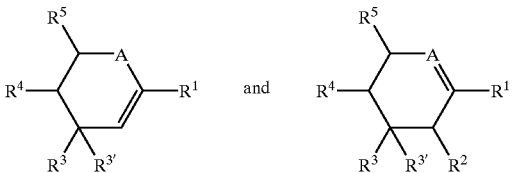

wherein:
A is O, C or S in Formula (a), and N or C in Formula (b);
$R^1$ is $CO_2H$, $PO_3H_2$, $NO_2$, $SO_2H$, $SO_3H$, tetrazolyl-, $CH_2CHO$, CHO, or $CH(CHO)_2$;
$R^2$ is H, $OR^6$, F, Cl, Br, CN, $NHR^6$, $SR^6$ or $CH_2X$, where X is $NHR^6$ halogen, or $OR^6$;
$R^3$ and $R^{3'}$ are H, CN, $NHR^6$, $SR^6$, $=NOR^6$, $OR^6$, guanidino, $NR^6$;
$R^4$ is $NHR^6$, $SR^6$, $OR^6$, $CO_2R^6$, $NO_2$, $C(R^6)_3$, $CH_2CO_2R^6$, $CH_2NO_2$ or $CH_2NHR^6$;
$R^5$ is $CH_2YR^6$, $CHYR^6CH_2YR^6$ or $CHYR^6CHYR^6CH_2YR^6$;
$R^6$ is H, acyl, alkyl, allyl, or aryl;
Y is O, S, NH, or H;
and parmaceutical salts thereof, useful as antiviral agents In addition, certain benzene derivatives are suggested in U.S. Pat. No. 5,453,533 as being inhibitors of influenza virus neuraminidase and various others are disclosed in U.S. patent application Ser. No. 08/413,886. Yamamoto et al. describe various sialic acid isomers as having inhibitory activity against neuraminidase in *Synthesis of Sialic Acid Isomers With Inhibitory Activity Against Neuraminidase*, TETRAHEDRON LETTERS, Vol. 33, No. 39, pp. 5791–5794, 1992.

WO 96/26933 to Gilead Sciences, Inc. describes certain 6-membered ring compounds as possible inhibitors of neuraminidase.

However, none of these references disclose the cyclopentane derivatives of the present invention.

SUMMARY OF INVENTION

An aspect of the present invention is directed to compounds represented by the formula:

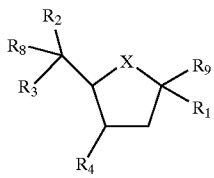

wherein

X is $CH_2$, O or S;

$R_1$ is H, OH, $NH_2$, or $OR_{11}$;

$R_9$ is $CO_2H$, $SO_3H$, $PO_3H_2$, $NO_2$, esters thereof, or salts thereof;

$R_2$ is H,

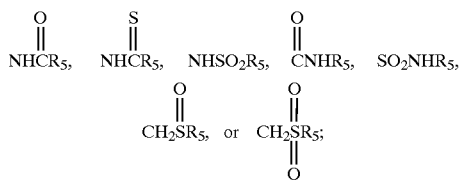

each of $R_3$ and $R_8$ individually is H, $(CH_2)_nCO_2R_{10}$, $(CH_2)_mOR_{10}$, $CON(R_{10})_m$, $(CH_2)_nN(R_{10})_m$, $CH(R_{10})_m$, $(CH_2)_n(R_{10})_m$, $CH_2CH(OR_{10})CH_2OR_{10}$, $CH(OR_{10})CH(OR_{10})CH_2OR_{10}$, $CH_2OR_{10}$, $CH(OR_{10})CH_2NHR_{10}$, $CH_2CH(OR_{10})CH_2NHR_{10}$, $CH(OR_{10})CH(OR_{10})CH_2NHR_{10}$, or $NR_{10}C(=NR_{10})N(R_{10})_m$; provided that at least one of $R_2$, $R_3$ and $R_8$ is other than H;

$R_4$ is H, $(CH_2)_nOH$, $(CH_2)_nNH_2$, $(CH_2)_nC(=NH)NH_2$, $(CH_2)_nNHC(=NR_7)NH_2$, $(CH_2)_nCN$ or $(CH_2)_nN_3$;

$R_5$ is H, lower alkyl, branched chain alkyl, cyclic alkyl or $CF_3$;

$R_7$ is H, OH, CN, $NH_2$ or $NO_2$;

each $R_{10}$ individually is H, lower alkyl, lower alkylene, branched alkyl, cyclic alkyl, substituted cyclic alkyl, $(CH_2)_n$ aromatic, $(CH_2)_n$-substituted aromatic, and when m is 2 both $R_{10}$ groups can also be interconnected to form an N-heterocyclic ring;

$R_{11}$ is lower alkyl, branched alkyl, or $(CH_2)_m$ aromatic;

m is 1 or 2; and n is 0–4; and further provided that when X is O or S, $R_3$ and $R_8$ is other than $CH(OR_{10})CH(OR_{10})CH_2OR_{10}$;

and phramaceutically acceptable salts thereof.

The present invention is also concerned with compositions for inhibiting influenza virus neuraminidase comprising a pharmaceutically acceptable carrier and an amount effective for inhibiting influenza virus neuraminidase of a compound as defined above.

A further aspect of the present invention involves a method for inhibiting influenza virus that comprises administering to a patient in need thereof a compound as defined above in an amount effective for inhibiting influenza virus neuraminidase.

A still further aspect of the present invention is concerned with treating influenza virus infection comprising administering to a patient in need thereof a compound as defined above in an amount effective for inhibiting influenza virus neuraminidase.

The present invention is also concerned with methods for producing the compounds defined above.

Best and Various Modes for Carrying Out Invention

An aspect of the present invention is directed to compounds represented by the formula:

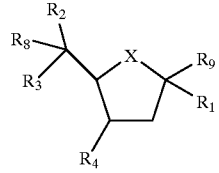

wherein

X is $CH_2$, O or S;

$R_1$ is H, OH, $NH_2$, or $OR_{11}$;

$R_9$ is $CO_2H$, $SO_3H$, $PO_3H_2$, $NO_2$, esters thereof, or salts thereof;

$R_2$ is H,

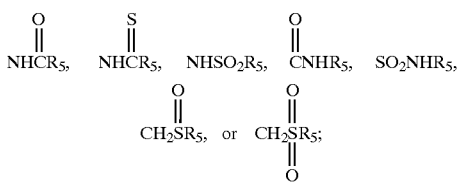

each of $R_3$ and $R_8$ individually is H, $(CH_2)_nCO_2R_{10}$, $(CH_2)_mOR_{10}$, $CON(R_{10})_m$, $(CH_2)_nN(R_{10})_m$, $CH(R_{10})_m$, $CH_2)_n(R_{10})_m$, $CH_2CH(OR_{10})CH_2OR_{10}$, $CH(OR_{10})CH(OR_{10})CH_2OR_{10}$, $CH_2OR_{10}$, $CH(OR_{10})CH_2NHR_{10}$, $CH_2CH(OR_{10})CH_2NHR_{10}$, $CH(OR_{10})CH(OR_{10})CH_2NHR_{10}$, or $NR_{10}C(=NR_{10})N(R_{10})_m$;

provided that at least one of $R_2$, $R_3$ and $R_8$ is other than H;

$R_4$ is H, $(CH_2)_nOH$, $(CH_2)_nNH_2$, $(CH_2)_nC(=NH)NH_2$, $(CH_2)_nNHC(=NR_7)NH_2$, $(CH_2)_nCN$ or $(CH_2)_nN_3$;

$R_5$ is H, lower alkyl, branched chain alkyl, cyclic alkyl or $CF_3$;

$R_7$ is H, OH, CN, $NH_2$ or $NO_2$;

each $R_{10}$ individually is H, lower alkyl, lower alkylene, $(CH_2)_n$ aromatic, branched alkyl, cyclic alkyl, substituted cyclic alkyl, $(CH_2)_n$-substituted aromatic, and when m is 2 both $R_{10}$ groups can also be interconnected to form an N-heterocyclic ring;

$R_{11}$ is lower alkyl, branched alkyl, or $(CH_2)_m$ aromatic;

m is 1 or 2; and n is 0–4; and further provided that when X is O or S, $R_3$ and $R_8$ is other than $CH(OR_{10})CH(OR_{10})CH_2OR_{10}$;

and pharmaceutically acceptable salts thereof.

Concerning $R_{10}$ when m=2, each $R_{10}$ can be the same or different.

The lower alkyl groups contain 1 to about 8 carbon, and preferably 1 to about 3 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. Examples of suitable cyclic aliphatic groups typically contain 3–8 carbon atoms and include cyclopentyl and cyclohexyl. The aromatic or aryl groups are preferably phenyl or alkyl substituted aromatic groups (aralkyl) such as phenyl $C_{1-3}$ alkyl such as benzyl.

Examples of substituted cycloalkyl groups include cyclic aliphatic groups typically containing 3–8 carbon atoms in the ring substituted with alkyl groups typically having 1–6 carbon atoms and/or hydroxy group. Usually 1 or 2 substituted groups are present.

The lower alkylene group can be straight, branched chain or cyclic unsaturated hydrocarbon group and contains 2–8 carbon atoms and preferably 2–3 carbon atoms. Examples of alkylene groups are vinyl, 1-propenyl, allyl, isopropenyl, 2-methyl-2-propenyl and cyclopentenyl.

The N-heterocyclic rings contain 3–7 atoms in the ring. The heterocyclic rings can be substituted such as with a lower alkyl group. Examples of suitable heterocyclic groups are pyrrolidino, azetidino, piperidino, 3,4-didehydropiperidino, 2-methylpiperidino and 2-ethylpiperidino.

Pharmaceutically acceptable salts of the compounds of formula (I) include those derived from pharmaceutically acceptable, inorganic and organic acids and bases. Examples of suitable acids include hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic, trifluoroacetic and benzenesulphonic acids.

Salts derived from appropriate bases include alkali such as sodium and ammonia.

Examples of some specific compounds within the scope of the present invention are:

cis-3-[(methylcarbonylamino)methyl] cyclopentanecarboxylic acid;

trans-3-amino-c-$^4$-(methylcarbonylamino)methyl-r-cyclopentanecarboxylic acid;

trans-3-{[(amino)(imino)methyl]amino}-c-4-[(methylcarbonylamino)methyl]cyclopentan-r-carboxylic acid;

4(3-{[(amino)(imino)methyl]amino}-3α-[(2-hydroxy-1-methylcarbonyl-amino)ethyl]-1-cyclopentanecarboxylic acid;

sodium 3β-{[amino)(imino)methyl]amino}-4α-[(2-hydroxy)(1-methylcarbonylamino)ethyl]cyclopentan-r-carboxylate;

trans-3-amino-trans-1-hydroxy-cis-4[(hydroxymethyl)(methylcarbonylamino)methyl]cyclopentan-r-carboxylic acid;

trans-3-{[(amino)(imino)methyl]amino}-trans-1-hydroxy-cis-4-[(2-hydroxymethyl)(1-methylcarbonylamino)ethyl] cyclopentan-r-carboxylic acid;

3β-amino-4α-[(1-methylcarbonylamino)(2,3,4-trihydroxy) butyl]cyclopentancarboxylic acid;

3β-{[(amino)(imino)methyl)amino}-4α-[(1-methylcarbonylamino)(2,3,4-trihydroxy)butyl]-cyclopentancarboxylic acid;

cis-3-{[(amino)(imino)methyl]amino)-trans-1-hydroxy-trans-4-[(1-methylcarbonylamino)(2-trifluoromethyl-carbonyloxy)ethyl]cyclopentan-r-carboxylic acid;

t-3-amino-c-4-[(1-methylcarbonylamino)(2-phenylmethoxy)ethyl]-t-1-hydroxycyclopentan-r-carboxylic acid;

c-3-{[(amino(imino)methyl]amino}-t-1-hydroxy-t-4-{(methylcarbonylamino)([(methyl)-(methoxy)amino] carbonyl}methyl}cyclopentan-r-carboxylic acid;

3β-{[(amino)(imino)methyl]amino}-4α-{{4-[(methoxy) (methyl)amino]1-(methylcarbonylamino-2-oxo}butyl}cyclopentancarboxylic acid;

t-3-{[(amino)(imino)methyl]amino}-c-4-[(diethylaminocarbonyl)(methylcarbonylamino)methyl]-t-1-hydroxycyclopentan-r-carboxylic acid;

t-3-amino-c-4-[(di-n-propylaminocarbonyl) (methylcarbonylamino)methyl]-t-1-hydroxy-cyclopentan-r-carboxylic acid;

t-3-{[(amino)(imino)methyl]amino}-c-4-[di-n-propylaminocarbonyl)(methylcarbonylamino)methyl]-t-hydroxycyclopentan-r-carboxylic acid;

c-3-{[(amino)(imino)methyl]amino}-t-4-[(di-n-propylaminocarbonyl)(methylcarbonylamino)methyl]-t-1-hydroxycyclopentan-r-carboxylic acid;

3β-{[(amino)(imino)methyl]amino}-4α-[(di-n-propylaminocarbonyl)(methylcarbonylamino)-methyl) cyclopentancarboxylic acid;

3β-{[(amino)(imino)methyl]amino}-4α-[(methylcarbonylamino)(3-pentylaminocarbonyl)methyl] cyclopentancarboxylic acid;

3β-{[Amino)(imino)methyl]amino}-4α-[(diethylaminocarbonyl)(methylcarbonylamino)methyl] cyclopentancarboxylic acid;

3β-{1[(Amino)(imino)methyl]amino}-4α-{[(ethyl)(propyl) aminocarbonyl](methyl-carbonylamino) methyl}cyclopentancarboxylic acid;

3β-{([(Amino)(imino)methyl]amino}-4α-{[(ethyl)(propyl) aminocarbonyl](methyl-carbonylamino) methyl}cyclopentancarboxylic acid;

3β-{[(Amino)(imino)methyl]amino}-4α-[1-(1-methylcarbonylamino)pent-2-enyl] cyclopentancarboxylic acid;

3β-{[(Amino)(imino)methyl]amino}-4α-[1-(-methylcarbonylamino)pentyl]cyclopentancarboxylic acid.

In addition, an exemplary key intermediate, methyl 3-t-butoxycarbonylamino-4-formylcyclopentanecarboxylate 6 (Scheme 4), may be synthesized from methyl 3-hydroxy-4-hydroxymethylcyclopentanecarboxylate 1 (synthesis given in the attached sheets). The primary hydroxyl of 1 may be protected with the TBDMS (tert-butyldimethylsilyl) group; secondary hydroxyl groups upon Mitsunobu reaction ($Ph_3P$, DEAD (diethyl azodi carboxylate), $N_3H$) can give the azido 3; azido 3 is reduced ($H_2$, Pd/C in presence of $((t-boc)_2O)$) to give protected amine 4; primary hydroxyl may be deprotected and on oxidation may give the key intermediate aldehyde 6.

As shown in Scheme 5, the aldehyde 6 may be further coupled with an appropriate allyl or vinyl tributyl tin compound to introduce the moiety for the glycol or glycerol side chain. The scheme has been elaborated with vinyl tributyl tin. The t-boc group in compound 7 may be removed (trifluoroacetic acid) to an amine 8 and the amine may be reacted with bis boc (—OC(=O)C($CH_3)_3$) thiourea to give the protected guanidine 9. The hydroxyl of 9 upon Mitsunobu reaction can give azide 10; the azide can be reduced to amine 11, and further acylated with an appropriate alkyl acid or alkyl sulfonyl chloride to give the desired 12. The double bond of an allyl or vinyl group in the side chain on osmium catalysed dihydroxylation could give compound 13, which upon further deprotections could yield the desired target 14.

Before the deprotection stage in compound 13, the primary hydroxyl may be converted to a tosyl (4—$CH_3$ phenyl $SO_2$) group, conversion of a tosyl to an azide and an azide to an amine give the compounds where $R_3$=CH(OH) $CH_2NH_2$, CH(OH)CH(OH)$CH_2NH_2$, or $CH_2$CH(OH) $CH_2NH_2$.

The synthetic route to prepare the compounds, when $R_7$ is OH, CN, $NH_2$ or $NO_2$ is shown in Scheme 6. The amine 8 upon reaction with cyanogen bromide could give the cyanamine 15; the side chain may be manipulated in the same manner as shown in Scheme 5 to give 16; the further reaction of cyanamine 16 with hydroxylamine hydrochloride, hydrazine or cyanamide could give the appropriate 17, which on deprotection may yield the targets 18.

The reaction of 8 with 2-methyl-1-nitro-2-thiopseudourea leads to 18 ($R_7$=$NO_2$). When $R_2$ is

the compounds of the type 12 on reaction with $P_2S_5$ or Lawsson's reagent (2,4-bis(4-methoxy phenyl)-1,3-dithia-2,4-diphosphetane-2,4-disulfide) could give compound 19, which on further reactions may be converted to the desired targets.

Other methods to prepare the equivalent of key intermediate 5 are presented in Schemes 8 and 9. The intermediate 25 may be prepared by two different procedures:

i) Scheme 8

The reaction of dimethylmalonate with sodium hydride and then cis 1,4-dichloro-2-butene gives 1,1-dimethyl-3-cyclopentene dicarboxylate 20, which is saponified, decarboxylated and esterified to give the benzyl ester of 3-cyclopentene 22. Compound 22 upon reaction with PhI=NTS give aziridine 23. The aziridine may be opened with bisphenylthiomethane and n-butyllithium to give 24, and 24 upon reaction with copper oxide and copper chloride could yield 25. Compound 25 may be used in Scheme 5 and elaborated in the same manner as 5 to give the desired targets.

ii) Scheme 9

The cyclopentene ester 22 upon an hydroxyamination reaction with chloramine-T in the presence of $OsO_4$ gives 26; the isomers are separated. The desired isomer upon reaction with 4-nitrobenzenesulfonyl chloride gives 27, and the ONS group may be displaced with bisphenylthiomethane to give 24. Conversion to 25 occurs as described above.

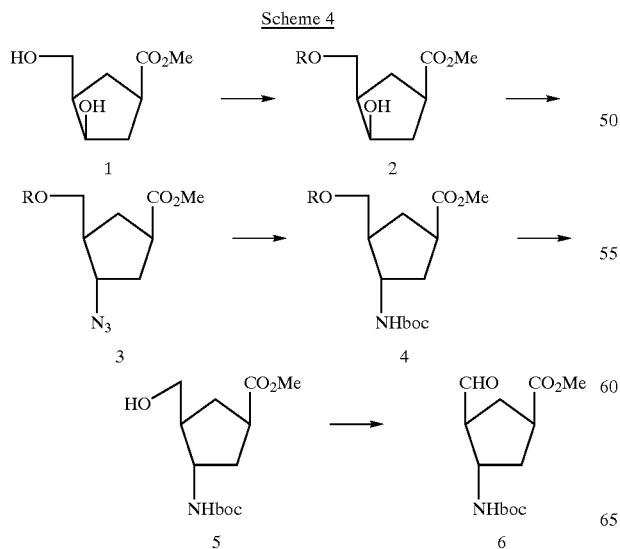

Scheme 4

-continued

R is benzyl, lower alkyl, acetyl, benzyl carbonyl, or lower alkyl carbonyl.

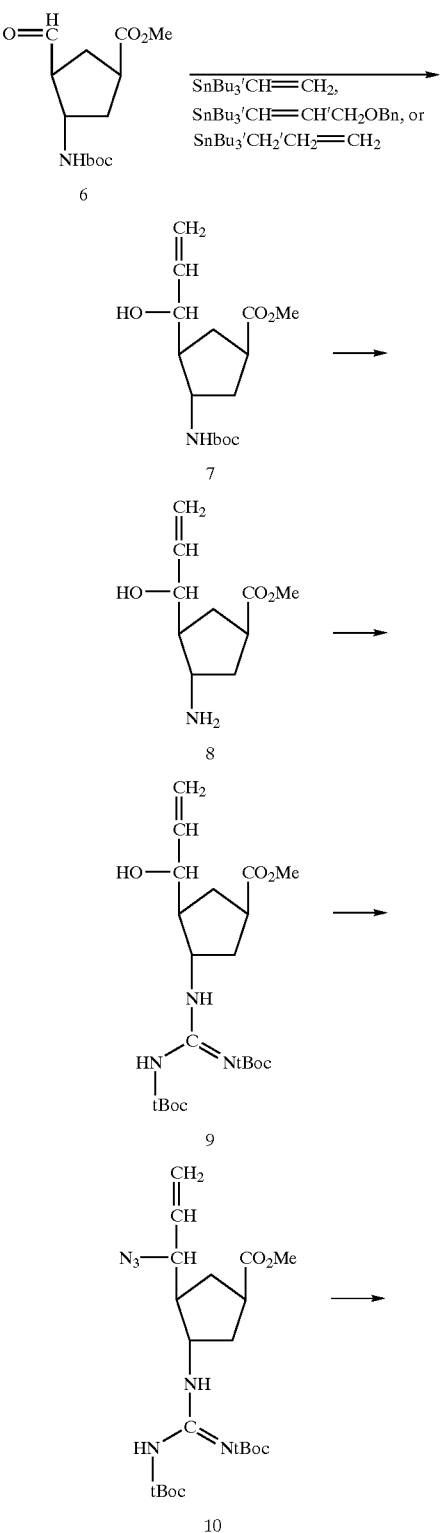

Scheme 5

-continued
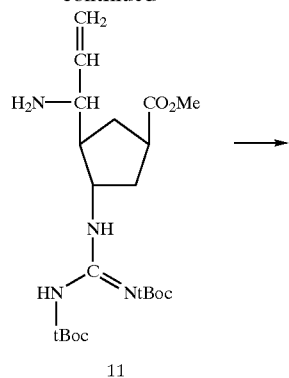
11
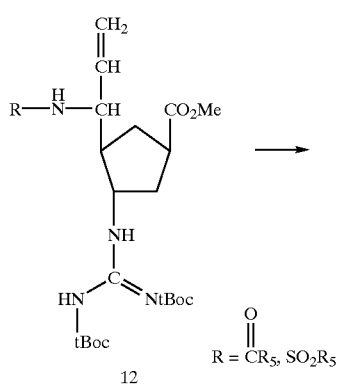
R = CR₅, SO₂R₅
12
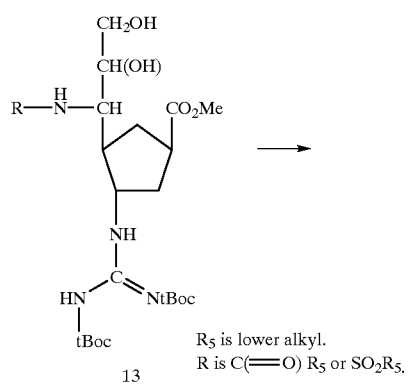
R₅ is lower alkyl.
R is C(=O)R₅ or SO₂R₅.
13
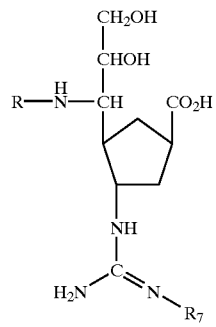
14
Scheme 6
When R₇ is OH, CN, NH₂, or NO₂
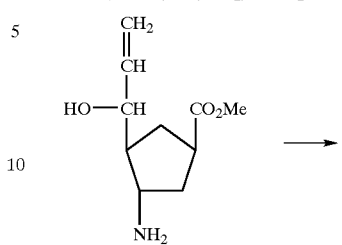
8
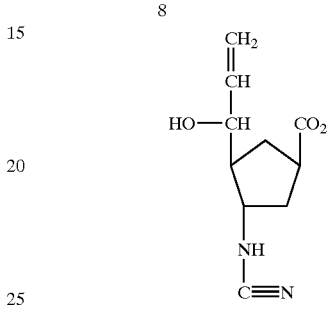
15
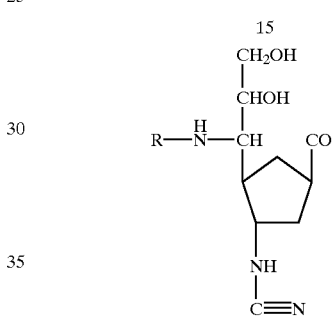
16
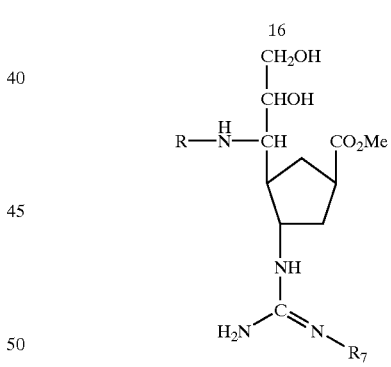
17
NH₂OH, NH₂NH₂, or NH₂CN
18

-continued
R is lower akyl, lower alkyl carbonyl, lower alkylsulfonyl.
Scheme 7
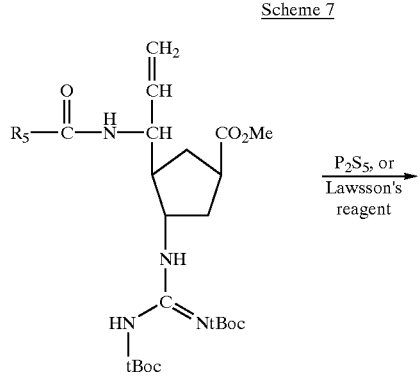
12
R₅ is lower alkyl.
Scheme 8
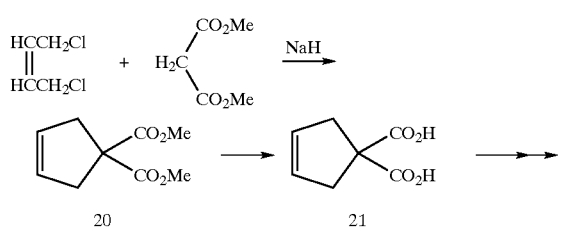
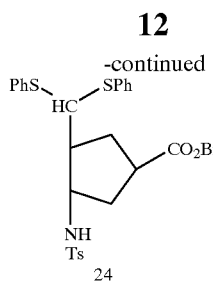
24
Bn is benzyl.
Ts is p-toluenesulfonyl.
Scheme 9
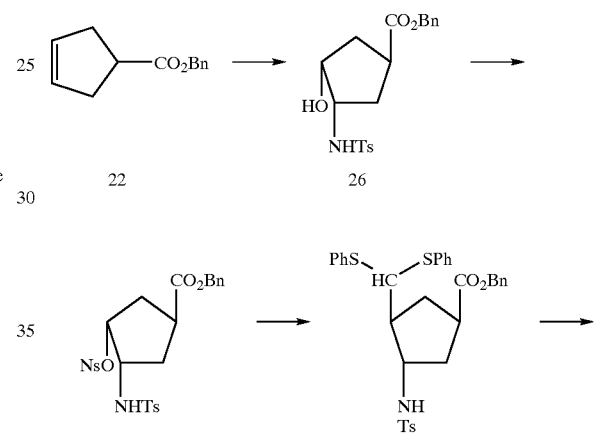
Bn is benzyl.
Ts is p-toluenesulfonyl.
Ns is 4-nitrophenylsulfonyl.
Scheme 10
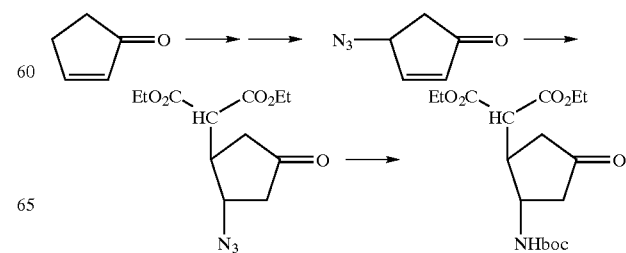

-continued
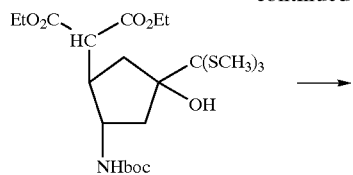
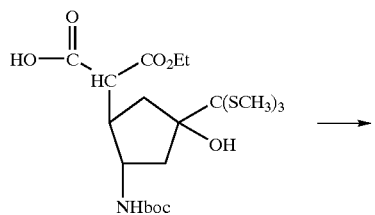
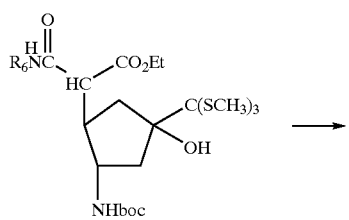
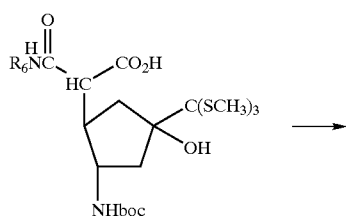
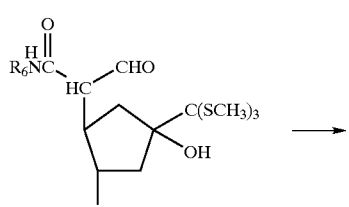
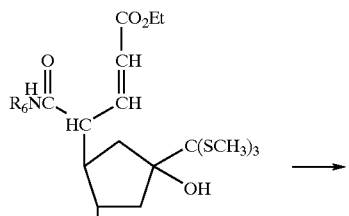
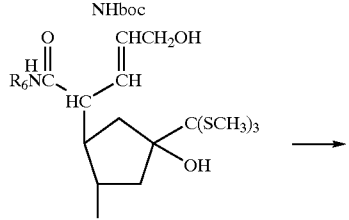
-continued
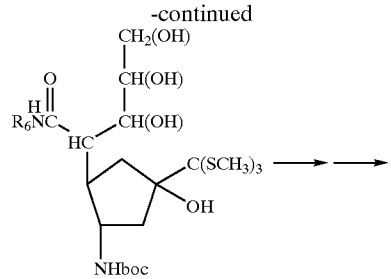
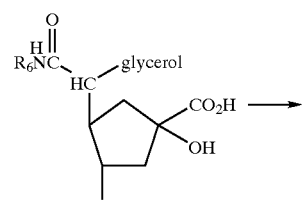
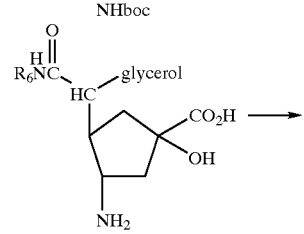
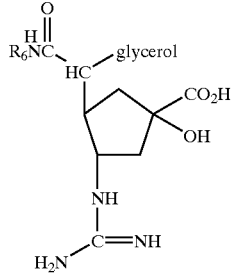
$R_6$ is H or lower alkyl.
The following Scheme 11 illustrates a procedure for preparing compounds of Examples 6, 7, 20, 26, 27, 28, and 29 represented by the formula:
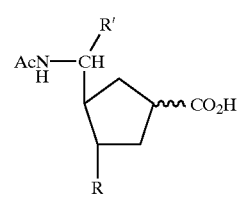
EXAMPLE
6 R=guanidine; R'=$CH_2OH$ isomer A at C-6
7 R=guanidine; R'=$CH_2OH$ isomer B at C-6
20 R=guanidine;
$R' = $ 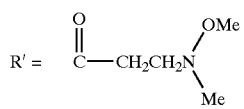

26 R=guanidine;
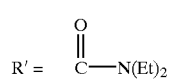
27 R=guanidine;
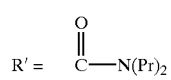
28 R=guanidine;
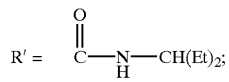
isomer A
29 R=guanidine;
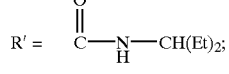
isomer B
Scheme 11
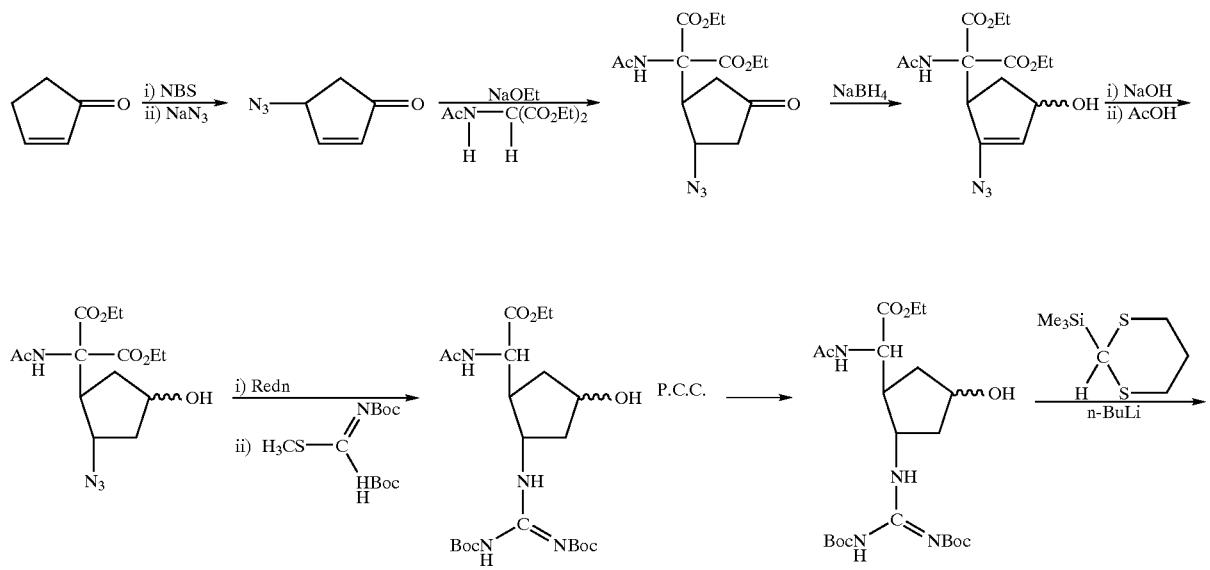
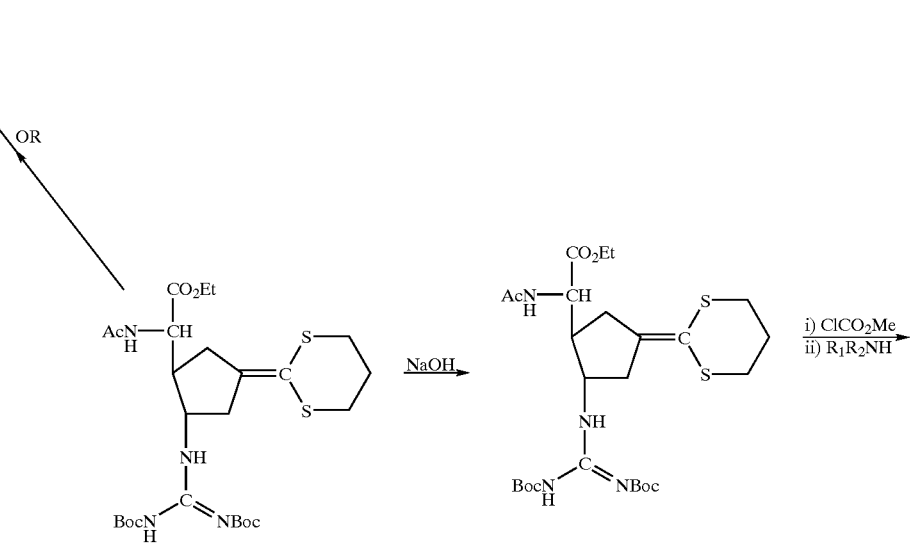

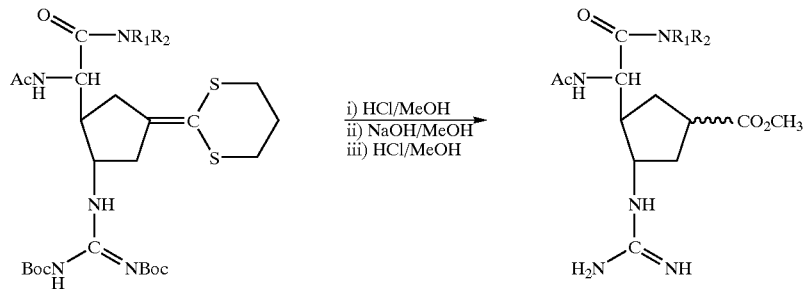
The following scheme 12A or scheme 12B illustrates a procedure for preparing compounds of examples 16, 17, 19, 24, and 25 represented by the formula:
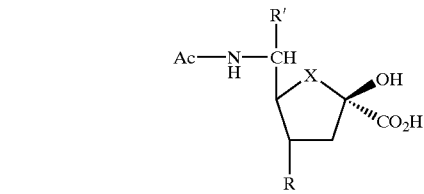
EXAMPLE
16 R=guanidine,
R' = CH$_2$OCCF$_3$
17 R=guanidine,
R' = CH$_2$OCCF$_3$
19 R=guanidine,
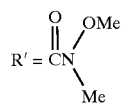
24 R=guanidine,
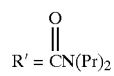
R' = CN(Pr)$_2$
25 R=guanidine,
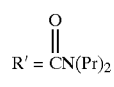
R' = CN(Pr)$_2$
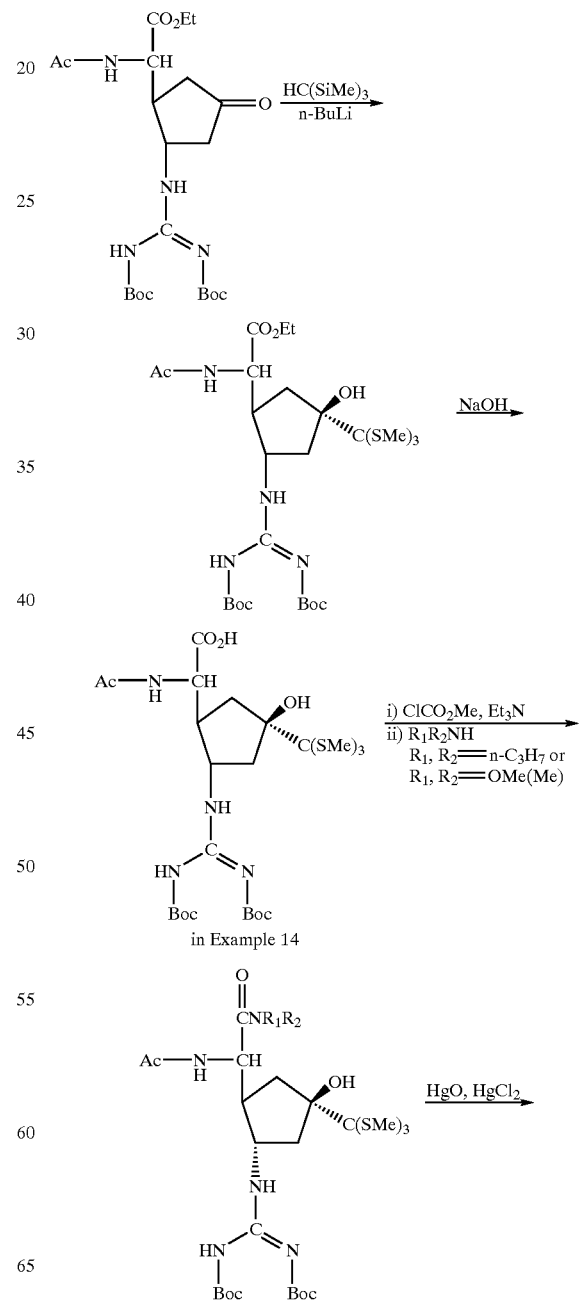
Scheme 12A 19
-continued
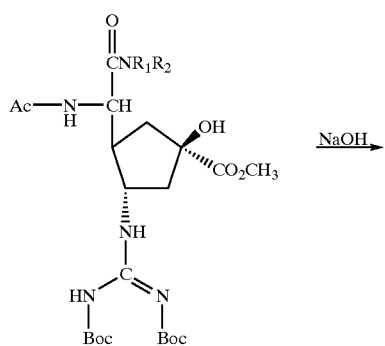
NaOH→
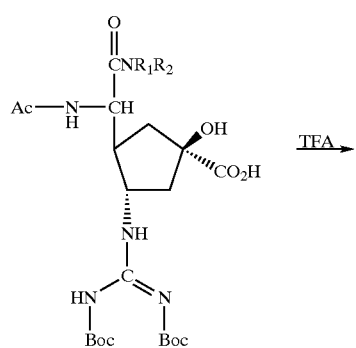
TFA→
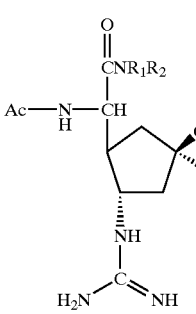
The product according to Examples 19, 24, and 25 depends upon $R_1$ and $R_2$ and the isomer precursor.
Scheme 12B
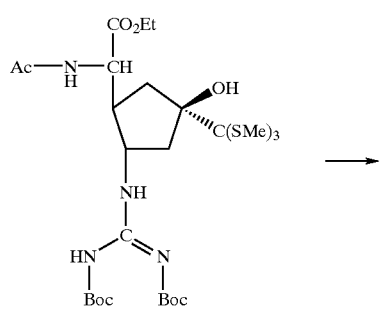
20
-continued
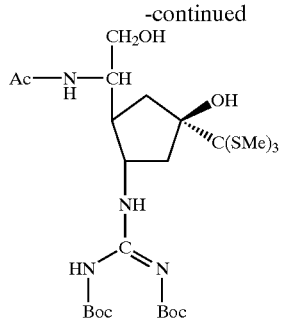
→
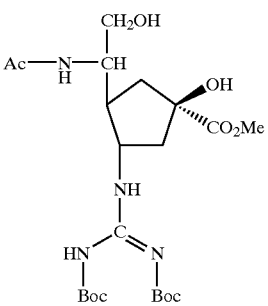
The product of Examples 16 and 17 depends upon the isomer of the precursor.
F~Compounds of Examples 6 and 7
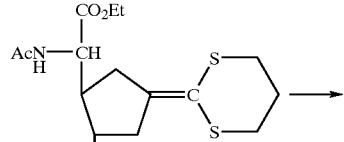
→
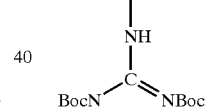
Yields the compounds of Examples 6 and 7, depending upon the isomer
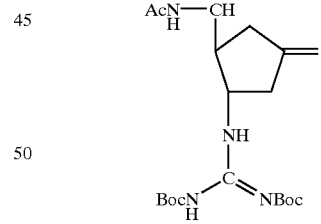
F~Compounds of Examples 26, 27, 28 and 29
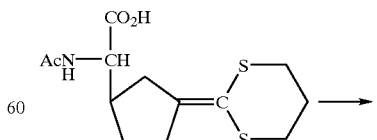
→
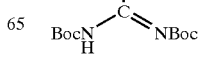

-continued

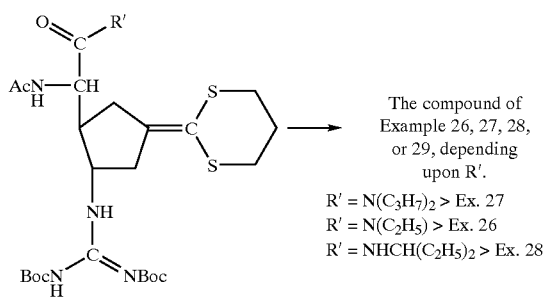

The compound of Example 26, 27, 28, or 29, depending upon R'.
R' = N(C$_3$H$_7$)$_2$ > Ex. 27
R' = N(C$_2$H$_5$) > Ex. 26
R' = NHCH(C$_2$H$_5$)$_2$ > Ex. 28 & 29

F~the Compound of Example 20

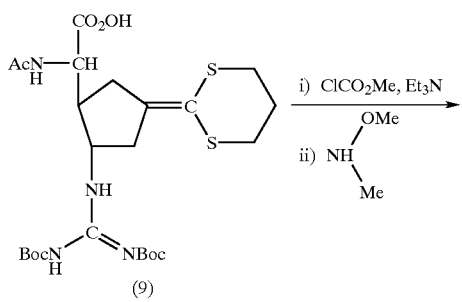
(9)

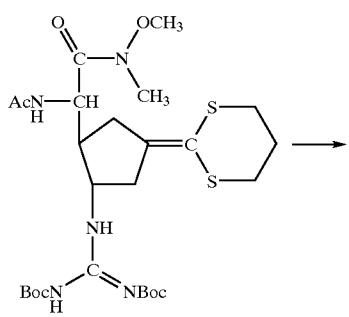

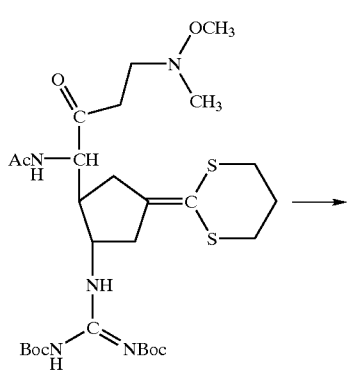

-continued

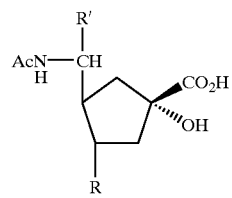

→ Compound of Example 20

The following Scheme 13 illustrates a procedure for preparing compounds of Examples 8, 9, 18, 21, 22 and 23 represented by the following formula:

$$\text{structure}$$

EXAMPLE

8  R=NH$_2$, R'=CH$_2$OH
9  R=guanidine, R'=CH$_2$OH
18 R=NH2, R'=CH$_2$OCH$_2$C$_6$H$_5$
21 R=guanidine,

22 R=NH$_2$,

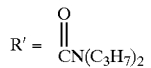

23 R=guanidine,

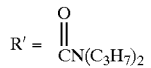

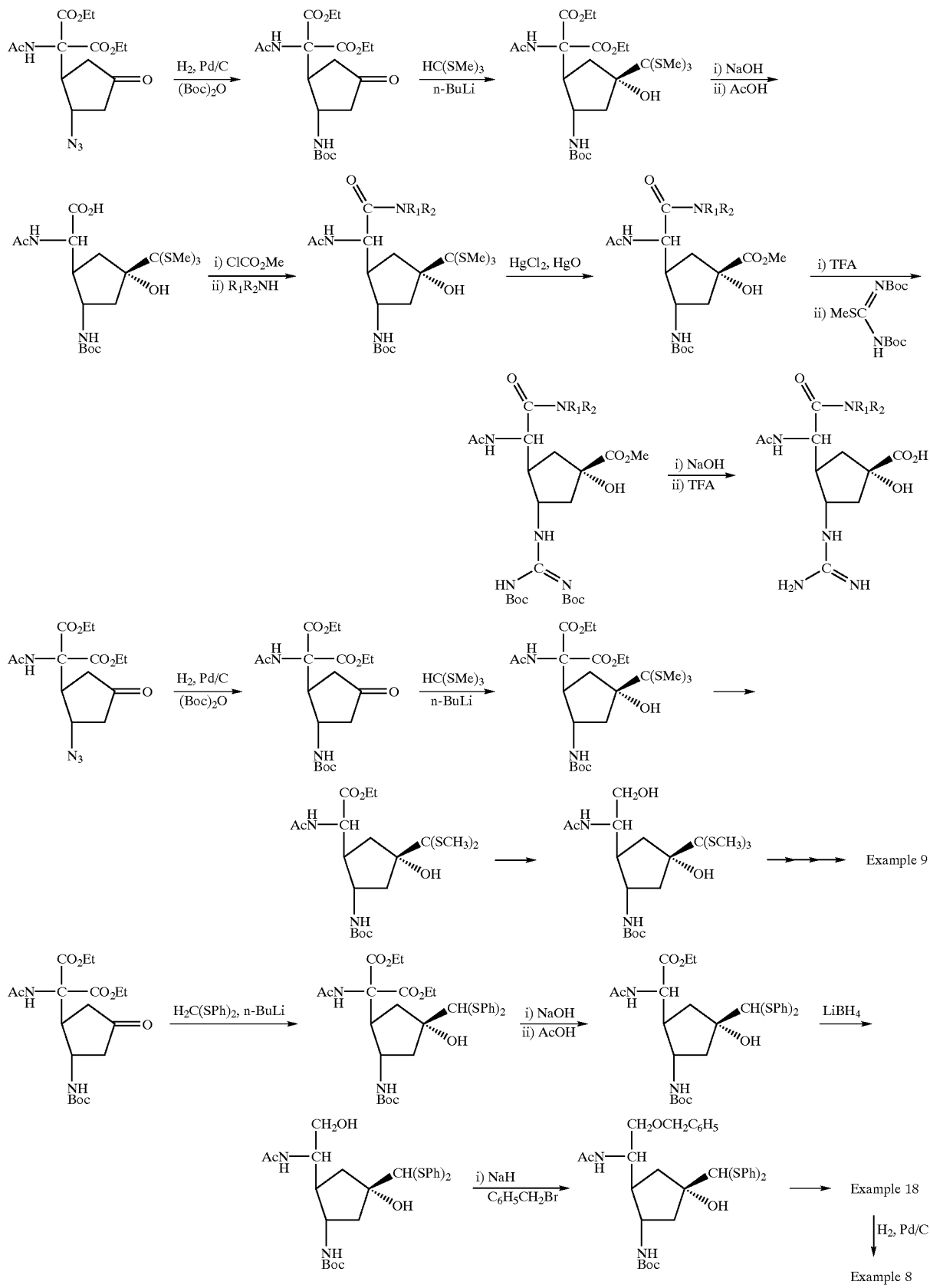

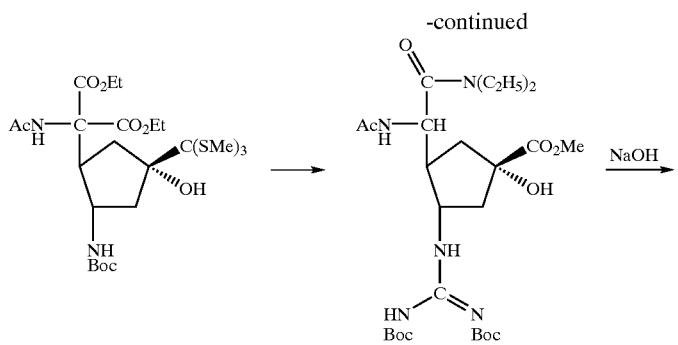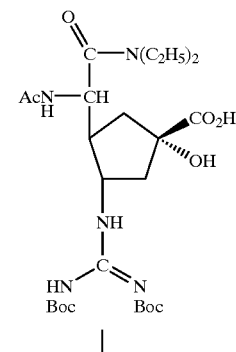
Example 21
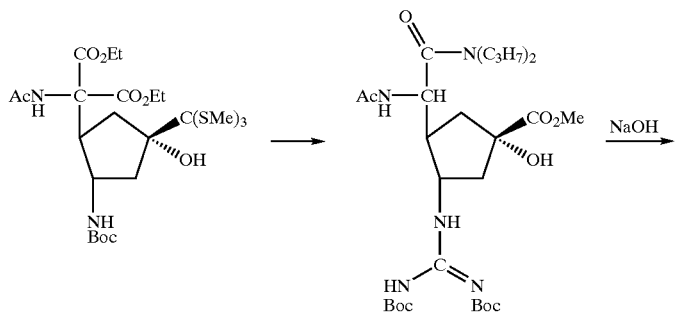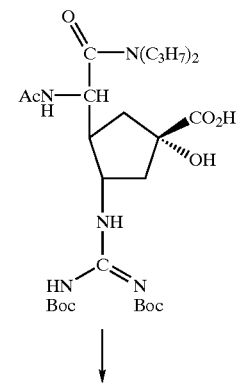
Example 23
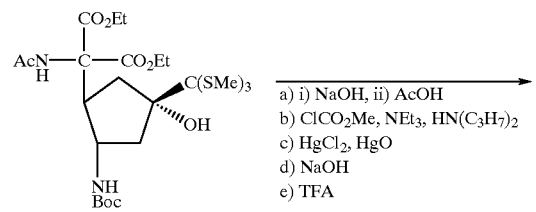
a) i) NaOH, ii) AcOH
b) ClCO₂Me, NEt₃, HN(C₃H₇)₂
c) HgCl₂, HgO
d) NaOH
e) TFA
Example 22
The following Scheme 14 illustrates a procedure for preparing compounds of Examples 10, 11, 12, 13, 14, and 15 represented by the formula:
Scheme 14
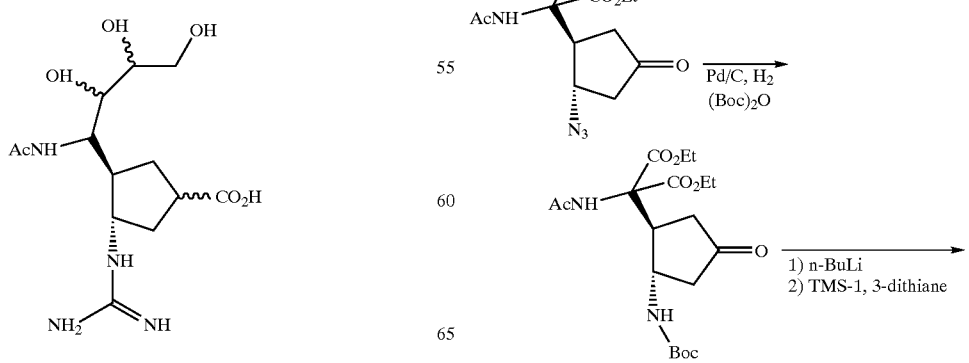

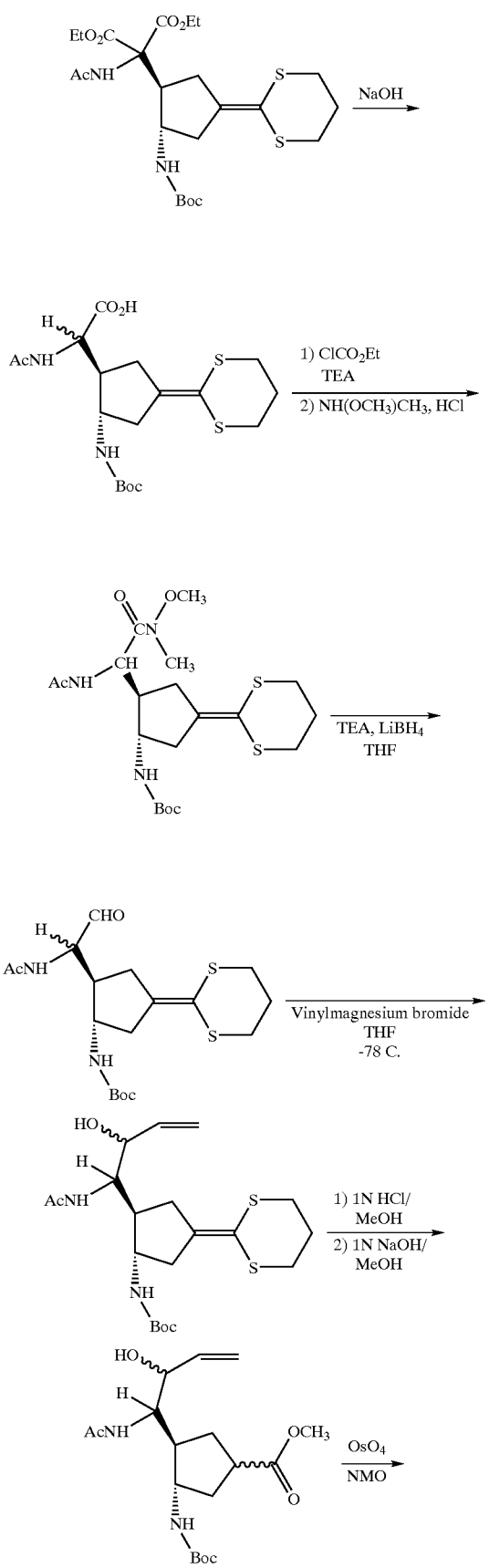
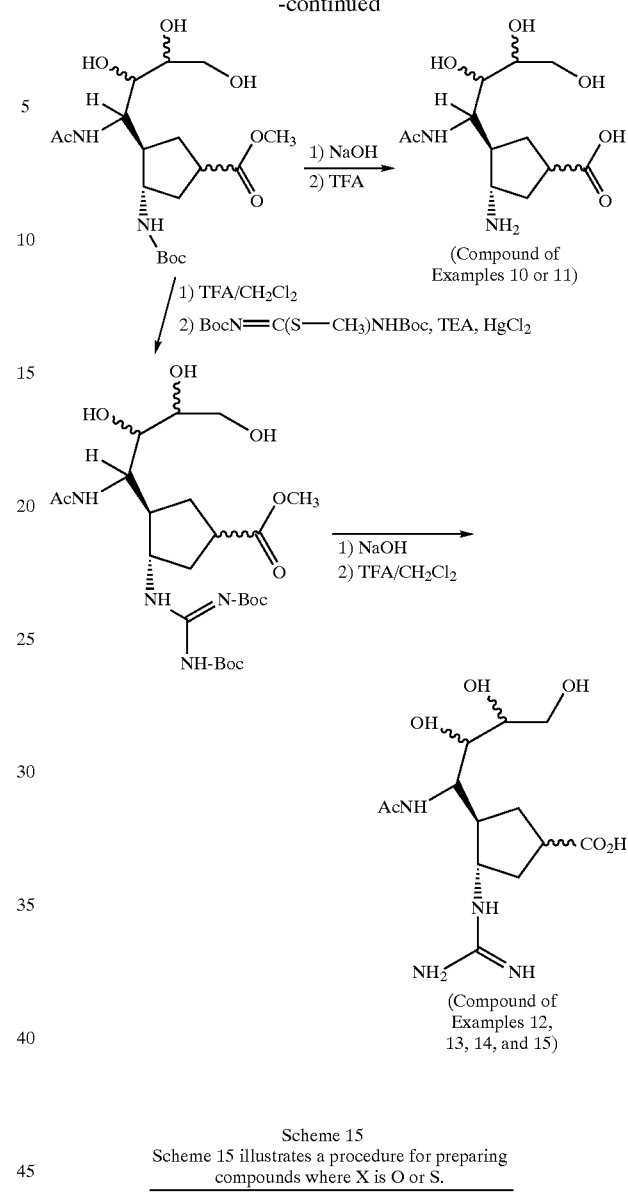
Scheme 15
Scheme 15 illustrates a procedure for preparing compounds where X is O or S.
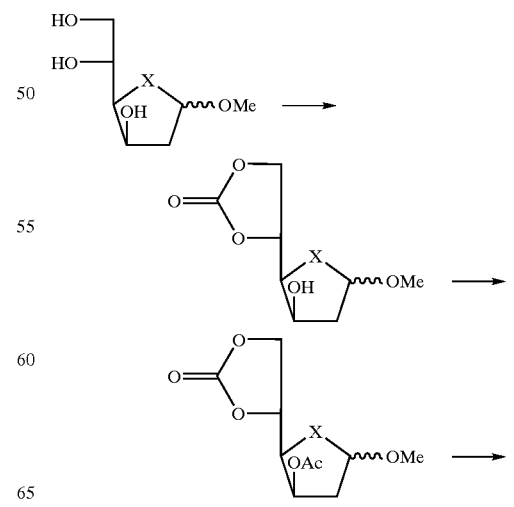

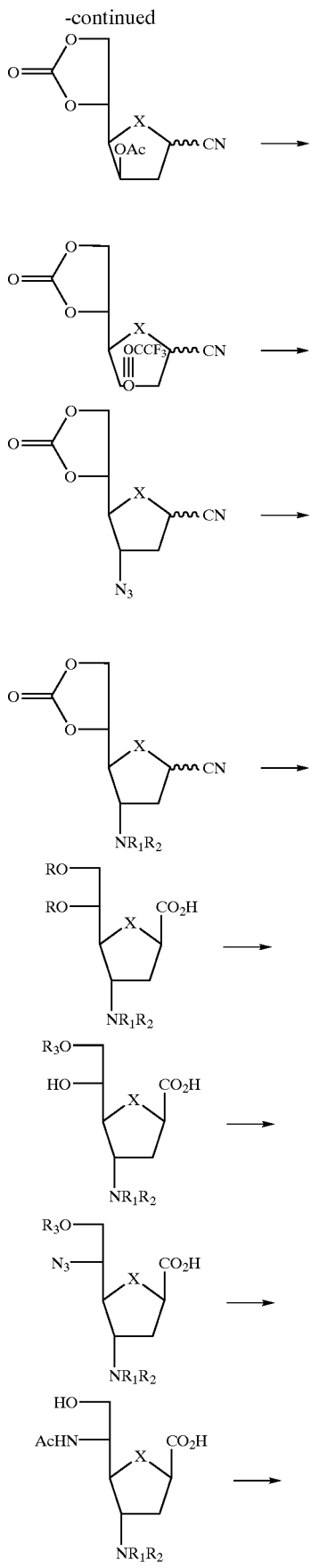

-continued

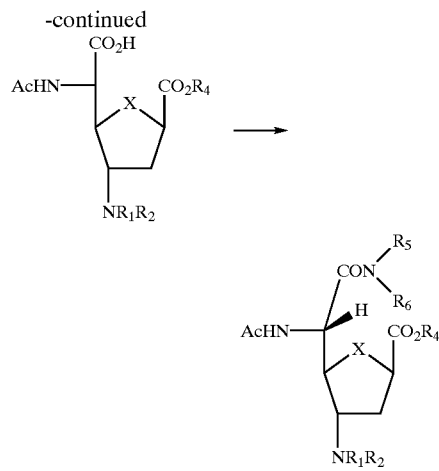

The following non-limiting Examples are presented to further illustrate the present invention.

Example 1

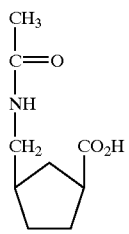

cis-3-[(methylcarbonylamino)methyl]cyclopentancarboxylic acid

To a mixture of cis-3-(methoxycarbonyl)cyclopentancarboxylic acid [prepared according to the procedure disclosed by Tucjan J. J. Horonowski and Walter A. Szorek. Can. J. Chem. 66 61–70 (1988); 17.2 g, 0.1 mmol] and triethylamine (10.1 g, 0.1 mmol) in tetrahydrofuran (300 mL) was added ethyl chloroformate (10.9 g, 0.1 mmol) at about –5° C. over a period of about 30 min. The mixture was further stirred for about 15 min at about –5° C. The resultant thick slurry was filtered and the solids were washed with tetrahydrofuran. The combined filtrates were cooled to about 10° C. and sodium borohydride (14.5 g, 0.38 mol) was added with stirring in one portion. The mixture was stirred further for about 10 min and methanol (62 mL) added dropwise over a period of about 1 h at about 10° C. When methanol addition was completed, 6 N hydrochloric acid was added slowly until neutralization. An organic layer was collected and an aqueous layer was extracted thrice with ether. The combined organic extracts were dried, filtered, and concentrated. The residue was dissolved in ether (about 300 mL), and a white solid was precipitated which was removed by filtration. The filtrate was concentrated and the residue passed through a column of silica gel using about 2% methanol in chloroform. The appropriate fractions were combined and concentrated to give 12.5 g (79%) of methyl cis-3-hydroxymethylcyclopentancarboxylate.

To a mixture of methyl cis-3-hydroxymethylcyclopentancarboxylate (4.74 g, 30 mmol) in dry benzene (about 250 mL) was added triphenyl phosphine (7.86 g, 30 mmol), diethyl azodicarboxylate (5.22 g, 30 mmol) and hydrazoic acid (2.5 M in toluene, 14.0 mL, 35 mmol). The mixture was stirred at room temperature for about 16 h. The reaction mixture was concentrated and the residue was dissolved in ethyl acetate and hexane was added. A precipitate formed on standing in about 2 h and was removed by filtration. The filtrate was concentrated and the residue was passed through a column of silica gel using chloroform as eluent. The appropriate fractions were combined and concentrated to give 2.6 g (47%) of methyl cis-3-azidomethyl-cyclopentancarboxylate.

A mixture of methyl cis-3-azidomethylcyclopentancarboxylate (1.2 g, 6.5 mmol) and 1 N sodium hydroxide (12.0 mL, 12 mmol) was stirred at room temperature for about 8 h. The alkaline mixture was extracted with chloroform. The aqueous layer was acidified with hydrochloric acid and extracted twice with chloroform. Combined chloroform extracts from the acidic mixture were dried over sodium sulfate, filtered and concentrated to give about 1.0 g (91%) of cis-3-azidomethylcyclopentancarboxylic acid.

Analysis: Calculated for $C_7H_{11}N_3O_2$: C, 49.70; H, 6.55; N, 24.84 Found: C, 49.92; H, 6.49; N, 24.58

A mixture of cis-3-azidomethylcyclopentancarboxylic acid (0.9 g, 5.3 mmol) in methanol (about 30 mL) was hydrogenated at about 50 psi and room temperature in the presence of 10% Pd on carbon (about 40 mg) for about 1 h. The catalyst was removed by filtration and the filtrate concentrated to give a syrup. When the syrup was dissolved in dimethylformamide and dichloromethane for acetylation (next step), formation of some white precipitate occurred. The precipitate was collected by filtration, washed with dichloromethane and dried to give cis-3-aminomethylcyclopentanecarboxylic acid as a white powder, mp 186–188° C. The yield of syrup was 0.7 g (100%). The white solid obtained was about 0.35 g. The remainder of the material from the dimethylformamide and dichloromethane mixture was not recovered, but was used for the acetylation step.

Analysis: Calculated for $C_7H_{13}NO_2.0.1H_2O$: C, 57.99; H, 9.18; N, 9.66 Found: C, 57.70; H, 9.01; N, 9.50

To a mixture of cis-3-aminomethylcyclopentancarboxylic acid (0.2 g, 1.4 mmol) in pyridine (about 5 mL) was added acetic anhydride (about 1 mL) and the mixture stirred at about 70° C. for about 2 h. The solvent was removed under reduced pressure, water was added several times and evaporated in vacuo. A light, viscous oil was obtained and dried in vacuo over acetone reflux to give 0.25 g (97%) of cis-3-[(methylcarbonylamino)methyl]cyclopentancarboxylic acid.

Analysis: Calculated for $C_9H_{15}NO_3$: C, 58.36; H, 8.16; N, 7.56 Found: C, 58.90; H, 7.94; N, 6.90

Example 2

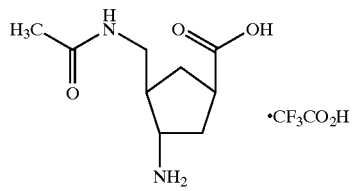

t-3-amino-c-4-(methylcarbonylamino)methyl-r-cyclopentancarbonylic acid trifluoroacetic acid [1:1]

To a mixture of c-2-acetyloxy-c-4-methoxycarbonyl-r-cyclopentancarboxylic acid [prepared according to the procedure disclosed by Tucjan J. J. Horonowski and Walter A. Szorek, Can. J. Chem. 63 2787–2797 (1985); 23.4 g, 101.64 mmol] in tetrahydrofuran (about 250 mL) and triethylamine (about 14.96 mL, 106.7 mmol), ethyl chloroformate (about 10.2 mL, 106.7 mmol) was added over a period of about 15 min at about 0° C. After stirring for an additional 30 min at the same temperature, the mixture was filtered with suction, and the cake washed with tetrahydrofuran (3×10 mL).

Sodium borohydride (15.7 g, 406.56 mmol) was added to the filtrate in one portion. Then methanol (about 64 mL) was added dropwise over a period of about one hour at about 10° C. After stirring for additional 30 min the reaction mixture was quenched carefully with 1 N HCl to pH 7. The solvent was removed in vacuo to obtain a white solid. The solid was dissolved in water (about 50 mL) and HCl (1 N) is added to adjust the pH to about 6. The solution was homogeneous. The solution was extracted with ethyl acetate (4×150 mL). The organic layers are combined and washed with brine (about 150 mL) and dried with sodium sulfate. The solvent was removed in vacuo to give a white solid. The white solid was dissolved in ether (about 200 mL) and filtered to remove insoluble impurities. The filtrate was concentrated in vacuo to furnish 21.5 g (97%) of a mixture of methyl c-4-methylcarbonyoxymethyl-c-3-hydroxycyclopentancarboxylate, methyl c-3-methylcarbonyloxy-c-4-hydroxymethylcyclopentan-r-carboxylate, and methyl c-3-hydroxy-c-4-hydroxymethylcyclopentan-r-carboxylate.

The above mixture was dissolved in methanol (about 200 mL) and sodium methoxide solution (about 7 mL, 25% wt in methanol) was added dropwise at room temperature. The reaction mixture ws stirred for about 90 min and solvent was removed in vacuo. The white residue was purified by flash column chromatography {20–40% [chloroform/methanol/conc ammonium hydroxide (80:18:2)] in dichloromethane} to furnish 13.2 g (76%) of pure methyl c-3-hydroxy-c-4-hydroxymethylcyclopentan-r-carboxylate as a white solid.

To methyl c-3-hydroxy-c-4-hydroxymethylcyclopentan-r-carboxylate (13.2 g, 76.3 mmol), triphenylphosphine (44.5 g, 167.86 mmol) and diethyl azodicarboxylate (27.82 mL, 167.86 mmol) in anhydrous benzene (about 800 mL) was added dropwise with stirring under nitrogen at room temperature hydrazoic acid (1 M solution in toluene, 190.75 mL, 190.75 mmol) over a period of about 30 min. The reaction mixture was stirred overnight at room temperature and concentrated in vacuo to half the original volume. The solid obtained on standing was removed by filtration and the filtrate was concentrated in vacuo to furnish an orange residue. The residue was crystallized from ethyl acetate/hexane to remove triphenylphosphine oxide and 1,2-ethoxycarbonylhydrazine. The filtrate is concentrated in vacuo and purified by flash column chromatography (5–25% ethyl acetate in hexane) to furnish 8.8 g (52%) of methyl t-3-azido-c-4-azidomethylcyclopentan-r-carboxylate.

To methyl t-3-azido-c-4-azidomethylcyclopentan-r-carboxylate (about 8.4 g, 37.5 mmol) was added 1 N sodium hydroxide (112.5 mL, 112.5 mmol) and stirred overnight at room temperature. The reaction mixture was extracted with chloroform (3×20 mL). The aqueous layer was acidified to pH 4 using conc HCl and extracted with chloroform (4×25 mL). The organic layers were combined, dried with magnesium sulfate, filtered through a pad of silica and concentrated in vacuo to obtain 7.58 g (96%) of t-3-azido-c-4-azidomethyl-c-cyclopentan-r-carboxylic acid as a colorless oil.

Analysis: Calculated for $C_7H_{10}N_6O_2$: C, 40.00; H, 4.80; N, 39.98 Found: C, 40.24; H, 4.88; N, 39.73

To a solution of t-3-azido-c-4-azidomethylcyclopentan-r-carboxylic acid (1.05 g, 5.0 mmol), dicyclohexylcarbodiimide (2.5 g, 12 mmol) and 4-dimethylaminopyridine (60 mg, 0.5 mmol) in dichloromethane (about 25 mL), was added dropwise over a period of about 15 min at room temperature tert-butanol (0.97 mL, 10.0 mmol). After stirring at room temperature overnight, the mixture was filtered with suction and the cake washed with ether (3×5 mL). The filtrate was concentrated in vacuo and ether (about 25 mL) was added to the residue. The organic layer was washed with cold HCl (1%, 20 mL), saturated sodium bicarbonate (2×20 mL), water (20 mL), dried with magnesium sulfate, filtered and solvent removed in vacuo to obtain 2.92 g of an oil. Purification of the crude by flash column chromatography (2–5% ether in hexane) provided 0.39 g (29%) of t-3-azido-c-4-azidomethyl-r-1-tert-butoxycarbonylcyclopentane as a colorless oil.

Analysis: Calculated for $C_{11}H_{18}N_6O_2$: C, 49.61; H, 6.81; N, 31.56 Found: C, 49.83; H, 6.76, N, 31.38

To a solution of t-3-azido-c-azidomethyl-r-1-tert-butoxycarbonylcyclopentane (0.33 g, 1.22 mmol) in methanol (about 10 mL) was added under nitrogen Pd/C (0.1 g, 10% Palladium content) and the resulting mixture hydrogenated at about 50 psi for about 20 min. The hydrogen was evacuated, and after addition of fresh hydrogen, the resulting mixture was hydrogenated at about 50 psi for about 40 min. The catalyst was removed by filtration through Celite. The filtrate was concentrated in vacuo to furnish about 0.25 g (97%) of t-3-amino-c-4-aminomethyl-r-1-tert-butoxycarbonylcyclopentane.

To a solution of t-3-amino-c-4-aminomethyl-r-1-tert-butoxycarbonylcyclopentane (0.25 g, 1.22 mmol), in dichloromethane (about 10 mL), cooled to 0° C. is added dropwise with stirring over a period of about 5 min acetic anhydride (0.098 mL, 1.04 mmol). After stirring at 0° C. for about one h, the reaction mixture was stirred at room temperature overnight. The solvent was removed in vacuo to obtain a white solid. The crude is purified by flash column chromatography {30–100% [chloroform/methanol/conc ammonium hydroxide(80:18:2)] in dichloromethane} and furnished:

1. t-3-methylcarbonylamino-c-4-(methylcarbonylamino) methyl-r-tert-butoxycarbonyl-cyclopentane, 0.04 g (11%) as a white solid, mp 170–172° C.

Analysis: Calculated for $C_{15}H_{26}N_2O_4 \cdot 0.25H_2O$: C, 59.48; H, 8.82: N, 9.25 Found: C, 59.59; H, 8.82; N, 9.17

2. t-3-amino-c-4-(methylcarbonylamino)methyl-r-1-tert-butoxycarbonylcyclopentane, 0.12 g (39%) as a white solid, mp 86–87° C.

Analysis: Calculated for $C_{13}H_{24}N_2O_3$: C, 60.91; H, 9.44; N, 10.93 Found: C, 60.69; H, 9.40; N, 10.87

3. t-3-amino-c-4-aminomethyl-r-1-tert-butoxycarbonylcyclopentane, 0.05 g (20%) as a colorless oil. The oil was dissolved in dichloromethane (2 mL) and acetic acid (3 equi) was added. The resulting solution was stirred for 15 min and the solid obtained was filtered to obtain the product as an acetate, mp 124–127° C.

Analysis: Calculated for $C_{11}H_{22}N_2O_2 \cdot 2C_2H_4O_2 \cdot 0.25H_2O$: C, 53.16; H, 9.07; N, 8.27 Found: C, 53.34; H, 8.81; N, 8.46

To a solution of t-3-amino-c-4-(methylcarbonylamino) methyl-r-1-tert-butoxycarbonyl-cyclopentane (0.09 g, 0.32 mmol) in dichloromethane (about 3 mL) was added dropwise trifluoroacetic acid (about 0.67 mL, 8.8 mmol) and stirred at room temperature for about 2 h. The solvent was removed in vacuo and the excess trifluoroacetic acid was removed by co-distilling thrice in vacuo with dichloromethane (about 5 mL) to obtain 0.1 g (99%) of t-3-amino-c-4-[(methylcarbonylamino)methyl]-cyclopentan-r-carboxylic acid trifluoroacetic acid as a hydroscopic, tan solid.

Analysis: Calculated for $C_9H_{16}N_2O_3 \cdot CF_3CO_2H$: C, 42.04; H, 5.45; N, 8.90 Found: C, 41.75; H, 5.58; N, 8.59

Example 3

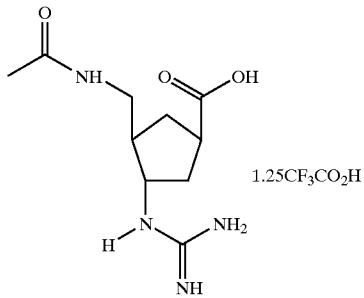

t-3-{[(Amino)(imino)methyl]amino}-c-4-[(methylcarbonylamino)methyl]-cyclopentan-r-carboxylic acid trifluoroacetic acid [1:1.25]

To a stirred solution of t-3-azido-c-4-azidomethylcyclopentan-r-carboxylic acid from Example 2 (about 4.0 g, 19.05 mmol) in dichloromethane (about 40 mL) was rapidly added liquefied isobutylene (about 20 mL), followed by the dropwise addition of phosphoric acid (prepared by saturating 2.5 mL of 85% $H_3PO_4$ with $P_2O_5$) in dichloromethane (2.5 mL) and boron trifluoride etherate (0.9 mL). After the mixture was stirred at about −78° C. for about 2 h at room temperature overnight, ice-water and saturated aqueous $NaHCO_3$ was added until the mixture becomes basic. The aqueous layer was extracted with dichloromethane (2×20 mL). The organic layers were combined, washed with water (20 mL) and brine (20 mL), dried over anhydrous $MgSO_4$, and concentrated in vacuo to furnish 1.7 g of a colorless oil. Purification of the crude by flash column chromatography (5–10% ether in hexane) gave 1.2 g (24%) of t-3-azido-c-4-azidomethyl-r-1-tert-butoxycarbonylcyclopentane.

To a solution of t-3-azido-c-4-azidomethyl-r-1-tert-butoxycarbonylcyclopentane (1.22 g, 4.6 mmol) in methanol (20 mL) was added under nitrogen Pd/C (0.1 g, 10% Palladium content) and the resulting mixture hydrogenated at about 50 psi for about 30 min. The hydrogen was evacuated, and after addition of fresh hydrogen, the resulting mixture was hydrogenated at about 50 psi for about 30 min. The catalyst was removed by filtration through Celite. The filtrate was concentrated in vacuo to furnish about 0.94 g (96%) of t-3-amino-c-4-aminomethyl-r-1-tert-butoxycarbonylcyclopentane.

To a solution of t-3-amino-c-4-aminomethyl-r-1-tert-butoxycarbonylcyclopentane (0.63 g, 2.95 mmol), in dichloromethane (30 mL), cooled to about −5° C. acetic anhydride (0.25 mL, 2.65 mmol) was added dropwise with stirring over a period of about 5 min. After stirring at 0° C. for about one hour the reaction mixture was stirred at room temperature overnight. The solvent was removed in vacuo to obtain a white solid. Purification of the crude by flash column chromatography {30–100% [chloroform/methanol/conc ammoniumhydroxide (80:18:2)] in dichloromethane} gives 0.33 g (44%) of t-3-amino-r-1-tert-butoxycarbonyl-c-4-(methylcarbonylamino)methylcyclopentane.

To t-3-amino-r-1-tert-butoxycarbonyl-c-4-(methylcarbonylamino)methylcyclopentane (0.33 g, 1.29 mmol) in dimethyl formamide (about 5 mL) was added triethylamine (0.63 mL, 4.52 mmol) and bis-bocthiourea (0.4 g, 1.42 mmol). The resulting mixture was cooled to 0° C. and mercuric chloride (0.39 g, 1.42 mmol) was added.

The reaction mixture was stirred at 0° C. for about 30 min and then at room temperature overnight. Ethyl acetate (about 50 mL) was added and the slurry filtered through Celite. The filtrate was washed with water (2×20 mL) and brine (20 mL), the organic layer was dried (MgSO$_4$), filtered, and solvent removed in vacuo to give about 0.7 g of crude. The crude was purified by flash column chromatography (30–50% ethyl acetate in hexane) and recrystallized from ether/hexane to obtain 0.51 g (79%) of a colorless oil. The oil was crystallized from petroleum ether to obtain t-3-{[(tert-butoxycarbonylamino)(tert-butoxycarbonylimino)methyl]amino}-cis-1-tert-butoxycarbonyl-c-4-(methylcarbonylamino)-methyl]cyclopentane as a white solid, mp 145–146° C.

Analysis: Calculated for $C_{24}H_{42}N_4O_7$: C, 57.81; H, 8.49; N, 11.24 Found: C, 57.70; H, 8.52; N, 10.98

To a solution of t-3-{[(tert-butoxycarbonylamino)(tert-butoxycarbonyl-imino)methyl]amino}-cis-1-tert-butoxycarbonyl-c-4-[(methylcarbonylamino)methyl]cyclopentane (0.44 g, 0.88 mmol) in dichloromethane (about 9 mL) is added dropwise trifluoroacetic acid (1.7 mL, 22.1 mmol) and stirred at room temperature for about 1 h. The solvent was removed in vacuo and the excess trifluoroacetic acid was removed by co-distilling thrice in vacuo with dichloromethane (about 5 mL) to obtain a white solid. The white solid was triturated with ether and dried in vacuo at acetone reflux to obtain 0.21 g (67%) of t-3-{[(amino)(imino)methyl]amino}-c-4-[(methylcarbonylamino)methyl] cyclopentan-r-carboxylic acid trifluoroacetic acid as a hygroscopic solid.

Analysis: Calculated for $C_9H_{16},N_2O_3 \cdot 1.25CF_3CO_2H$: C, 39.30; H. 5.04; N. 14.56 Found: C; 39.21; H, 5.29; N, 14.26

Example 4

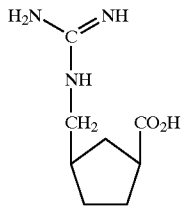

c-3-{{[(Amino)(imino)methyl]amino}methyl}cyclopentan-r-carboxylic acid

To a mixture of c-3-aminomethylcyclopentancarboxylic acid from Example 1 (0.07 g, 0.5 mmol) and potassium carbonate (0.07 g, 0.5 mmol) in water (about 1.5 mL) was added aminoiminomethane sulphonic acid (0.06 g, 0.5 mmol) and the mixture was stirred for about 18 h at room temperature. A white solid separated, which was collected by filtration, washed with a small amount of water and dried in vacuo to give 0.04 g (49%) of c-3-{{[(amino)-(imino) methyl]amino}methyl}cyclopentancarboxylic acid as white powder, mp 280° C. (darkens).

Analysis: Calculated for $C_3H_{15}N_3O_2$: C, 51.88; H, 8.16; N, 22.69 Found: C, 51.79; H, 8.09; N, 22.63

Example 5

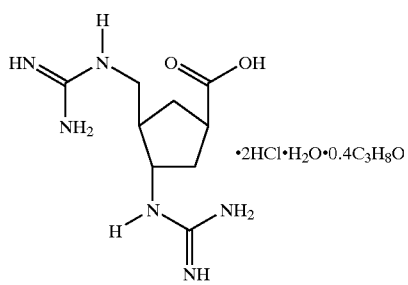

t-3-{[(Amino)(imino)methyl]amino}-c-4-{{[(amino)(imino)methyl]amino}methyl}cyclopentan-r-carboxylic acid dihydrochloride hydrate 2-propanol (5:10:5:2)

To a stirred solution of t-3-azido-c-4-azidomethylcyclopentan-r-carboxylic acid from Example 2 (about 4.0 g, 19.05 mmol) in dichloromethane (about 40 mL) was rapidly added liquefied isobutylene (about 20 mL), followed by the dropwise addition of phosphoric acid (prepared by saturating 2.5 mL of 85% $H_3PO_4$ with $P_2O_5$) in dichloromethane (2.5 mL) and boron trifluoride etherate (0.9 mL). After the mixture was stirred at about −78° C. for about 2 h at room temperature overnight, ice-water and saturated aqueous $NaHCO_3$ was added until the mixture becomes basic. The aqueous layer was extracted with dichloromethane (2×20 mL). The organic layers were combined, washed with water (20 mL) and brine (20 mL), dried over anhydrous MgSO$_4$, and concentrated in vacuo to furnish about 1.7 g of a colorless oil. Purification of the crude by flash column chromatography (5–10% ether in hexane) gave 1.2 g (24%) of t-3-azido-c-4-azidomethyl-r-1-tert-butoxycarbonylcyclopentane.

To a solution of t-3-azido-c-4-azidomethyl-r-1-tert-butoxycarbonylcyclopentane (1.22 g, 4.6 mmol) in methanol (about 20 mL) was added under nitrogen Pd/C (0.1 g, 10% Palladium content) and the resulting mixture hydrogenated at about 50 psi for about 30 min. The hydrogen was evacuated, and after addition of fresh hydrogen, the resulting mixture was hydrogenated at about 50 psi for about 30 min. The catalyst was removed by filtration through Celite. The filtrate was concentrated in vacuo to furnish about 0.94 g (96%) of t-3-amino-c-4-aminomethyl-r-tert-butoxycarbonylcyclopentane.

To a solution of t-3-amino-c-4-aminomethyl-r-tert-butoxycarbonylcyclopentane (0.32 g, 1.5 mmol) in dimethylformamide (about 5 mL) was added triethylamine (1.5 mL, 10.5 mmol) and bis-bocthiourea (0.91 g, 3.3 mmol). The resulting mixture was cooled to 0° C. and mercuric chloride (0.9 g, 3.3 mmol) was added. The reaction mixture was stirred at 0° C. for about 30 min and then at room temperature overnight. Ethyl acetate (about 25 mL) was added and the slurry filtered through Celite. The filtrate was washed with water (2×20 mL) and brine (20 mL), the organic layer dried (MgSO$_4$) filtered and solvent removed in vacuo to give about 1.22 g of crude. The crude is purified by flash column chromatography (25–36% ether in hexane) to furnish 0.75 g (71%) of a colorless oil. The oil was recrystallized from petroleum ether to obtain t-3-{(tert-butoxycarbonylamino)(tert-butoxycarbonylimino)methyl]amino}-c-4-{{tert-butoxycarbonyl-amino)(tert-butoxycarbonylimino)methyl]amino}methyl}-r-tert-butoxycarbonylcyclopentane as a white solid, mp 152–154° C.

Analysis: Calculated for $C_{33}H_{58}N_6O_{10}$: C, 56.72; H, 8.37; N, 12.03 Found: C, 56.96; H, 8.51; N, 12.06

A solution of t-3-{[(tert-butoxycarbonylamino)(tert-butoxycarbonylimino)methyl]amino}-c-4-{{[(tert-butoxycarbonylamino)(tert-butoxycarbonylimino)methyl]amino}methyl}-r-tert-butoxycarbonylcyclopentane (0.56 g, 0.88 mmol) in 5 N hydrochloric acid (about 1 mL) was stirred at room temperature for about 2 h. The solvent was removed in vacuo to furnish a hygroscopic residue. The residue was washed several times with ether and dried in vacuo at acetone reflux temperature to obtain 0.18 g (64%) of t-3-{[(amino)(imino)methyl]amino}-c-4-{{[(amino)(imino)methyl]amino}methyl}cyclopentan-r-carboxylic acid dihydrochloride hydrate 2-propanol (5:10:5:2) as a hygroscopic solid.

Analysis: Calculated for $C_9H_{16}N_2O_3 \cdot 2HCl \cdot H_2O \cdot 0.4C_3H_8O$: C; 34.29; H, 7.11; N, 23.52 Found: C; 34.38; H, 6.84; N, 23.94

Example 6

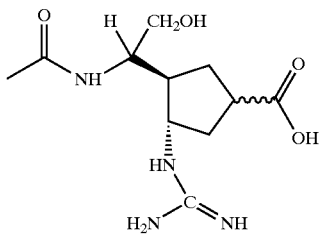

F.W. 272.30
4β-{[(Amino)(imino)methyl]amino}-3α-[(2-hydroxy-1-methylcarbonylamino)ethyl]-1-cyclo-pentancarboxylic acid (isomer A at C-6)

To a solution of sodium azide (2.12 g, 32.6 mmol) in dimethylformamide (15 mL) cooled to 0° C. was added dropwise with stirring 4-bromocyclopent-2-enone (DePuy, C. H.; Isaks, M.; Eilers, K. L.; Morris, G. F. *J. Org. Chem.* 1964. 29, 3503; 3.5 g, 21.7 mmol) in dimethyl-formamide (5 mL) over a period of 5 min. The reaction mixture was stirred at 0° C. for 30 min and diluted with ethyl acetate (20 mL). The reaction mixture was washed with water (2×20 mL) and brine (20 mL), dried (MgSO₄), filtered, and concentrated in vacuo to furnish an oily residue. Purification of the crude oil by flash column chromatography (10–15% ethyl acetate in hexane) gave 1.9 g (71%) of 4-azidocyclopent-2-enone as a light-yellow oil.

To a solution of diethyl acetamidomalonate (Aldrich, 1.25 g, 5.7 mmol) in ethanol (10 mL) under nitrogen was added freshly cut sodium metal (0.03 g, 1.4 mmol). The reaction mixture was stirred at room temperature until all sodium has dissolved. The reaction mixture was cooled to −40° C. (dry ice/acetonitrile) and a solution of 4-azidocyclopent-2-enone (0.7 g, 5.7 mmol) in ethanol (5 mL) was added dropwise over a period of 10 min. The reaction mixture was stirred at −40° C. for 30 min and quenched with trifluoroacetic acid (0.1 mL, 1.4 mmol). The solvent was removed in vacuo to furnish a white solid. Purification of the crude by flash column chromatography (60% ether in hexane) gave 1.2 g (63%) of trans-3-azido-4-[(methylcarbonyl-amino)bis(ethoxycarbonyl)methyl]cyclopentanone as a white solid, mp 121–122° C.

Analysis: Calculated for $C_{14}H_{20}N_4O_6$: C, 49.41; H, 5.92; N, 16.46 Found: C, 49.47; H, 5.95; N, 16.48

To a mixture of trans-3-azido-4-[bis(ethoxycarbonyl)(methylcarbonylamino)methyl]-cyclopentanone (8.2 g, 24.1 mmol) in methanol (100 mL) was added sodium borohydride (0.46 g, 12.1 mmol) in portions over a period of 5 min at room temperature. The reaction mixture was further stirred for 10 min and then acetic acid (1 mL) was added and mixture concentrated. The residue was dissolved in ethyl acetate (100 mL) and washed with water (1×100 mL) and brine (1×100 mL) and dried (MgSO₄). After filtration, the filtrate was concentrated to give 8.2 g (100%) of 3β-azido-4α-[bis(ethoxycarbonyl)(methylcarbonylamino)methyl]cyclopentanol, a mixture of isomers, as a light-brown oil.

Analysis: Calculated for $C_{14}H_{22}N_4O_6$: C, 49.12; H, 6.48; N, 16.37 Found: C, 49.16; H, 6.51; N, 16.11

A mixture of 3β-azido-4α-[bis(ethoxycarbonyl)(methylcarbonylamino)methyl]cyclo-pentanol, a mixture of isomers (8.0 g, 23.4 mmol), and sodium hydroxide (1 N, 72.0 mL, 72.0 mmol) was stirred for 16 h at room temperature. Acetic acid (glacial, 20 mL) was added and heated at gentle reflux for 2 h. The mixture was then extracted with ethyl acetate (3×100 mL). The combined organic layers were washed with water (2×100 mL) and brine (1×100 mL) and dried (MgSO₄). After filtration, the filtrate was concentrated and the residue passed through a column of silica gel using ethyl acetate as an eluent to give 4.0 g (63%) of 3β-azido-4α-[(ethoxycarbonyl)(methylcarbonylamino)methyl]cyclopentanol, a mixture of isomers, as a colorless syrup.

Analysis: Calculated for $C_{11}H_{18}N_4O_4$: C, 48.89; H, 6.71; N, 20.72 Found: C, 48.76; H, 6.72; N, 20.65

A mixture of the above alcohol, a mixture of isomers (3.8 g, 14.0 mmol), in ethyl acetate (120 mL) was hydrogenated in the presence of Pd/C (250 mg, 10% Palladium content) at 40 psi and room temperature for 16 h. The catalyst was removed by filtration and the filtrate concentrated to give 2.8 g (82%) of 3β-amino-4α-[(ethoxycarbonyl)(methylcarbonylamino)-methyl]cyclopentanol as a syrup.

To a mixture of 3β-amino-4α-[(ethoxycarbonyl)(methylcarbonylamino)methyl]cyclo-pentanol (2.8 g, 11.5 mmol) in dimethylformamide (25 mL) was added triethylamine (4.06 g, 40.02 mmol). The mixture was cooled in an ice bath and bis-bocthiourea (3.17 g, 11.5 mmol) was added, stirred for 10 min and mercury(II) chloride (3.12 g, 11.5 mmol) added. The reaction mixture was stirred at ice bath temperature for 1 h, diluted with ethyl acetate (100 mL), and filtered through Celite. The filtrate was washed with water (1×100 mL) and brine (1×100 mL) and dried (MgSO₄). After filtration, the filtrate was concentrated and the residue passed through a column of silica gel (100 g) using ethyl acetate as an eluent to give 5.0 g (89%) of 3β-{[(tert-butoxycarbonylamino)(tert-butoxycarbonylimino)methyl]amino)-4α-[(ethoxycarbonyl)(methyl-carbonylamino)methyl]cyclopentanol, a mixture of isomers, as a white foam. An analytical sample was prepared by recrystallization from ethyl acetate/hexane.

Analysis: Calculated for $C_{22}H_{38}N_4O_8$: C, 54.31; H, 7.87: N, 11.51 Found: C, 54.47; H, 7.95; N, 11.39

To a mixture of 3β-{[(tert-butoxycarbonylamino)(tert-butoxycarbonyl-imino) methyl]amino}-4α-[(ethoxycarbonyl)(methylcarbonylamino)methyl] cyclopentanol (4.02 g, 8.27 mmol) in dichloromethane (75 mL) was added pyridinium chlorochromate (5.3 g, 24.8 mmol) and stirred at room temperature for 16 h. The mixture was diluted with ether, the reaction filtered through Celite, and the filtrate concentrated. The residue was passed through a column of silica gel (200 g) using ethyl acetate/hexane (1:1) as an eluent to give:

1. 0.62 g (15%) of isomer A, higher running spot on TLC in ethyl acetate, as a white powder, mp 175° C. An analytical sample of 3β-{[(tert-butoxycarbonyl-amino)(tert-butoxycarbonylimino)methyl]amino}-4α-

[(ethoxycarbonyl)(methyl-carbonylamino)methyl] cyclopentanone, isomer A, was prepared by recrystallization from ethyl acetate/hexane.

Analysis: Calculated for $C_{22}H_{36}N_4O_8$: C, 54.53; H, 7.49; N, 11.56 Found: C, 54.50; H, 7.44; N, 11.43

2. 0.1 g (2.5%) of isomer B lower running spot on TLC in ethyl acetate, as a white powder, mp 139° C. An analytical sample of 3β-[(tert-butoxycarbonyl-amino)(tert-butoxycarbonylimino)methyl]amino}-4α-[(ethoxycarbonyl)(methyl-carbonylamino)methyl] cyclopentanone, isomer B, was prepared by recrystallization from ethyl acetate/hexane.

Analysis: Calculated for $C_{22}H_{36}N_4O_8$: C, 54.53; H, 7.49; N, 11.56 Found: C, 53.94; H, 7.44; N, 11.26

To a mixture of 2-trimethylsilyl-1,3-dithiane (0.67 g, 3.5 mmol) in tetrahydrofuran (6 mL) at 0° C. was added n-butyllithium (1.6 M, 2.5 mL, 3.7 mmol), and the mixture stirred at 0° C. for 0.75 h. After the mixture was cooled to −42° C., a mixture of 4β-{[(tert-butoxycarbonyl-amino)(tert-butoxycarbonylimino)methyl]amino}-4α-[(ethoxycarbonyl)(methylcarbonylamino)-methyl] cyclopentanone, mixture of isomers (0.24 g, 0.5 mmol), in tetrahydrofuran (4 mL) was added and the mixture further stirred at −42° C. for 2 h. The mixture was then quenched with saturated aqueous ammonium chloride (2 mL) and warmed to the room temperature. The organic layer was separated, water (5 mL) added to the aqueous phase and extracted with ethyl acetate (2×15 mL). The combined organic layers were washed with water (1×20 mL), brine (1×20 mL) and dried ($MgSO_4$). After filtration, the filtrate was concentrated and the residue passed through a column of silica gel (50 g) using ethyl acetate/hexane (1:2) as an eluent to give:

1. 0.15 g (50%) of isomer A, the higher running spot on TLC in ethyl acetate/hexane (1:2), as a white powder, mp 190–191° C. An analytical sample of 2-{3β-{[(tert-butoxycarbonylamino)(tert-butoxycarbonylimino)methyl]amino}4α-[(ethoxy-carbonyl)(methylcarbonylamino)methyl]cyclopentylidene}-1,3-dithiane, isomer A, was prepared by recrystallization from ethyl acetate/hexane.

Analysis: Calculated for $C_{26}H_{42}N_4O_7S_2$: C, 53.22; H, 7.21; N, 9.55 Found: C, 53.44; H, 7.27; N, 9.31

2. 0.06 g (20%) of isomer B, the lower running spot on TLC in ethyl acetate/hexane (1:2), as a white powder, mp 185–186° C. An analytical sample of 2-{3β-{[(tert-butoxycarbonylamino)(tert-butoxycarbonylimino)methyl]amino}-4α-[(ethoxy-carbonyl)(methylcarbonylamino)methyl]-1-cyclopentylidene}-1,3-dithiane, isomer B, was prepared by recrystallization from ethyl acetate/hexane.

Analysis: Calculated for $C_{26}H_{42}N_4O_7S_2$: C, 53.22; H, 7.21; N, 9.55 Found: C, 53.19; H, 7.20; N, 9.52

To a solution of 2-{3β-{[(tert-butoxycarbonylamino)(tert-butoxycarbonylimino)-methyl]amino}-4α-[(ethoxycarbonyl)(methylcarbonylamino)methyl] cyclopentylidene}-1,3-dithiane, isomer A (1.2 g; 2.0 mmol), in tetrahydrofuran (40 mL) was added dropwise under nitrogen lithium borohydride (Aldrich, 2M solution in tetrahydrofuran, 2.0 mL, 4.0 mmol) and lithium 9-borabicyclo[3.3.1]nonane hydride (Aldrich, 1M solution in tetrahydrofuran, 0.2 mL, 0.2 mmol) and the reaction mixture was stirred at room temperature overnight. An additional three portions of lithium borohydride (2M solution in tetrahydrofuran, 2.0 mL, 4.0 mmol) and lithium 9-borabicyclo[3.3.1]nonane hydride (1 M solution in tetrahydrofuran, 0.2 mL, 0.2 mmol) were added over a period of 36 h. The reaction was quenched with 1 N sodium hydroxide (10 mL), brine (10 mL) and stirred for 5 min. The reaction was acidified to pH 4 using glacial acetic acid, ether (20 mL) was added and the aqueous layer was separated. The aqueous layer was extracted with ether (2×20 mL), the organic layers were combined, dried and concentrated in vacuo to obtain crude. The crude was purified on a Chromatotron (50–100% ethyl acetate in hexane) to furnish 0.34 g (31%) of 2-{3β-{[(tert-butoxycarbonylamino)(tert-butoxycarbonylimino)methyl]amino}-4α-[(2-hydroxy)(1-methylcarbonylamino)ethyl]cyclopentylidene}-1,3-dithiane, isomer A, recrystallized from ether as a white solid, mp 209–210° C.

Analysis: Calculated for $C_{24}H_{40}N_4O_6S_2$: C, 52.92; H, 7.40; N, 10.29 Found: C, 53.03; H, 7.30; N, 10.19

To a solution of 2-{3β-{[(tert-butoxycarbonylamino)(tert-butoxycarbonylimino)-methyl]amino}-4α-[(2-hydroxy)(1-methlycarbonylamino)ethyl]cyclopentylidene}-1,3-dithiane, isomer A (0.23 g, 0.4 mmol), in methanol (6.7 mL) was added 6 N HCl (0.83 mL, 4.99 mmol) and stirred at room temperature until all starting material had disappeared (TLC analysis, ethyl acetate, ~3.0 h). The solvent was removed in vacuo (water bath temperature ~40° C.) to furnish crude 3β-{[(amino)(imino)methyl]amino}-4α-[(2-hydroxy)(1-methycarbonylamino)ethyl]-1-[(3-mercaptopropyl)-thiocarbonyl]cyclopentane {MS (ES+1) 363.5 [100%, (M+1)]}.

To the above crude was added water (1.4 mL) and conc ammonium hydroxide (1.4 mL) and the reaction was stirred for 3 h at room temperature. The solvent was removed in vacuo to furnish 0.6 g of the title compound mixed with salts, MS (ES+1) 272.4 [100%, (M+1)].

Example 7

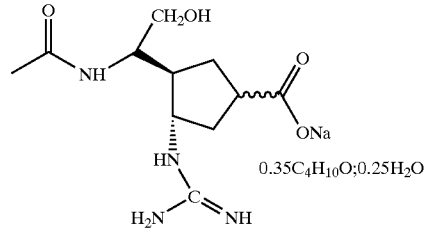

Sodium 3β-{[(amino)(imino)methyl]amino}-4α-[(2-hydroxy)(1-methylcarbonylamino)ethyl]-cyclopentan-r-carboxylate:diethylether:hydrate (12:4:3), isomer B To a solution of 2-{3β-{[(tert-butoxycarbonylamino)(tert-butoxycarbonylimino)-methyl]amino}-4α-[(ethoxycarbonyl)(methylcarbonylamino)methyl] cyclopentylidene}-1,3-dithiane from Example 6, isomer A (6.74 g, 11.5 mmol), in ethanol (57.5 mL) and tetrahydrofuran (115 mL) was added 1 N sodium hydroxide (23 mL, 23 mmol) and water (35 mL). The reaction was stirred at room temperature for 5 h. Tetrahydrofuran was removed in vacuo and the aqueous layer was washed with ethyl acetate (2×10 mL) and acidified to pH 5 with glacial acetic acid. The solid obtained was collected by filtration to furnish 5.95 g (93%) of 2-{3β-{[(tert-butoxycarbonylamino)(tert-butoxycarbonylimino)methyl]amino}-4α-[(carboxy)(methylcarbonyl-amino)methyl]-1-cyclopentylidene}-1,3-dithiane as a white solid.

Analysis: Calculated for $C_{24}H_{38}N_4O_7S_2 \cdot 0.5C_2H_6O \cdot 1H_2O$: C, 50.07; H, 7.23; N, 9.34 Found: C, 50.28; H, 6.85; N, 9.04

To a solution of the above acid (1.12 g, 2.0 mmol) in tetrahydrofuran (20 mL) cooled to 0° C. was added dropwise with stirring triethylamine (0.32 mL, 2.2 mmol) and ethyl chloroformate (0.21 mL, 2.1 mmol). The reaction mixture was stirred for 1 h at 0° C. The reaction was filtered through Celite and the cake was washed with tetrahydrofuran (2×5 mL). The filtrate was cooled to 0° C., sodium borohydride (powder, 0.23 g, 6.0 mmol) was added and methanol (1.3 mL) was then added dropwise over a period of 1 h. The reaction mixture was quenched with brine (10 mL) and acidified with glacial acetic acid to pH 5. Ether (10 mL) was added and the organic layer was separated. The aqueous layer was extracted with ether (2×10 mL). The organic layers were combined, dried and concentrated in vacuo to furnish 1.1 g (100%) of 2-{-3β{[(tert-butoxycarbonylamino)(tert-butoxycarbonylimino)methyl]amino}-4α-[(2-hydroxy)(1-methyl-carbonylamino)]-1-cyclopentylidene}-1,3-dithiane.

To a solution of above solid (3.67 g, 6.75 mmol) in dimethylformamide (16 mL) was added tert-butyldimethylchloro silane (1.15 g, 7.4 mmol) and imidazole (0.92 g, 13.5 mmol). The reaction mixture was stirred at room temperature overnight, poured into water (20 mL) and extracted with ether (3×20 mL). The organic layers were combined, washed with water (20 mL) and brine (25 mL), dried, and the solvent was removed in vacuo to furnish 4.4 g of a colorless oil. Purification of the crude by flash column chromatography (15–25% ethyl acetate in hexane) gave:

1. Isomer A, 2.5 g (57%) as a white solid, mp 129–130° C. (R$_f$=0.36, 25% ethyl acetate in hexane); MS (ES+) 444.9 [100%, (M+1)-tert-butyldimethylsilyl].

Analysis: Calculated for C$_{30}$H$_{54}$N$_4$O$_5$S$_2$Si: C, 54.68; H, 8.26; N, 8.50 Found: C, 54.71; H, 8.05; N, 8.61

2. Isomer B, 1.21 g (27%) of 2-{3β-{[(tert-butoxycarbonylamino)(tert-butoxy-carbonylimino)methyl]amino}-4α-[(2-tert-butyldimethylsilyloxy)(1-methycarbonylamino)ethyl]cyclopentylidene}-1,3-dithiane, isomer B, as a white solid mp 94–96° C., (R$_f$=0.28, 25% ethyl acetate in hexane); MS (ES+) 659.4 [100%, (M+1)].

Analysis: Calculated for C$_{30}$H$_{54}$N$_4$O$_5$S$_2$Si: C, 54.68; H, 8.26; N, 8.50 Found: C, 55.06; H, 8.18; N, 8.40

To a solution of 1.21 g (27%) of the above isomer B (1.11 g, 1.68 mmol), in methanol (50.4 mL), was added 6 N HCl (4.2 mL, 25.2 mmol) and the mixture was stirred at room temperature until all starting material had disappeared (TLC analysis, ethyl acetate, ~30 h). The solvent was removed in vacuo (water bath temperature ~35° C.) to furnish crude 3β-{[(tert-butoxycarbonylamino)(tert-butoxycarbonylimino)methyl]amino}-4α-[(2-hydroxy)(1-methyl-carbonylamino)ethyl]-1-[(3-mercaptopropyl)thiocarbonyl]cyclopentane {MS (ES+1) 563.5 [100%, (M+1)], 463.5 [80%, (M+1)-tert-butoxycarbonyl], 363.4 [50%, (M+1)-di-tert-butoxycarbonyl]}.

The above crude was dried in vacuo to remove trace amounts of water and then dissolved in dichloromethane (25 mL). Trifluoroacetic acid (1.29 mL, 16.8 mmol) was added and the mixture was stirred overnight at room temperature. The solvent was removed in vacuo to furnish a crude residue of 3β-[(amino)(imino)methyl]amino}-4α-[(2-hydroxy)(1-methylcarbonylamino)-ethyl]-1-[(3-mercaptopropyl)thiocarbonyl]cyclopentane {MS (ES+1) 363.4 [100%, (M+1)]}.

The above crude residue was dissolved in tetrahydrofuran (8.5 mL), methanol (4.2 mL) and 1 N sodium hydroxide (8.4 mL, 8.4 mmol) were added and the reaction mixture was stirred for 35 min at room temperature. Tetrahydrofuran and methanol were removed in vacuo and the aqueous layer was washed with ethyl acetate (2×10 mL). The aqueous layer was filtered and filtrate was acidified to pH 6.5 (1 N HCl). The acidified aqueous layer was washed with ethyl acetate (2×10 mL) and concentrated in vacuo to furnish 1.3 g of crude.

The above crude (1.0 g) was loaded on a silica gel column (50 g) and eluted with chloroform:methanol:conc ammonium hydroxide (5:4:1) (1000 mL) to remove organic and inorganic impurities. The column was then eluted with 25% water in 2-propanol to furnish 0.21 g (43%) of an oil. The oil was triturated with ethanol/ether and ether (5×10 mL) to furnish the title compound as a white solid, mp 65° C. (fuses) (R$_f$=0.36, 25% water in 2-propanol, TLC plate developed with KMnO$_4$ spray).

Analysis: Calculated for C$_{11}$H$_{19}$N$_4$NaO$_4$.0.35C$_4$H$_{10}$O.0.25H$_2$O: C, 45.86; H, 7.14; N, 17.25 Found: C, 46.14; H, 7.50; N, 17.55

Example 8

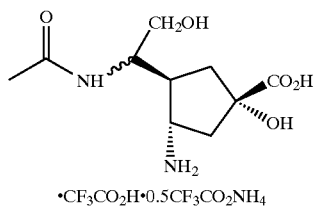

•CF$_3$CO$_2$H•0.5CF$_3$CO$_2$NH$_4$ t-3-Amino-t-1-hydroxy-c-4-[(hydroxymethyl)(methylcarbonylamino)methyl]cyclopentan-r-carboxylic acid trifluoroacetic acid ammonium trifluoroacetate (1:1:0.5)

A mixture of trans-3-azido-4-[bis(ethoxycarbonyl)(methylcarbonylamino)methyl]-cyclopentanone (from Example 6, 0.50 g, 1.5 mmol), di-tert-butyl dicarbonate (Aldrich, 0.39 g, 1.77 mmol), and Pd/C, 10% (0.140 g) in ethyl acetate (25 mL) was hydrogenated at 45 psi for 1 h. The catalyst was removed by filtration and the filtrate was concentrated in vacuo to afford 0.69 g of crude. Purification by flash column chromatography (silica gel, 75% ethyl acetate/hexanes) gave a semisolid. Recrystallization of the residue from ether/hexanes provided 0.275 g (45%) of trans-3-tert-butyloxycarbonylamino-4-[bis(ethoxycarbonyl)(methylcarbonylamino)methyl]cyclo-pentanone as a white solid, mp 135–136° C.

Analysis: Calculated for C$_{19}$H$_{30}$N$_2$O$_4$: C, 55.06; H, 7.30; N, 6.76 Found: C, 54.63; H, 7.17; N, 6.74

To a stirred solution of bis-(phenylthio)methane (Aldrich, 1.12 g, 4.84 mmol) tetrahydrofuran (10 mL) at 0° C. was added dropwise n-butyllithium (1.6M, 3.0 mL, 4.84 mmol). After 30 min of stirring, the reaction mixture was cooled to −78° C. and trans-3-tert-butyloxycarbonylamino-4-[bis(ethoxycarbonyl)(methylcarbonylamino)methyl]cyclopentanone (0.50 g, 1.2 mmol) in tetrahydrofuran (6 mL) was added dropwise. The reaction mixture was stirred for 1 h then quenched with a saturated aqueous solution of ammonium chloride (10 mL). The separated aqueous layer was extracted with ether (4×10 mL). The combined organic extracts were washed with brine, dried (MgSO$_4$), filtered through Celite, and concentrated in vacuo to provide 1.25 g of crude. Purification by flash column chromatography (silica gel, 75 g, 25% ethyl acetate/hexanes) gave 0.16 g (20%) of c-3-(tert-butoxycarbonylamino)-t-4-[bis(ethoxycarbonyl)(methylcarbonylamino)methyl]-t-1-[bis-(phenylthio)methyl]cyclopentan-r-1-ol as a white solid, mp 36–37° C.

Analysis:

Calculated for C$_{32}$H$_{42}$N$_2$O$_8$S$_2$: C, 59.42; H, 6.54; N, 4.33 Found: C, 59.64; H, 6.45; N, 3.94

A mixture of c-3-(tert-butoxycarbonylamino)-t-4-[bis(ethoxycarbonyl)(methylcarbonyl-amino)methyl]-t-1-[bis- (phenylthio)methyl]cyclopentan-r-1-ol (0.63 g, 0.97 mmol) and potassium hydroxide (1 N, 3.4 mL, 3.4 mmol) in a 50% aqueous solution of ethanol (24 mL) was stirred at room temperature for 12 h. The reaction mixture was concentrated in vacuo and the resulting residue was dissolved in ethyl acetate (12 mL). This reaction mixture was heated at reflux for 1 h and allowed to cool to room temperature. To this reaction mixture was added glacial acetic acid (0.2 mL, 3.4 mmol). The separated aqueous layer was extracted with ethyl acetate (4×10 mL). The combined organic extracts were washed with brine, dried ($MgSO_4$), filtered through Celite, and concentrated in vacuo to provide 0.54 g of crude. Purification by radial PLC (silica gel, 25–50% ethyl acetate/hexanes) gave 0.35 g (63%) of c-3-(tert-butoxycarbonylamino)-t-4-[(ethoxy-carbonyl)(methylcarbonylamino)methyl]-t-1-[bis-(phenylthio)methyl]cyclopentan-r-1-ol as a white solid, mp 58–59° C.

Analysis: Calculated for $C_{29}H_{38}N_2O_6S_2$: C, 60.60; H, 6.66; N, 4.87 Found: C, 60.76; H, 6.79; N, 4.88

To a stirred solution of c-3-(tert-butoxycarbonylamino)-t-4-[(ethoxycarbonyl)-(methylcarbonylamino)methyl]-t-1-[bis-(phenylthio)methyl]cyclopentan-r-1-ol (0.17 g, 0.29 mmol) in tetrahydrofuran (7 mL) at room temperature was added lithium borohydride (2 M, 0.3 mL, 0.6 mmol). After 12 h of stirring, the reaction mixture was heated at 50° C. for 45 min. To this reaction mixture was added 1 N HCl (6 mL). The separated aqueous layer was extracted with ethyl acetate (4×5 mL). The combined organic extracts were washed with brine, dried ($MgSO_4$), filtered through Celite, and concentrated in vacuo to provide 0.16 g of crude. Purification by radial PLC (silica gel, 50% ethyl acetate/hexanes) gave 0.08 g (50%) of c-3-(tert-butoxycarbonyl-amino)-t-4-[(2-hydroxy)(1-methylcarbonylamino)ethyl]-t-1-[bis(phenylthio)methyl]cyclo-pentan-r-1-ol (isomer A) as a white solid, mp 66–67° C.

Analysis: Calculated for $C_{27}H_{36}N_2O_5S_2$: C, 60.88; H, 6.62; N, 5.26 Found: C, 60.95; H, 6.94; N, 5.14

To a stirred solution of c-3-(tert-butoxycarbonylamino)-t-4-[bis(ethoxycarbonyl)-(methylcarbonylamino)methyl]-t-1-[bis-(phenylthio)methyl]cyclopentan-r-1-ol (0.76 g, 1.2 mmol) in tetrahydrofuran (10 mL) at room temperature was added lithium borohydride (0.03 g, 1.4 mmol). The reaction mixture was heated at reflux for 12 h and allowed to cool to room temperature. To this reaction mixture was added 1 N HCl (10 mL). The separated aqueous layer was extracted with ether (4×10 mL). The combined organic extracts were washed with brine, dried ($MgSO_4$), filtered through Celite, and concentrated in vacuo to provide 0.54 g of crude. Purification by radial PLC (silica gel, 70% ethyl acetate/hexanes) gave 0.15 g (21%) of c-3-(tert-butoxycarbonylamino)-t-4-[(2-hydroxy)(1-methylcarbonylamino)ethyl]-t-1-[bis-(phenylthio)-methyl]cyclopentan-r-1-ol (isomer B) as a white solid, mp 176–177° C.

Analysis: Calculated for $C_{27}H_{36}N_2O_5S_2$: C, 60.88; H, 6.62; N, 5.26 Found: C, 60.85; H, 6.72; N, 5.03

To a stirred solution of a mixture of isomers A and B of c-3-(tert-butoxycarbonylamino)-t-4-[(2-hydroxy)(1-methylcarbonylamino)ethyl]-t-1-[bis-(phenylthio)methyl] cyclopentan-r-1-ol (5.65 g, 10.6 mmol) in dimethylformamide (100 mL) at −23° C. was added sodium hydroxide (95%, 0.345 g, 13.8 mmol) and tetrabutylammonium iodide (0.40 g, 1.1 mmol). After 30 min of stirring, benzyl bromide (2.0 mL, 15.8 mmol) was added dropwise. The reaction mixture was stirred at −23° C. for 3 h then quenched with glacial acetic acid (2.5 mL) and water (100 mL). The separated aqueous layer was extracted with ethyl acetate (7×15 mL). The combined organic extracts were washed with brine, dried ($MgSO_4$), filtered through Celite, and concentrated in vacuo to provide 9.1 g of crude. Purification by flash column chromatography (silica gel, 210 g, 50–75% ethyl acetate/hexanes) gave 2.98 g (45%) of c-3-(tert-butoxycarbonylamino)-t-4-[(1-methylcarbonyl-amino)(2-phenylmethoxy)ethyl]-t-1-[bis-(phenylthio)methyl]cyclopentan-r-1-ol as a white solid, mp 52–54° C.

Analysis: Calculated for $C_{34}Hl_{42}N_2O_5S_2$: C, 65.57; H, 6.79; N, 4.49 Found: C, 65.52; H, 6.80; N, 4.45

A mixture of c-3-(tert-butoxycarbonylamino)-t-4-[(1-methylcarbonylamino)(2-phenyl-methoxy)ethyl]-t-1-[bis-(phenylthio)methyl]cyclopentan-r-1-ol (2.53 g, 4.1 mmol), mercuric oxide (1.90 g, 8.8 mmol), and boron trifluoride etherate (1.1 mL, 8.9 mmol) in a 15% aqueous solution of tetrahydrofuran (70 mL) was stirred at room temperature for 2 h. The reaction mixture was filtered through a pad of Celite and Florisil. The filtrate was concentrated in vacuo to give 2.74 g of the crude. To the above crude in methanol (50 mL) was added iodine (1.9 g, 7.5 mmol) and the reaction mixture was heated to 50° C. To this mixture was added dropwise a solution of potassium hydroxide (0.71 M/methanol, 50 mL, 35.7 mmol). After 2 h stirring at 50° C., the reaction mixture was filtered through Celite. The filtrate was concentrated in vacuo and the resulting residue was dissolved in ethyl acetate (30 mL) and water (20 mL). The layers were separated and the aqueous layer was extracted with ethyl acetate (4×10 mL). The combined organic extracts were washed with brine, dried ($MgSO_4$), filtered through Celite, and concentrated in vacuo to provide 3.6 g of crude. Purification by flash column chromatography (silica gel, 200 g, 50–100% ethyl acetate/hexanes) gave 0.224 g (14%) of the desired hydroxyacid as a white solid. To a solution of hydroxyacid (0.244 g, 0.56 mmol) in dichloromethane (15 mL) was added trifluoroacetic acid (0.86 mL, 11.2 mmol) and the reaction mixture was stirred at room temperature for 12 h. The reaction mixture was concentrated in vacuo to give crude. Purification by flash column chromatography (silica gel, 60 g, chloroform/methanol/ammonium hydroxide: 80/18/2) gave 0.241 g of a thick, yellow oil. Trituration of the yellow oil with ether provided 0.185 g (51%) of t-3-amino-c-4-[(1-methylcarbonylamino)(2-phenylmethoxy) ethyl]-t-1-hydroxycyclopentan-r-carboxylic acid as a tan solid, mp 37–39° C.

Analysis: Calculated for $C_{17}H_{24}N_2O_5 \cdot C_2HF_3O \cdot 1.5C_2H_4F_3NO_2$: C, 40.84; H, 4.83; N, 7.58 Found: C, 40.86; H, 5.08; N, 7.90

A mixture of t-3-amino-c-4-[(1-methylcarbonylamino)(2-phenylmethoxy)ethyl]-t-1-hydroxycyclopentan-r-carboxylic acid (0.09 g, 0.14 mmol) and Palladium hydroxide (0.15 g) in ethanol (20 mL) was hydrogenated at 40 psi overnight. The reaction mixture was filtered through Celite and the filtrate was concentrated in vacuo to give 0.078 g of crude. A mixture of the above crude amine and trifluoroacetic acid (0.2 mL, 2.6 mmol) in dichloromethane (10 mL) was stirred overnight. The mixture was concentrated in vacuo to give 0.08 g of a brown solid which was triturated with ether to provide 0.045 g (75%) of the title compound as a tan solid, mp 83–85° C.

Analysis: Calculated for $C_{10}H_{18}N_2O_5 \cdot C_2HF_3O_2 \cdot 0.5C_2H_4F_3NO_2$: C, 36.67; H, 4.97; N, 8.22 Found: C, 36.40; H, 5.15; N, 7.95

Example 9

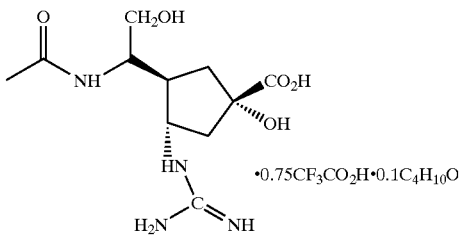

t-3-{[(Amino)(imino)methyl]amino}-t-1-hydroxy-c-4-[(2-hydroxymethyl)(1-methylcarbonyl-amino)ethyl] cyclopentan-r-carboxylic acid trifluoroacetic acid diethyl ether [20:15:2] (isomer A at C-6)

To tris(methylthio)methane (21.27 g, 138 mmol) in tetrahydrofuran (350 mL) at −78° C. was added dropwise over a period of 10 min under nitrogen n-butyllithium (1.6 M solution in hexane, 90 mL, 144 mmol) and stirred at −78° C. for 40 min. To the anion at −78° C. was added a solution of 3β-(tert-butoxycarbonylamino)-4α-[(ethoxycarbonyl) (methylcarbonylamino)methyl]-cyclopentanone from Example 6 (isomer A, 8.34 g, 17.23 mmol) in tetrahydrofuran (50 mL) over a period of 10 min and the reaction mixture stirred at −78° C. for 1.5 h. The reaction was quenched with saturated ammonium chloride (50 mL) and warmed to room temperature, ether (50 mL), added and the organic layer was separated. The aqueous layer was extracted with ether (2×50 mL), the organic layers were combined, dried over MgSO$_4$ and concentrated in vacuo to furnish an oil. The crude oil was dissolved in ethyl acetate (50 mL) and hexane (400 mL) and stored overnight in a freezer. A crystalline solid was removed by filtration. The mother liquor was purified by flash column chromatography (silica gel, 240 g, 30–45% ethyl acetate in hexane) to obtain 2.7 g (24%) of 3β-{[(tert-butoxycarbonylamino)(tert-butoxycarbonylimino)methyl]amino}-4α-[(ethoxycarbonyl)(methylcarbonylamino)methyl]-1-[(trismethythio)methyl]cyclopentanol as a mixture of isomers.

To a solution of above mixture (2.69 g, 4.22 mmol) in tetrahydrofuran (42 mL) was added dropwise under nitrogen lithium borohydride (0.74 g, 33.73 mmol) and lithium 9-borabicyclo[3.3.1]nonane hydride (1 M solution in tetrahydrofuran, 0.84 mL, 0.84 mmol) and the reaction mixture was stirred at room temperature overnight. The reaction was quenched with 1 N sodium hydroxide (1 mL), brine (20 mL) and stirred for 5 min. The reaction was acidified to pH 4 using glacial acetic acid. Ether (10 mL) was added and the aqueous layer was separated. The aqueous layer was neutralized with saturated aqueous sodium bicarbonate and extracted with ethyl acetate (2×10 mL), the organic layers were combined, dried and concentrated in vacuo to obtain 3.3 g of a yellow oil. The oil was purified by flash column chromatography [silica gel (200 g), 10% chloroform:methanol:conc ammonium hydroxide (80:18:2) in dichloromethane] to furnish 1.5 g (60%) of t-3-{[(tert-butoxycarbonylamino)(tert-butoxycarbonylimino)methyl]amino}-c-4-[(2-hydroxy)(1-methylcarbonylamino)ethyl]-t-1-[tris(methylthio)methyl]cyclopentan-r-ol, a white solid [R$_f$=0.17, 20% chloroform:methanol:conc ammonium hydroxide (80:18:2) in dichloromethane].

To a mixture of above solid (1.2 g, 2.0 mmol), mercuric chloride (2.02 g, 7.45 mmol) and mercuric oxide (0.65 g, 3.02 mmol) was added methanol/water (46.2/3.8 mL) and the reaction mixture was stirred at room temperature for 30 min. The mixture was filtered through a pad of Celite and Florisil (20 g). The cake was washed with methanol (20 mL) and the filtrate concentrated in vacuo to furnish 2.1 g of white semisolid. The crude was purified by flash column chromatography [silica gel (60 g); 75% ethyl acetate in hexane and 10% methanol in ethyl acetate] to furnish 0.55 g (55%) of methyl t-4-{[(tert-butoxycarbonylamino)(tert-butoxycarbonylimino)methyl]amino}-c-3-[(2-hydroxymethyl)(1-methylcarbonylamino)ethyl]-t-1-hydroxycyclopentan-r-carboxylate as a white solid, mp 94–96° C.

To a solution of above solid (0.47 g, 0.93 mmol) in tetrahydrofuran (9.3 mL) was added 1 N sodium hydroxide (1.86 mL, 1.86 mmol) and water (7.4 mL). The reaction mixture was stirred at room temperature for 1 h. Tetrahydrofuran was removed in vacuo and the aqueous layer was washed with ether (2×10 mL). The aqueous layer was made acidic with glacial acetic acid (pH=5), saturated with sodium chloride and extracted with ethyl acetate (3×15 mL). The organic layers were combined and concentrated in vacuo to furnish 0.33 g (73%) of crude which was triturated with ether/hexane to furnish t-3-{[(tert-butoxycarbonylamino)(tert-butoxycarbonylimino)methyl]amino}-t-1-hydroxy-c-4-[(2-hydroxymethyl)(1-methylcarbonylamino)ethyl]cyclopentan-r-carboxylic acid (isomer A) as a white solid, mp 238–240° C.

Analysis: Calculated for $C_{21}H_{36}N_4O_9$: C, 51.63; H, 7.43; N, 11.47 Found: C, 51.31; H, 7.48; N, 11.07

To a solution of t-3-{[(tert-butoxycarbonylamino)(tert-butoxycarbonylimino)-methyl]amino}-t-1-hydroxy-c-4-[(hydroxymethyl)(methylcarbonylamino)methyl] cyclopentan-r-carboxylic acid, isomer A (0.2 g, 0.41 mmol), in dichloromethane (10 mL), trifluoroacetic acid (0.63 mL, 8.2 mmol) was added and the reaction was stirred at room temperature overnight. Additional trifluoroacetic acid (0.32 mL, 4.1 mmol) was added and the reaction was stirred at room temperature for 1 h. The solvent was removed in vacuo and traces of excess trifluoroacetic acid were removed in vacuo by co-distilling the residue twice with dichloromethane (10 mL). The residue

Example 10

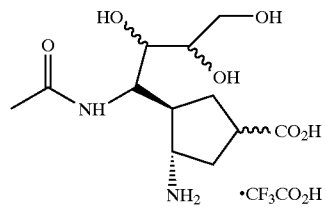

3β-amino-4α-[(1-methylcarbonylamino)(2,3,4-trihydroxy)butyl]cyclopentancarboxylic acid trifluoroacetic acid (1:1) (isomer A at C-6)

To 2-trimethylsilyl-1,3-dithiane (Aldrich, 7.88 g, 41.5 mmol) in tetrahydrofuran (100 mL) at 0° C. was added dropwise over a period of 10 min under nitrogen n-butyllithium (1.6 M solution in hexane, 28.6 mL, 45.7 mmol) and stirred at 0° C. for 45 min. The anion was cooled to −40° C. and a solution of 3β-(tert-butoxycarbonylamino)-4α-[bis(ethoxycarbonyl)(methylcarbonyl-amino)methyl] cyclopentanone (from Example 8, 4.3 g, 10.4 mmol) in tetrahydrofuran (50 mL) was then added dropwise over a period of 15 min. The reaction mixture was stirred at −40° C. for 5 h and warmed to −20° C. The reaction was quenched with saturated ammonium chloride (50 mL) and warmed to room temperature. Ether (20 mL) was added and the organic layer was separated. The aqueous layer was extracted with ether (2×25 mL), the organic layers were combined, dried over $MgSO_4$ was dissolved in water (5 mL) and concentrated in vacuo to furnish an oily residue which was triturated with ether to obtain 0.13 g (83%) of the title compound as a white solid, mp 162–166° C.

Analysis: Calculated for $C_{13}H_{19}F_3N_4O_9 \cdot 0.75C_2HF_3O_2 \cdot 0.1C_4H_{10}O$: C, 40.64; H, 5.75; N, 14.70 Found: C, 40.77; H, 5.80; N, 14.67 and concentrated in vacuo to furnish crude. Purification of the crude by flash column chromatography (silica gel, 320 g, 30–35% ethyl acetate in hexane) gave 3.16 g (59%) of 2-{3β-(tert-butoxycarbonylamino)-4α-[bis(ethoxycarbonyl)(methylcarbonylamino)methyl]cyclopentyl-idine}-1,3-dithiane as a colorless oil that solidified on drying in vacuo at acetone reflux temperature to give a solid, mp 66–68° C.

Analysis: Calculated for $C_{23}H_{36}N_2O_7S_2$: C, 53.47; H, 7.02; N, 5.42 Found: C, 53.50; H, 7.07; N, 5.41

To a solution of 2-{3β-(tert-butoxycarbonylamino)-4α-[bis(ethoxycarbonyl)(methyl-carbonylamino)methyl]cyclopentylidene}-1,3-dithiane (7.5 g, 14.53 mmol) in ethanol (75 mL) was added 1 N sodium hydroxide (50.9 mL, 50.9 mmol) and water (25 mL) and the reaction mixture was heated at reflux for 2 h. The reaction was cooled, glacial acetic acid (4.6 mL, 76.3 mmol) was added, the mixture heated at gentle reflux for 1 h and stirred at room temperature overnight. The solid that separated was collected by filtration, washed with water and dried in vacuo at toluene reflux temperature to furnish 1.63 g (27%) of solid. The filtrate was extracted with ethyl acetate (3×100 mL), the organic layers combined, dried and concentrated in vacuo to furnish 3.5 g of residue. An analytical sample was prepared by crystallization of the combined solid from ethanol to furnish 5.1 g (85%) of 2-{3β-(tert-butoxycarbonylamino)-4α-[(carboxy)(methylcarbonyl-amino)methyl]cyclopenylidiene}-1,3-dithiane as a white solid mp 174–176° C.

Analysis: Calculated for $C_{18}H_{28}N_2O_5S_2 \cdot 0.75H_2O$: C, 50.27; H, 6.91; N, 6.51 Found: C, 50.03; H, 6.54; N, 6.41

To a solution of 2-{3β-(tert-butoxycarbonylamino)-4α-[(carboxy)(methylcarbonyl-amino)methyl]cyclopentylidene}-1,3-dithiane (5.13 g, 12.3 mmol) in tetrahydrofuran (120 mL) cooled to 0° C. was added methyl chloroformate (1 mL, 13.5 mmol) and triethylamine (2.2 mL, 15.4 mmol). The reaction mixture was stirred at 0° C. for 40 min and a cold solution of N,O-dimethylhydroxylamine hydrochloride (1.84 g, 18.5 mmol) and triethylamine (3.5 mL, 24.6 mmol) in tetrahydrofuran (5 mL) that had been stirred at 0° C. for 30 min was added. The reaction mixture was allowed to warm to room temperature and stirred overnight. The reaction was filtered through Celite and the cake washed with tetrahydrofuran (10 mL). To the filtrate was added a cold solution of N,O-dimethylhydroxylamine hydrochloride (1.84 g, 18.5 mmol) and triethylamine (3.5 mL, 24.66 mmol) in tetrahydrofuran (5 mL) that had been stirred at 0° C. for 30 min and again stirred overnight at room temperature. The solvent was removed in vacuo and to the residue sodium hydroxide (0.1M, 100 mL) and ethyl acetate (100 mL) were added. The organic layer was separated and the aqueous layer was extracted with ethyl acetate (2×75 mL). The organic layers were combined and washed with brine (100 mL), dried and concentrated in vacuo to furnish 4.73 g crude amide as a semisolid. Purification of the crude by flash column chromatography [200 g silica gel, 90% ethyl acetate in hexane and 25% chloroform/methanol/ammonium hydroxide (80:18:2) in methylene chloride] gave 4.2 g (74%) of 2-{3β-(tert-butoxycarbonylamino)-4α-{(methylcarbonylamino){[(methyl)(methoxy)amino]carbonyl}methyl}cyclopentylidene}-1,3-dithiane. An analytical sample, mp 122–126° C., was prepared as a white solid by recrystallization from ether/hexane.

Analysis: Calculated for $C_{20}H_{33}N_3O_5S_2$: C, 52.26; H, 7.24; N, 9.14 Found: C, 52.34; H, 7.20; N, 9.09

To a solution of 2-{3β-(tert-butoxycarbonylamino)-4α-{(methylcarbonylamino)-{[(methyl)(methoxy)amino]carbonyl}methyl}cyclopentylidene}-1,3-dithiane (0.26 g, 0.57 mmol) in tetrahydrofuran (2.5 mL) cooled to 0° C. was added dropwise lithium tri-tert-butoxyaluminohydride (Aldrich, 1.0 M solution in tetrahydrofuran, 1.4 mL, 1.4 mmol). The reaction mixture was stirred at room temperature overnight. The reaction was quenched carefully with 1 N HCl (1.0 mL, pH should not go below 4.0) and stirred for 5 min. Ether (20 mL) and 1.0 M aqueous solution of sodium potassium tartrate salt (10 mL) was added and reaction mixture was stirred at room temperature for 30 min. The organic layers were separated and aqueous layer was extracted with ether (2×10 mL). The organic layers were combined, washed with brine (20 mL) dried and concentrated in vacuo to furnish 0.3 g of a white solid. Purification of the crude by flash column chromatography (20 g silica gel, 50–80% ethyl acetate in hexane) gave two isomers (at C-6) of 2-{3β-(tert-butoxycarbonylamino)-4α-[(formyl)(methylcarbonylamino)methyl]cyclopentylidene}-1,3-dithiane:

1. 0.09 g (40%) of isomer A at C-6, a white solid, mp 188–192°0 C. (dec).

Analysis: Calculated for $C_{18}H_{28}N_2O_4S_2$: C, 53.97; H, 7.05; N, 6.99 Found: C, 53.93; H, 7.09; N, 6.93

2. 0.08 g (35%) of isomer B at C-6, a white solid, mp >180° C. (dec).

Analysis: Calculated for $C_{18}H_{28}N_2O_4S_2$: C, 53.97; H, 7.05; N, 6.99 Found: C, 54.03; H, 7.05; N, 6.97

To a solution of 2-{3β-(tert-butoxycarbonylamino)-4α-[(formyl)(methylcarbonyl-amino)methyl]cyclopentylidene}-1,3-dithiane (0.17 g, 0.43 mmol) in tetrahydrofuran (5 mL) cooled to –78° C. was added dropwise vinylmagnesium bromide (Aldrich, 1.0 M solution in tetrahydrofuran, 2.2 mL, 2.2 mmol) and stirred at –78° C. for 2 h. The reaction was quenched carefully with saturated aqueous ammonium chloride (5.0 mL). Ether (10 mL) and brine (5 mL) were added and the reaction mixture was allowed to warm to room temperature. The organic layers were separated and the aqueous layer was extracted with ether (2×10 mL). The organic layers were combined, washed with brine (20 mL) dried and concentrated in vacuo to furnish 0.17 g crude as a white solid. Purification of the crude by flash column chromatography (10 g silica gel, 50–100% ethyl acetate in hexane) gave 0.06 g (33%) of 2-{3β-(tert-butoxycarbonylamino)-4α-[(2-hydroxy)(1-methylcarbonylamino)-3-butenyl]cyclopentylidene}-1,3-dithiane (isomer A at C-6) as a white solid, mp >210° C. (dec).

Analysis: Calculated for $C_{20}H_{32}N_2O_4S_2$: C, 56.05; H, 7.53; N, 6.54 Found: C, 56.18; H, 7.50; N, 6.47

To a solution of 2-{3β-(tert-butoxycarbonylamino)-4α-[(2-hydroxy)(1-methylcarbonyl-amino)-3-butenyl]cyclopentylidene}-1,3-dithiane (isomer A, 0.55 g, 1.28 mmol) in methanol (19.3 mL) was added 6 N HCl (3.2 mL, 19.28 mmol) and the mixture was stirred at room temperature until all starting material had disappeared (TLC, ethyl acetate and MS analysis ~20 h). The reaction mixture was cooled to 0° C. and sodium hydroxide (1.02 g, 25.7 mmol) was added and the reaction was stirred at room temperature for 1 h. The reaction was quenched with glacial acetic acid (0.8 mL, 12.85) and concentrated in vacuo to furnish crude residue. To the residue was added ethyl acetate (10 mL) and water (10 mL). The aqueous layer was separated and extracted with ethyl acetate (2×10 mL). The organic layers were combined and concentrated in vacuo to furnish 0.4 g of crude.

The above crude was dissolved in anhydrous methanol (20 mL) and cooled to 0° C. A solution of dry HCl in ether (Aldrich, 1.0 M solution, 5 mL) was added and the reaction mixture was stirred overnight. The reaction was quenched with 1 N sodium hydroxide in methanol to adjust the pH of the reaction to 6–7, and concentrated in vacuo to obtain crude residue. The residue was dissolved in water (10 mL) and extracted with dichloromethane (3×10 mL). The organic layers were combined, dried and concentrated in vacuo to obtain 0.2 g of crude. The crude was purified by flash column chromatography [10–50% chloroform:methanol::conc ammonium hydroxide (80:18:2) in dichloromethane] to furnish 0.12 g (24%) of methyl 3β-(tert-butoxycarbonylamino)-4α-[(2-hydroxy)(1-methylcarbonylamino)-3-butenyl]cyclopentan-carboxylate (isomer A at C-6) as an oil, MS (ES+) 371.4 [100%, (M+1)] and 353.4 [100%, (M+1)–$H_2O$].

The above oil (0.1 g, 0.27 mmol) was dissolved in tetrahydrofuran/tert-butanol (2 mL, 1:1) and N-methyl morpholine oxide (50 mg), osmium tetraoxide (0.05 wt % in tert-butanol, 0.2 mL) and water (1 mL) was added. The reaction mixture was stirred overnight at room temperature. A saturated aqueous solution of sodium sulfite (2 mL) was added and stirred vigorously for 30 min. Brine (2 mL) was added the aqueous layer was extracted with ethyl acetate (3×10 mL). The organic layers were combined, dried and concentrated in vacuo to obtain 0.1 g of crude. The crude was purified by flashcolumn chromatography [0, 5, 10, 50, 100% methanol in ethyl acetate] to furnish 0.06 g (59%) of triol as a semisolid, MS (ES+) 405.4 [100%, (M+1)] and 387.5 [60%, (M+1)–$H_2O$]. To a solution of the above solid (0.06 g, 0.16 mmol) in tetrahydrofuran (1.6 mL) was added 1 N sodium hydroxide (1.0 mL, 1.0 mmol) and stirred at room temperature for 1.5 h. Ether (5 mL) and water (1 mL) were added, and organic layers were separated. The aqueous layer was washed with ethyl acetate (2×5 mL). The aqueous layer was then acidified to pH 5-4 using 1 N HCl, saturated with sodium chloride and extracted with ethyl acetate (3×5 mL. The organic layers were combined, dried and concentrated in vacuo to furnish 0.027 g (43%) of 3β-(tert-butoxycarbonylamino)-4α-[(1-methylcarbonylamino)(2,3,4-trihydroxy)butyl]cyclopentancarboxylic acid (isomer A at C-6) as a white solid, MS (ES+) 391.4 [55%, (M+1)], 373.6 [40% (M+1)–$H_2O$] and 100% 317.3 [(M+1)-tert-butyl].

To a solution of above acid (0.027 g, 0.07 mmol) in dichloromethane (1.0 mL) was added trifluoroacetic acid (0.11 mL, 1.4 mmol), and the reaction was stirred at room temperature overnight. Additional trifluoroacetic acid (0.11 mL, 1.4 mmol) was added and the reaction was stirred at room temperature for 1 h. The solvent was removed in vacuo and traces of trifluoroacetic acid were removed in vacuo by co-distilling the residue twice with dichloromethane (10 mL). The residue was dissolved in water (0.5 mL), concentrated in vacuo and dried at acetone reflux temperature in vacuo to obtain 0.017 g (60%) of the title compound (isomer A) as a tan solid, MS (ES+) 291.4 [100%, (M+1)].

Example 11

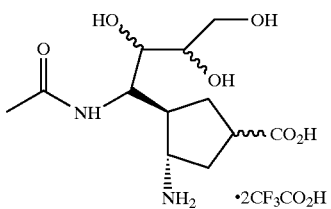

3β-amino-4α-[(1-methylcarbonylamino)(2,3,4-trihydroxy)butyl]cyclooentancarboxylic acid trifluoroacetic acid (1:2) (isomer B at C-6)

To a solution of 2-{3β-(tert-butoxycarbonylamino)-4α-[(formyl)(methylcarbonyl-amino)methyl]cyclopentylidene}-1,3-dithiane (isomer B at C-6), from Example 10 (0.45 g, 1.13 mmol) in tetrahydrofuran (20 mL) cooled to –78° C. was added dropwise vinylmagnesium bromide (Aldrich, 1.0 M solution in tetrahydrofuran, 5.6 mL, 5.6 mmol) and stirred at –78° C. for 1 h. The reaction was quenched carefully with saturated aqueous ammonium chloride (5.0 mL). Ether (20 mL) and brine (5 mL) were added and the reaction mixture was allowed to warm to room temperature. The organic layers were separated and the aqueous layer was extracted with ether (2×10 mL). The organic layers were combined, washed with brine (20 mL), dried and concentrated in vacuo to furnish 0.5 g of a white solid. Purification by flash column chromatography (10 g silica gel, 60–100% ethyl acetate in hexane) gave 0.21 g (44%) of 2-{3β-(tert-butoxycarbonylamino)-4α-[(2-hydroxy)(1-methylcarbonylamino)-3-butenyl]cyclopentylidene}-1,3-dithiane (isomer B at C-6) as a white solid, mp >210° C. (dec).

Analysis: Calculated for $C_{20}H_{32}N_2O_4S_2 \cdot 0.25H_2O$: C, 55.46; H, 7.56; N, 6.47 Found: C, 55.20; H, 7.47; N, 6.41

To a solution of 2-{3β-(tert-butoxycarbonylamino)-4α-[(2-hydroxy)(1-methylcarbonyl-amino)-3-butenyl]cyclopentylidene}-1,3-dithiane (isomer B at C-6) (0.58 g, 1.36 mmol) in methanol (21 mL) was added 6 N HCl (3.4 mL, 20.46 mmol) and the mixture was stirred at room temperature until all starting material had disappeared (~20 h). The reaction mixture was cooled to 0° C. and sodium hydroxide (1.1 g, 27.6 mmol) was added and the reaction was stirred at room temperature for 1 h. The reaction was quenched with glacial acetic acid (0.83 mL, 13.79 mmol) and concentrated in vacuo. To the residue obtained was added ethyl acetate (10 mL) and water (10 mL). The aqueous layer was separated and extracted with ethyl acetate (2×10 mL). The organic layers were combined and concentrated in vacuo to furnish 0.41 g of residue.

The above crude was dissolved in anhydrous methanol (20 mL) and cooled to 0° C. A solution of dry HCl in ether (Aldrich, 1.0M solution, 5 mL) was added and the reaction mixture was stirred overnight. The reaction was quenched with 1 N sodium hydroxide in methanol to adjust pH of the reaction to 6–7 and then concentrated in vacuo. The residue was dissolved in water (10 mL) and extracted with dichloromethane (3×10 mL). The organic layers were combined, dried and concentrated in vacuo to obtain 0.17 g of crude. The crude was purified by flash column chromatography [10–50% chloroform:methanol:conc ammonium hydroxide (80:18:2) in dichloromethane] to furnish 0.14 g (28%) of methyl 3β-(tert-butoxycarbonylamino)-4α-[(2-hydroxy)(1-methylcarbonylamino)-3-butenyl]cyclopentancarboxylate (isomer B at C-6) as an oil, MS (ES+) 371.4 [90%, (M+1)].

The above oil (0.12 g, 0.32 mmol) was dissolved in tetrahydrofuran/tert-butanol (2 mL, 1:1) and N-methylmorpholine oxide (50 mg), osmium tetraoxide (0.05 wt % in tert-butanol, 0.2 mL) and water (1 mL) was added. The reaction mixture was stirred overnight at room temperature. A saturated aqueous solution of sodium sulfite (2 mL) was added and stirred vigorously for 30 min. Brine (2 mL) was added and the aqueous layer was extracted with ethyl acetate (3×10 mL). The organic layers were combined, dried and concentrated in vacuo to obtain 0.1 g of crude. The crude was purified by flash column chromatography [0, 5, 10, 50, 100% methanol in ethyl acetate] to furnish 0.08 g (62%) of the triol as a semisolid, MS (ES+) 405.2 [100%, (M+1)].

To a solution of above solid (0.08 g, 0.2 mmol) in tetrahydrofuran (2 mL) was added 1 N sodium hydroxide (1.2 mL, 1.2 mmol) and stirred at room temperature for 1.5 h. Ether (5 mL) and water (2 mL) were added, and the organic layers were separated. The aqueous layer was washed with ethyl acetate (2×5 mL). The aqueous layer was acidified to pH 5-4 using 1 N HCl saturated with sodium chloride, and extracted with ethyl acetate (3×5 mL). The organic layers were combined, dried and concentrated in vacuo to furnish 0.02 g (26%) of 3β-(tert-butoxycarbonylamino)-4α-[(1-methylcarbonylamino)(2,3,4-trihydroxy)butyl]cyclopentan-carboxylic acid (isomer B at C-6) as a white solid, MS (ES+) 391.4 [20%, (M+1)] and 373.6 [100%, (M+1)–$H_2O$].

To a solution of above acid (0.02 g, 0.05 mmol) in dichloromethane (1.0 mL) was added trifluoroacetic acid (0.08 mL, 1.1 mmol) and the reaction was stirred at room temperature overnight. Additional trifluoroacetic acid (0.08 mL, 1.1 mmol) was added and the reaction was stirred at room temperature for 1 h. The solvent was removed in vacuo and traces of trifluoroacetic acid were removed in vacuo by co-distilling the residue twice with dichloromethane (10 mL). The residue was dissolved in water (0.5 mL), concentrated in vacuo and dried at acetone reflux temperature in vacuo to obtain 0.2 g (77%) of the title compound as a tan solid, mp 58–62° C.

Analysis: Calculated for $C_{12}H_{22}N_2O_6 \cdot 2C_2HF_3O_2$: C, 37.08; H, 4.67; N, 5.40 Found: C, 37.50; H, 4.43; N, 5.28

Example 12

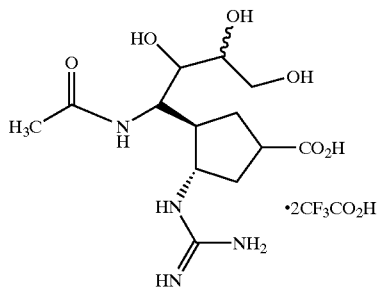

3β-{[(Amino)(imino)methyl]amino}-4α-[(1-methylcarbonylamino) (2,3,4-trihydroxy)butyl)butyl]-cyclonentancarboxylic acid trifluoroacetic acid (1:2) (isomer A at C-1, isomer A at C-6, isomer B at C-7)

To a solution of 2-{3β-(tert-butoxycarbonylamino)-4α-[(formyl)methylcarbonylamino)-methyl]cyclopentylidene}-1,3-dithane (isomer A at C-6), from Example 10 (1.75 g, 4.4 mmol), in tetrahydrofuran (100 mL) cooled to −78° C. was added dropwise vinylmagnesium bromide (Aldrich, 1.0 M solution on tetrahydrofuran, 44 mL, 44 mmol) and stirred at −78° C. for 2 h. The reaction was quenched carefully with saturate aqueous ammonium chloride (20 mL), ether (100 mL) and brine (20 mL) was added and the reaction mixture was allowed to warm to room temperature. The organic layers were separate and the aqueous layer was extracted with ether (3×50 mL) and dichloromethane (100 mL). The organic layers were combined, dried and concentrated in vacuo to furnish 2.0 g of a white solid.

To the above solid (2.0 g, 4.4 mmol) dissolved in dimethylformamide (20 mL) was added tert-butyldimethylsilyl chloride (0.86 g, 5.5 mmol), imidazole (0.6 g, 8.8 mmol) and 4-dimethylaminopyridine (0.14 g, 0.11 mmol). The reaction mixture was stirred at room temperature overnight. The reaction was quenched with water (20 mL), and extracted with ether (3×25 mL), dried and concentrated in vacuo to furnish 2.48 g of crude. Purification of the crude by flash column chromatography (150 g silica gel, 10–30% ethyl acetate in hexane) gave the following isomers of 2-{3β-(tert-butoxycarbonylamino)-4α-{2-{[(tert-butyl)(dimethyl)silyl]oxy}-3-butenyl}cyclopentylidene}-1,3-dithiane:

1. 0.22 g (9%) of isomer A at C-6, isomer A at C-7 as a white solid, mp 72–76° C. (dec).

Analysis: Calculated for $C_{26}H_{46}N_2O_4S_2Si \cdot 0.5H_2O$: C, 56.59; H, 8.59; N, 5.08 Found: C, 56.61; H, 8.43; N, 4.97

2. 0.86 g (36%) of isomer A at C-6, isomer B at C-7 as a white solid, mp 116–118° C.

Analysis Calculated for $C_{26}H_{46}N_2O_4S_2Si$: C, 57.53; H, 8.54; N, 5.16 Found: C, 57.84; H, 8.59; N, 5.23

To a solution of isomer A at C-6, isomer B at C-7 from above (0.58 g, 1.07 mmol) in methanol (16.6 mL) was added 6 N HCl (2.8 mL, 16.6 mmol) and the mixture was stirred at room temperature overnight. The reaction mixture was cooled to 0° C. and sodium hydroxide (0.86 g, 10.7 mmol) was added and the reaction was stirred at room temperature for 1 h. The reaction was quenched with glacial acetic acid (0.64 mL, 10.7 mmol) and concentrated in vacuo. To the residue obtained was added 1 N HCl (2.14 mL, 2.14 mmol), ethyl acetate (10 mL) and water (10 mL). The aqueous layer was separated, saturated with sodium chloride and extracted with ethyl acetate (2×10 mL). The organic layers were combined and concentrated in vacuo to furnish 0.33 g (85%) of crude.

The above crude was dissolved in anhydrous methanol (8 mL) and cooled to 0° C. A solution of dry HCl in ether (Aldrich, 1.0 M solution, 1.6 mL) was added and the reaction mixture was stirred overnight at room temperature. The reaction mixture was concentrated in vacuo (bath temperature 25° C.) to obtain a crude residue of methyl 3β-(tert-butoxycarbonylamino)-4α-[(2-hydroxy)(1-methylcarbonylamino)-3-butenyl]cyclopentancarboxylate as an oil, MS (ES+) 371.5 [100%, (M+1)].

To a solution of above compound in dichloromethane (8.0 mL) was added (1.26 mL, 16.4 mmol) trifluoroacetic acid, and the reaction was stirred at room temperature overnight. Additional trifluoroacetic acid (0.63 mL, 8,2 mmol) was added and the reaction was stirred at room temperature for 1 h. The solvent was removed in vacuo and traces of trifluoroacetic acid were removed in vacuo by co-distilling the residue twice with dichloromethane (5 mL). The residue was dissolved in dimethylformamide (5 mL), triethylamine (0.58 mL, 4.1 mmol), 1,3-bis(tert-butoxycarbonyl)-2-methyl-2-thiopseudourea (0.29 g, 0.98 mmol), and mercuric chloride (0.27 g, 0.98 mmol) were added, and the reaction was stirred overnight at room temperature. The reaction mixture was diluted with ethyl acetate (20 mL) and filtered to remove inorganic impurities. The filtrate was washed with water (2×10 mL) and brine (10 mL), dried and concentrated in vacuo to obtain 0.4 g of crude. The crude was purified by flash column chromatography [silica gel (20 g), 40–50% ethyl acetate in hexane] to furnish the two C-1 isomers of methyl 3β-{[(tert-butoxycarbonylamino)(tert-butoxycarbonylimino)methyl]amino}-4α-[(2-hydroxy)(1-methylcarbonylamino)-3-butenyl]cyclopentancarboxylate:

1. 0.15 g (27%) of isomer A at C-1, as a semisolid, MS (ES+) 495.5 [100%, (M+1)–H$_2$O] and 513.6 [10%, (M+1)].
2. 0.07 g (13%) of isomer B at C-1, as a semisolid, MS (ES+) 513.5 [100%, (M+1)].

The above isomer A (0.15 g, 0.29 mmol) was dissolved in tetrahydrofuran/tert-butanol (2 mL, 1:1) and N-methyl morpholine oxide (50 mg), osmium tetraoxide (few crystals) and water (1 mL) were added. The reaction mixture was stirred overnight at room temperature. A saturated, aqueous solution of sodium sulfite (2 mL) and sodium sulfite (1 g) was added and stirred vigorously for 30 min. Brine (2 mL) was added and the aqueous layer was saturated with sodium chloride and extracted with ethyl acetate (3×10 mL). The organic layers were combined, dried and concentrated in vacuo to obtain 0.15 g (94%) of pure methyl 3β-{[(tert-butoxycarbonylamino)(tert-butoxycarbonylimino)methyl]amino}-4α-[(1-methylcarbonylamino)-(2,3,4-trihydroxy)butyl]cyclopentancarboxylate (isomer A at C-1), MS (ES+) 529.4 [100%, (M+1)–H$_2$O] and 547.4 [50%, (M+1)].

To a solution of above solid (0.15 g, 0.27 mmol) in tetrahydrofuran (1.5 mL) was added 1 N sodium hydroxide (1.4 mL, 1.4 mmol), and stirred at room temperature for 2.0 h. Ether (2 mL) and water (2 mL) were added and organic layers were separated. The aqueous layer was washed with ether (2×5 mL). The aqueous layer was acidified to pH 4 using 1 N HCl saturated with sodium chloride and extracted with ethyl acetate (3×5 mL). The organic layers were combined, dried and concentrated in vacuo to furnish 0.13 g (84%) of acid as a white solid, MS (ES+) 515.4 [80%, (M+1)–H$_2$O] and 533.5 [30%, (M+1)]

To a solution of the above acid (0.13 g, 0.24 mmol) in dichloromethane (2.0 mL) was added trifluoroacetic acid (0.04 mL, 0.48 mmol) and the reaction was stirred at room temperature overnight. Additional trifluoroacetic acid (0.02 mL, 0.24 mmol) was added and the reaction was stirred at room temperature for 1 h. The solvent was removed in vacuo and traces of excess trifluoroacetic acid were removed in vacuo by co-distilling the residue twice with dichloromethane (10 mL). The residue was dissolved in water (1.0 mL), concentrated in vacuo and dried at acetone reflux temperature in vacuo to obtain 0.07 g (46%) of the title compound as a tan solid, mp 76–80° C.

Analysis: Calculated for C$_{13}$H$_{24}$N$_4$O$_6$·2C$_2$HF$_3$O$_2$: C, 36.44; H, 4.67; N, 9.99 Found: C, 36.81; H, 4.24; N, 9.55

Example 13

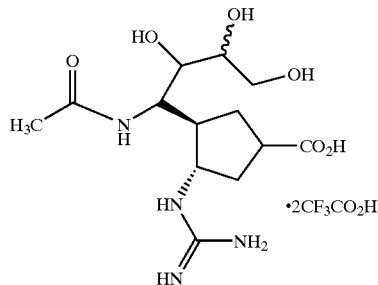

3β-{[(Amino)(imino)methyl]amino}-4α-[(1-methylcarbonylamino)(2,3,4-trihydroxy)butyl]-cyclopentancarboxylic acid trifluoroacetic acid (1:2) (isomer B at C-1, isomer A at C-6, isomer B at C-7)

Methyl 3β-{[(tert-butoxycarbonylamino)(tert-butoxycarbonylimino)methyl]amino}-4α-[(2-hydroxy)(1-methylcarbonylamino)-3-butenyl]cyclopentancarboxylate (isomer B at C-1, from Example 12) (70 mg, 0.14 mmol), was dissolved in tetrahydrofuran/tert-butanol (2 mL, 1:1) and N-methyl morpholine oxide (50 mg), osmium tetraoxide (few crystals) and water (1 mL) were added. The reaction mixture was stirred overnight at room temperature. A saturated aqueous solution of sodium sulfite (2 mL) and sodium sulfite (1 g) was added and stirred vigorously for 30 min. Brine (2 mL) was added and the aqueous layer was saturated with sodium chloride and extracted with ethyl acetate (3×10 mL). The organic layers were combined, dried and concentrated in vacuo to obtain 0.07 g (86%) of methyl 3β-{[(tert-butoxycarbonylamino)(tert-butoxycarbonylimino)methyl]amino}-4α-[(1-methylcarbonylamino)(2,3,4-trihydroxy)butyl]cyclo-pentancarboxylate (isomer B at C-1), MS (ES+) 547.4 [100%, (M+1)].

To a solution of above solid (0.07 g, 0.13 mmol) in tetrahydrofuran (1.5 mL) was added 1 N sodium hydroxide (0.64 mL, 0.64 mmol) and stirred at room temperature for 2 h. Ether (2 mL) and water (2 mL) were added and organic layers were separated. The aqueous layer was washed with ether (2×5 mL). The aqueous layer was acidified to pH 4 using 1 N HCl, saturated with sodium chloride, and extracted with ethyl acetate (3×5 mL). The organic layers were combined, dried and concentrated in vacuo to furnish 0.017 g (26%) of acid as a white solid, MS (ES+) 533.2 [60%, (M+1)].

To a solution of above acid (0.017 g, 0.03 mmol) in dichloromethane (2.0 mL) was added trifluoroacetic acid (0.06 mL, 0.6 mmol) and the reaction was stirred at room temperature overnight. Additional trifluoroacetic acid (0.03 mL, 0.3 mmol) was added and the reaction was stirred at room temperature for 1 h. The solvent was removed in vacuo and traces of excess trifluoroacetic acid were removed in vacuo by co-distilling the residue twice with dichloromethane (10 mL). The residue was dissolved in water (1.0 mL) concentrated in vacuo and dried at acetone reflux temperature in vacuo to obtain 0.01 g (60%) of the title compound as a tan solid, mp 124–128° C.

Analysis: Calculated for C$_{13}$H$_{24}$N$_4$O$_6$·2C$_2$HF$_3$O$_2$: C, 36.44; H, 4.67; N, 10.00 Found: C, 35.84; H, 4.24; N, 10.51

Example 14

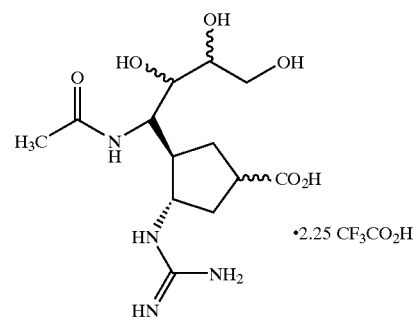

3β-{[(Amino)(imino)methyl]amino}-4α-[(1-methylcarbonylamino)(2,3,4-trihydroxy)butyl]cyclo-pentancarboxylic acid trifluoroacetic acid (4:9) (isomer B at C-6, isomer A at C-1, C-7 and/or C-8)

To a solution of 2-{3β-(tert-butoxycarbonylamino)-4α-[(formyl)(methylcarbonylamino)-methyl]cyclopentylidene}-1,3-dithiane (isomer B at C-6) (2.58 g, 6.45 mmol) from Example 10 in tetrahydrofuran (64 mL)

cooled to −78° C. was added dropwise vinylmagnesium bromide (Aldrich, 1.0 M solution in tetrahydrofuran, 64.5 mL, 64.5 mmol) and the mixture stirred at −78° C. for 1 h. The reaction was quenched carefully with saturated aqueous ammonium chloride (20 mL). Ether (100 mL) and brine (20 mL) were added and reaction mixture was allowed to warm to room temperature. The organic layers were separated and the aqueous layer was extracted with ether (3×50 mL). The organic layers were combined, dried and concentrated in vacuo to furnish 3.7 g of a white solid.

To the above solid (2.0 g, 4.4 mmol) dissolved in dimethylformamide (30 mL) was added tert-butyldimethylsilyl chloride (1.31 g, 8.44 mmol), imidazole (0.92 g, 13.5 mmol) and dimethylaminopyridine (0.21 g, 1.69 mmol). The reaction mixture was stirred at room temperature overnight. The reaction was quenched with water (30 mL) and extracted with ether (3×30 mL). The organic layers were combined and washed with water (30 mL) and brine (30 mL), dried and concentrated in vacuo to furnish 3.8 g of crude. Purification of the crude by flash column chromatography (210 g silica gel, 25% ethyl acetate in hexane) gave 1.44 g (41%) of 2-{3β-(tert-butoxycarbonylamino)-4α-[(1-methylcarbonylamino)(2-{[(tert-butyl)(dimethyl)silyl]oxy}-3-butenyl]cyclopentylidene}-1,3-dithiane (isomer B at C-6, 85:15 mixture of isomers at C-7) as a white solid, mp 76–84° C.

Analysis: Calculated for $C_{26}H_{46}N_2O_4S_2Si$: C, 57.53; H, 8.54; N, 5.16 Found: C, 57.29; H, 8.52; N, 5.09

To a solution of 2-{3β-(tert-butoxycarbonylamino)-4α-[(1-methylcarbonylamino)(2-{[(tert-butyl)(dimethyl)silyl]oxy}-3-butenyl]cyclopentylidene}-1,3-dithiane (1.4 g, 2.58 mmol) in methanol (39.0 mL) was added 6 N HCl (6.5 mL, 39.0 mmol) and the mixture was stirred at room temperature overnight. The reaction mixture was cooled to 0° C. and sodium hydroxide (2.07 g, 51.7 mmol) was added and the reaction was stirred at room temperature for 1 h. The reaction was quenched with glacial acetic acid (1.6 mL, 27 mmol) and concentrated in vacuo. To the residue obtained was added 1 N HCl (5.2 mL, 5.2 mmol), ethyl acetate (10 mL) and water (20 mL). The aqueous layer was separated, saturated with sodium chloride and extracted with ethyl acetate (2×10 mL). The organic layers were combined and concentrated in vacuo to furnish 0.68 g (74%) of crude.

The above crude was dissolved in anhydrous methanol (19 mL) and cooled to 0° C. A solution of dry HCl in ether (Aldrich, 1.0 M solution, 3.8 mL) was added and the reaction mixture was stirred overnight at room temperature. The reaction mixture was concentrated in vacuo (bath temperature 25° C.) to obtain methyl 3β-(tert-butoxycarbonylamino)-4α-[(2-hydroxy)(1-methylcarbonylamino)-3-butenyl]cyclopentancarboxylate as an oil, MS (ES+) 371.5 [100%, (M+1)].

To a solution of above ester in dichloromethane (19 mL) was added (2.94 mL, 38.0 mmol) of trifluoroacetic acid and the reaction was stirred at room temperature overnight. Additional trifluoroacetic acid (1.5 mL, 17 mmol) was added and the reaction was stirred at room temperature for 1 h. The solvent was removed in vacuo and traces of trifluoroacetic acid were removed in vacuo by co-distilling the residue twice with dichloromethane (5 mL). The residue was dissolved in dimethylformamide (10 mL) and triethylamine (1.4 mL, 10 mmol), 1,3-bis(tert-butoxycarbonyl)-2-methyl-2-thiopseudourea (0.66 g, 2.28 mmol), and mercuric chloride (0.62 g, 2.28 mmol) were added. The reaction was stirred overnight at room temperature, and the reaction mixture was diluted with ethyl acetate (30 mL) and filtered to remove inorganic impurities. The filtrate was washed with water (2×10 mL) and brine (10 mL), dried and concentrated in vacuo to obtain 0.78 g of crude. The crude was purified by flash column chromatography [silica gel (40 g), 40–50% ethyl acetate in hexane] to furnish two isomers of methyl 3β-{[(tert-butoxycarbonylamino)(tert-butoxycarbonylimino)methyl]amino}-4α-[(2-hydroxy)(1-methyl-carbonylamino)-3-butenyl]cyclopentancarboxylate:

1. 0.15 g (16%) of isomer A as a semisolid, MS (ES+) 495.5 [100% (M+1)−H$_2$O] and 513.6 [30%, (M+1)].
2. 0.12 g (13%) of isomer B as a semisolid, MS (ES+) 513.5 [100%, (M+1)].

The above isomer A (0.13 g, 0.25 mmol) was dissolved in tetrahydrofuran/tert-butanol (2 mL, 1:1) and N-methylmorpholine oxide (50 mg), osmium tetraoxide (few crystals) and water (1 mL) were added. The reaction mixture was stirred overnight at room temperature. A saturated aqueous solution of sodium sulfite (2 mL) and sodium sulfite (1 g) was added and stirred vigorously for 30 min. Brine (2 mL) was added and the aqueous layer was saturated with sodium chloride and extracted with ethyl acetate (3×10 mL). The organic layers were combined, dried and concentrated in vacuo to obtain 0.12 g (92%) of methyl 3β-{[(tert-butoxycarbonylamino)(tert-butoxycarbonylimino)methyl]amino}-4α-[(1-methylcarbonylamino)(2,3,4-trihydroxy)butyl]-cyclopentancarboxylate, MS (ES+) 547.4 [20%, M+1)] and 529.4 [100%, (M+1)−H$_2$O].

To a solution of above solid (0.12 g, 0.23 mmol) in tetrahydrofuran (1 mL) was added 1 N sodium hydroxide (1.1 mL, 1.1 mmol) and the mixture stirred at room temperature for 2.0 h. Ether (2 mL) and water (2 mL) were added, the layers were separated and the aqueous layer was saturated with sodium chloride and extracted with ethyl acetate (3×5 mL). The organic layers were combined, dried and concentrated in vacuo to furnish 0.033 g (25%) of acid as a white solid, MS (ES+) 515.4 [25%, (M+1)−H$_2$O] and 533.4 [5%, (M+1)].

To a solution of above acid (0.033 g, 0.06 mmol) in dichloromethane (2.0 mL) was added trifluoroacetic acid (0.1 mL, 1.2 mmol) and the reaction was stirred at room temperature overnight. Additional trifluoroacetic acid (0.05 mL, 0.6 mmol) was added and the reaction was stirred at room temperature for 1 h. The solvent was removed in vacuo and traces of excess trifluoroacetic acid were removed in vacuo by co-distilling the residue twice with dichloromethane (10 mL). The residue was dissolved in water (1.0 mL), concentrated in vacuo and dried at acetone reflux temperature in vacuo to obtain 0.018 g (49%) of the title compound as a tan solid, mp 125–135° C.

Analysis: Calculated for $C_{13}H_{24}N_4O_6 \cdot 2.25C_2HF_3O_2$: C, 35.69; H, 4.49; N, 9.51 Found: C, 36.02; H, 4.19; N, 9.58

Example 15

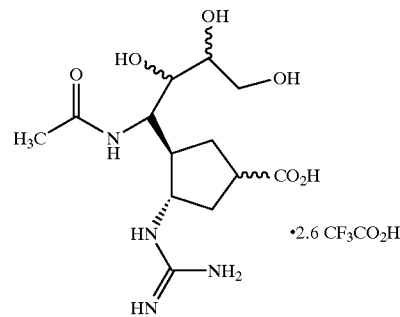

3β-{[(Amino)(imino)methyl]amino}-4α-[(1-methylcarbonylamino)(2,3,4-trihydroxy)butyl]cyclopentancarboxylic acid trifluoroacetic acid (5:13) (isomer B at C-6, isomer B at C-1, C-7 and/or C-8)

Methyl 3β-{[(tert-butoxycarbonylamino)(tert-butoxycarbonylimino)methyl]amino}-4α-[(2-hydroxy)(1-methylcarbonylamino)-3-butenyl]cyclopentancarboxylate (isomer B at C-6, isomer B at C-1 and C-7, from Example 14) (0.12 g, 0.24 mmol) was dissolved in tetrahydrofuran/tert-butanol (2 mL, 1:1) and N-methylmorpholine oxide (60 mg), osmium tetraoxide (few crystals) and water (1 mL) was added. The reaction mixture was stirred overnight at room temperature. A saturated aqueous solution of sodium sulfite (2 mL) and sodium sulfite (1 g) were added and the reaction stirred vigorously for 30 min. Brine (2 mL) was added, the aqueous layer was saturated with sodium chloride and extracted with ethyl acetate (3×10 mL). Organic layers were combined, dried and concentrated in vacuo to obtain 0.11 g (87%) of methyl 3β-{[(tert-butoxycarbonylamino)(tert-butoxycarbonylimino)methyl]amino}-4α-[(1-methylcarbonylamino)-(2,3,4-trihydroxy)butyl]cyclopentancarboxylate, MS (ES+) 547.5 [100%, (M+1)].

To a solution of the above solid (0.11 g, 0.2 mmol) in tetrahydrofuran (1 mL) was added 1 N sodium hydroxide (1.1 mL, 1.1 mmol) and the mixture stirred at room temperature for 2 h. Ether (2 mL) and water (2 mL) were added and organic layers were separated. The aqueous layer was washed with ether (2×5 mL). The aqueous layer was acidified to pH 4 using 1 N HCl, saturated with sodium chloride and extracted with ethyl acetate (3×5 mL). The organic layers were combined, dried and concentrated in vacuo to furnish 0.013 g (12%) of acid as a white solid, MS (ES+) 533.5 [100%, (M+1)].

To a solution of the above acid (0.013 g, 0.24 mmol) in dichloromethane (2.0 mL) was added trifluoroacetic acid (0.04 mL, 0.48 mmol) and the reaction was stirred at room temperature overnight. Additional trifluoroacetic acid (0.02 mL, 0.24 mmol) was added and the reaction was stirred at room temperature for 1 h. The solvent was removed in vacuo and traces of excess trifluoroacetic acid were removed in vacuo by co-distilling the residue twice with dichloromethane (10 mL). The residue was dissolved in water (1.0 mL), concentrated in vacuo and dried at acetone reflux temperature in vacuo to obtain 0.01 g of the title compound, mp 140–145° C.

Analysis: Calculated for $C_{13}H_{24}N_4O_6 \cdot 2.6C_2HF_3O_2$: C, 34.76; H, 4.26; N, 8.91 Found: C, 34.52; H, 4.20; N, 9.16

Example 16

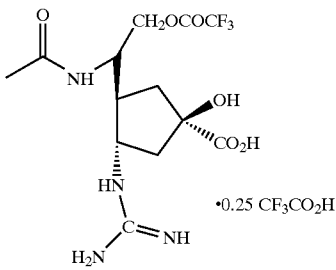

c-3-{[(Amino)(imino)methyl]amino}-t-1-hydroxy-t-4-[(1-methylcarbonylamino)(2-trifluoromethyl-carbonyloxy)ethyl]cyclopentan-r-carboxylic acid trifluoroacetic acid (4:1) (isomer A at C-6)

To a mixture of tris-(methylthio)methane (1.08 g, 7.0 mmol) in tetrahydrofuran (15 mL) at −78° C. was added n-butyllithium (1.6 M, 4.4 mL, 7.0 mmol) under nitrogen over a period of 2 min. The mixture was further stirred for 0.5 h at this temperature and to this was added a mixture of 3β-{[(tert-butoxycarbonylamino)(tert-butoxycarbonylimino)methyl]amino}-4α-[(ethoxycarbonyl)(methylcarbonylamino)methyl]cyclopentanone (Isomer A from Example 6, 0.49 g, 1.0 mmol) in tetrahydrofuran (5 mL). The reaction mixture was quenched with saturated ammonium chloride solution (5 mL) after stirring for 1 h at −78° C. The mixture was allowed to warm to room temperature and the organic layer was separated. The aqueous layer was further extracted with ether (10 mL). The combined organic layers were dried (MgSO₄), filtered and the filtrate concentrated to give a syrup, which was purified by passing through a column of silica gel (25 g) using ether/hexane (3:1) as an eluent to give 0.42 g (66%) of t-3-{[(tert-butoxycarbonylamino)(tert-butoxycarbonylimino)methyl]amino}-c-4-[(ethoxycarbonyl)(methyl-carbonylamino)methyl]-t-1-[tris(methylthio)methyl]cyclopentan-r-ol (isomer A at C-6) as a white solid. An analytical sample was prepared by recrystallization from ether/hexane, mp 155° C. (dec).

Analysis: Calculated for $C_{26}H_{46}N_4O_8S_3$: C, 48.88; H, 7.26; N, 8.77 Found: C, 49.00; H, 7.34; N, 8.64

To a solution of the above compound (1.5 g, 2.4 mmol) in tetrahydrofuran (25 mL) was added dropwise under nitrogen lithium borohydride (Aldrich, 0.22 g, 9.6 mmol) and lithium 9-borabicyclo[3.3.1]nonane hydride (Aldrich, 1 M solution in tetrahydrofuran, 0.24 mL, 0.24 mmol) and the reaction mixture was stirred at room temperature overnight. More lithium borohydride (0.16 g, 7.2 mmol) and lithium 9-borabicyclo[3.3.1]nonane hydride (Aldrich, 1 M solution in tetrahydrofuran, 0.24 mL, 0.24 mmol) was added and the reaction was stirred at room temperature for 4 h. The reaction was quenched with 1 N sodium hydroxide (3 mL), brine (3 mL) and stirred for 5 min. The reaction was acidified to pH 4 using glacial acetic acid. Ether (10 mL) was added and the aqueous layer was separated. The aqueous layer was neutralized with saturated aqueous sodium bicarbonate and extracted with ether (2×10 mL). The organic layers were combined, dried and concentrated in vacuo to obtain 1.55 g of a yellow oil. The oil was purified by flash column chromatography [20% chloroform:methanol:conc ammonium hydroxide (80:18:2) in dichloromethane]. The oil was crystallized from ether/hexane to furnish 0.6 g (42%) of t-3-{[(tert-butoxycarbonylamino)(tert-butoxycarbonylimino)methyl]amino}-c-4-[(2-hydroxy)(1-methyl-carbonylamino)ethyl]-t-1-[tris(methylthio)methyl]cyclopentan-r-ol (isomer A at C-6) as a white solid, mp 108–112° C.

Analysis: Calculated for $C_{24}H_{44}N_4O_7S_3$: C, 48.30; H, 7.43; N, 9.39 Found: C, 48.37; H, 7.49; N, 9.25

To a mixture of the above compound (1.0 g, 1.69 mmol), mercuric chloride (1.69 g, 6.23 mmol) and mercuric oxide (0.48 g, 2.53 mmol) was added methanol/water (40/3 mL) and the reaction mixture was stirred at room temperature for 30 min. The mixture was filtered through a pad of Celite and Florisil (17 g). The cake was washed with methanol (20 mL) and the filtrate concentrated in vacuo to furnish 1.8 g of a white semisolid. The crude was purified by flash column chromatography [silica gel (33 g); 75% ethyl acetate in hexane and 10% methanol in ethyl acetate] to furnish 0.57 g (68%) of methyl c-3-{[(tert-butoxycarbonylamino)(tert-butoxycarbonylimino)methyl]amino}-t-1-hydroxy-t-4-[(2-hydroxy)(1-methylcarbonylamino)ethyl]-cyclopentan-r-carboxylate (isomer A at C-6) as a white solid, mp 72–74° C. [$R_f$=0.47, 5% methanol in ethyl acetate].

Analysis: Calculated for $C_{22}H_{38}N_4O_9$: C, 52.58; H, 7.62; N, 11.15 Found: C, 52.85; H, 7.82; N, 10.93

To a solution of the above ester (0.5 g, 1.0 mmol) in tetrahydrofuran (10 mL) was added 1 N sodium hydroxide (2.0 mL, 2.0 mmol) and water (3 mL). The reaction mixture was stirred at room temperature for 1 h, tetrahydrofuran was removed in vacuo and the aqueous layer was made acidic with glacial acetic acid (pH=5). The aqueous layer was saturated with sodium chloride and extracted with ethyl acetate (5×10 mL). The organic layers were combined and concentrated in vacuo to furnish 0.43 g (88%) of c-3-{[(tert-butoxycarbonylamino)(tert-butoxycarbonylimino)methyl]amino}-t-1-hydroxy-t-4-[(2-hydroxy)(1-methylcarbonylamino)ethyl]-cyclopentan-r-carboxylic acid (isomer A at C-6, as a white solid, MS (ES+) 489.5 [50%, (M+1)].

The above acid (0.29 g, 0.6 mmol) was dissolved in dichloromethane (12 mL), trifluoroacetic acid (0.91 mL, 11.8 mmol) was added and the reaction was stirred at room temperature overnight. Additional trifluoroacetic acid (0.45 mL, 5.9 mmol) was added and the reaction was stirred at room temperature for 1 h. The solvent was removed in vacuo and traces of excess trifluoroacetic acid were removed in vacuo by co-distilling the residue twice with dichloromethane (10 mL). The residue was triturated with ether to obtain 0.14 g (560%) of the title compound as a white solid, mp 148–160° C.

Analysis: Calculated for $C_{13}H_{19}F_3N_4O_9 \cdot 0.25C_2HF_3O_2$: C, 39.28; H, 4.70; N, 13.57 Found: C, 39.34; H, 5.00; N, 13.26

Example 17

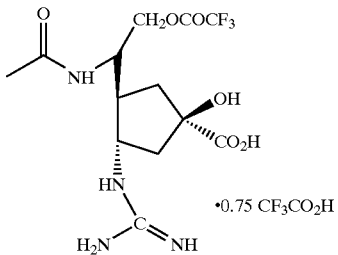

c-3-{[(Amino)(imino)methyl]amino}-t-1-hydroxy-t-4-[(1-methylcarbonylamino)(2-trifluoromethyl-carbonyloxy)ethyl]cyclopentan-r-carboxylic acid trifluoroacetic acid (4:3) (isomer B at C-6)

To tris(methylthio)methane (Aldrich, 18.9 mL, 142 mmol) in tetrahydrofuran (250 mL) at −78° C. was added dropwise over a period of 10 min under nitrogen n-butyl lithium (1.6M solution in hexane, 98 mL, 156 mmol) and stirred at −78° C. for 40 min. To the anion at −78° C. was added a solution of 3β-{[(tert-butoxycarbonylamino)(t-butoxycarbonylimino)methyl]amino}-4α-[(ethoxycarbonyl)(methylcarbonylamino)methyl]cyclopentanone, isomer B from Example 6 (8.58 g, 17.7 mmol), in tetrahydrofuran (85 mL) dropwise over a period of 10 min and the reaction mixture stirred at −78° C. for 1.5 h. The reaction was quenched with saturated ammonium chloride (50 mL) and warmed to room temperature. Ether (50 mL) was added and the organic layers were combined, dried over $MgSO_4$ and concentrated in vacuo to furnish crude. Purification of the crude by flash column chromatography (silica gel, 660 g, 30–50% ethyl acetate in hexane) gave 3.8 g (34%) of t-3-{[(tert-butoxycarbonylamino)(tert-butoxycarbonylimino)methyl]amino}-c-4-[(ethoxycarbonyl)(methylcarbonylamino)methyl]-t-1-[tris(methylthio)methyl]cyclopentan-r-ol (isomer B at C-6) as a white solid, mp 94–96° C.

Analysis: Calculated for $C_{26}H_{48}N_4O_8S_3$: C, 48.88; H, 7.26; N, 8.77 Found: C, 49.08; H, 7.05; N, 8.75

To a solution of the above compound (1.4 g, 2.2 mmol) in tetrahydrofuran (22 mL) was added dropwise under nitrogen lithium borohydride (Aldrich, 0.38 g, 16.43 mmol) and lithium 9-borabicyclo[3.3.1]nonane hydride (Aldrich, 1 M solution in tetrahydrofuran, 0.44 mL, 0.44 mmol), and the reaction mixture was stirred at room temperature overnight. The reaction was quenched with 1 N sodium hydroxide (3 mL), brine (3 mL) and stirred for 5 min. The reaction was acidified to pH 4 using glacial acetic acid, ether (10 mL) was added and the aqueous layer was separated. The aqueous layer was neutralized with saturated aqueous sodium bicarbonate and extracted with ether (2×10 mL). The organic layers were combined, dried and concentrated in vacuo to obtain 1.44 g of a yellow oil. The oil was purified by flash column chromatography [20% chloroform:methanol:conc ammonium hydroxide (80:18:2) in dichloromethane]. The oil was crystallized from ether/hexane to furnish 0.47 g (36%) of t-3-{[(tert-butoxycarbonylamino)(tert-butoxycarbonylimino)methyl]amino}-c-4-[(2-hydroxy)(1-methylcarbonylamino)ethyl]-t-1-[tris(methylthio)methyl] cyclopentan-r-ol (isomer B at C-6) as a white solid, mp 108–110° C.

Analysis: Calculated for $C_{24}H_{44}N_4O_7S_3$: C, 48.30; H, 7.43; N, 9.39 Found: C, 48.58; H, 7.51; N, 9.20

To a mixture of the above compound (0.78 g, 1.32 mmol), mercuric chloride (1.34 g, 4.9 mmol) and mercuric oxide (0.43 g, 1.97 mmol) was added methanol/water (29.5/2.5 mL) and the reaction mixture was stirred at room temperature for 30 min. The mixture was filtered through a pad of Celite and Florisil (13 g). The cake was washed with methanol (20 mL) and the filtrate concentrated in vacuo to furnish 1.1 g of a white semisolid. The crude was purified by flash column chromatography [silica gel (30 g); 75% ethyl acetate in hexane and 10% methanol in ethyl acetate] to furnish 0.42 g (630%) of methyl c-3-{[(tert-butoxycarbonylamino)(tert-butoxycarbonylimino)methyl]amino}-t-1-hydroxy-t-4-[(2-hydroxy)(1-methylcarbonylamino)ethyl]-cyclopentan-r-carboxylate (isomer B at C-6) as a white solid, mp 194–198° C.

Analysis: Calculated for $C_{22}H_{38}N_4O_9 \cdot 0.5H_2O$: C, 51.65; H, 7.68; N, 10.95 Found: C, 51.37; H, 7.50; N, 10.93

To a solution of the above ester (0.38 g, 0.76 mmol) in tetrahydrofuran (7.5 mL) was added 1 N sodium hydroxide (1.5 mL, 1.5 mmol) and water (2.25 mL). The reaction mixture was stirred at room temperature for 1 h. Tetrahydrofuran was removed in vacuo and the aqueous layer was made acidic with glacial acetic acid (pH=5). The aqueous layer was saturated with sodium chloride and extracted with ethyl acetate (5×10 mL). The organic layers were combined and concentrated in vacuo to furnish 0.325 g (87%) of acid. This was triturated with ethyl acetate in hexane to furnish 0.18 g of c-3-{[(tert-butoxycarbonylamino)(tert-butoxycarbonyl-imino)methyl]amino}-t-1-hydroxy-t-4-[(2-hydroxy)(1-methylcarbonylamino)ethyl]-cyclopentan-r-carboxylic acid (isomer B at C-6) as a white solid, MS (ES+) 489.4 [100%, (M+1)].

The above acid (0.15 g, 0.31 mmol) was dissolved in dichloromethane (6 mL), trifluoroacetic acid (0.48 mL, 6.3 mmol) was added and the reaction was stirred at room temperature overnight. Additional trifluoroacetic acid (0.24 mL, 3.2 mmol) was added and the reaction was stirred at room temperature for 1 h. The solvent was removed in vacuo and traces of excess trifluoroacetic acid were removed in vacuo by co-distilling the residue twice with dichloromethane (10 mL). The residue was triturated with ethanol/ ether to obtain 0.125 g (86%) of the title compound as a white solid, mp 210–220° C.

Analysis: Calculated for $C_{13}H_{19}F_3N_4O_9 \cdot 0.75 C_2HF_3O_2$: C, 37.07; H, 4.24; N, 11.93 Found: C, 37.33; H, 4.45; N, 12.22

Example 18

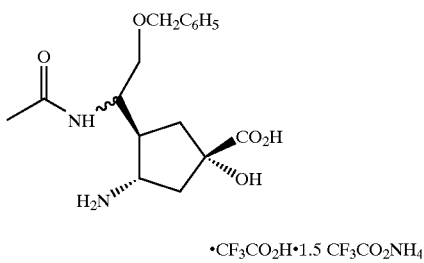

•$CF_3CO_2H$•1.5 $CF_3CO_2NH_4$ t-3-Amino-c-4-[(1-methylcarbonylamino)(2-phenylmethoxy)ethyl]-t-1-hydroxycyclopentan-r-carboxylic acid trifluoroacetic acid ammonium trifluoroacetate (2:2:3)

A mixture of c-3-(tert-butoxycarbonylamino)-t-4-[(1-methylcarbonylamino)(2-phenylmethoxy)ethyl]-t-1-[bis(phenylthio)methyl]cyclopentan-r-1-ol from Example 8 (2.53 g, 4.1 mmol), mercuric oxide (1.90 g, 8.8 mmol), and boron trifluoride etherate (1.1 mL, 8.9 mmol) in a 15% aqueous solution of tetrahydrofuran (70 mL) was stirred at room temperature for 2 h. The reaction mixture was filtered through a pad of Celite and Florisil. The filtrate was concentrated in vacuo to give 2.74 g of the crude. To the above crude in methanol (50 mL) was added iodine (1.9 g, 7.5 mmol) and the reaction mixture was heated to 50° C. To this mixture was added dropwise a solution of potassium hydroxide (0.71 M/methanol, 50 mL, 35.7 mmol). After 2 h stirring at 50° C., the reaction mixture was filtered through Celite. The filtrate was concentrated in vacuo and the resulting residue was dissolved in ethyl acetate (30 mL) and water (20 mL). The layers were separated and the aqueous layer was extracted with ethyl acetate (4×10 mL). The combined organic extracts were washed with brine, dried ($MgSO_4$), filtered through Celite, and concentrated in vacuo to provide 3.6 g of crude. Purification by flash column chromatography (silica gel, 200 g, 50–100% ethyl acetate/hexanes) gave 0.224 g (14%) of the desired hydroxyacid as a white solid. To a solution of hydroxyacid (0.244 g, 0.56 mmol) in dichloromethane (15 mL) was added trifluoroacetic acid (0.86 mL, 11.2 mmol) and the reaction mixture was stirred at room temperature for 12 h. The reaction mixture was concentrated in vacuo to give crude. Purification by flash column chromatography (silica gel, 60 g, chloroform/methanol/ammonium hydroxide: 80/18/2) gave 0.241 g of a thick, yellow oil. Trituration of the yellow oil with ether provided 0.185 g (51%) of the title compound as a tan solid, mp 37–39° C.

Analysis Calculated for $C_{17}H_{24}N_2O_5 \cdot C_2HF_3O \cdot 1.5 C_2H_4F_3NO_2$: C, 40.84; H, 4.83; N, 7.58 Found: C, 40.86; H, 5.08; N, 7.90

Example 19

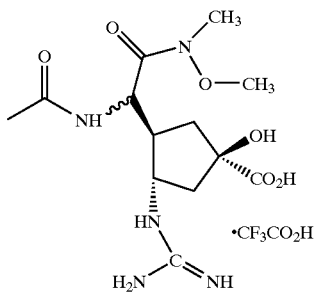

c-3-{[(Amino)(imino)methyl]amino}-t-1-hydroxy-t-4{(methylcarbonylamino){[(methyl)-(methoxy)amino]carbonyl}methyl}cyclopentan-r-carboxylic acid trifluoroacetic acid (1:1)

To a solution of t-3-{[(tert-butoxycarbonylamino)(tert-butoxycarbonylimino)methyl]-amino}-c-4-[(ethoxycarbonyl)(methylcarbonylamino)methyl]-t-1-[tris(methylthio)methyl]cyclo-pentan-r-ol (isomer B at C-6) (from Example 17, 2.1 g, 3.3 mmol) in ethanol (4 mL) and tetrahydrofuran (16.5 mL) was added 1 N sodium hydroxide (6.6 mL, 6.6 mmol) and water (4 mL) and the reaction mixture stirred at room temperature for 2 h. Tetrahydrofuran was removed in vacuo and the aqueous layer was acidified to pH 5-4 using glacial acetic acid. The solid obtained was collected by filtration and dried in vacuo at toluene reflux temperature to furnish 1.78 g (87%) of t-3-{[(tert-butoxycarbonylamino)(tert-butoxycarbonylimino)methyl]amino-c-4-[(carboxy)-(methylcarbonylamino)methyl]-t-1-[tris(methylthio)methyl]cyclopentan-r-ol as a white solid, MS (ES+) 611.5.

To a solution of the above acid (0.92 g, 1.5 mmol) in dichloromethane/tetrahydrofuran (12/3 mL) cooled to 0° C. was added methyl chloroformate (0.13 mL, 1.58 mmol) and triethylamine (0.25 mL, 1.8 mmol). The reaction mixture was stirred at 0° C. for 30 min and a cold prepared solution of N,O-dimethylhydroxylamine hydrochloride (0.22 g, 2.25 mmol) and triethylamine (0.42 mL, 3.0 mmol) in dichloromethane (5 mL) that had been stirred at 0° C. for 30 min was added. The reaction mixture was allowed to warm to room temperature and stirred overnight. Ether (20 mL), tetrahydrofuran (5 mL) and 0.5 N sodium hydroxide (20 mL) were added and the organic layer was separated. The organic layer was washed with brine (20 mL), dried and concentrated in vacuo to furnish crude amide as an oil. Purification of the crude by flash column chromatography (60 g silica gel, 50–100% ethyl acetate in hexane) gave 0.63 g (64%) of t-3-{[(tert-butoxycarbonylamino)(tert-butoxycarbonylimino)methyl]amino}-c-4-{(methylcarbonylamino){[(methoxy)(methyl)amino]carbonyl}methyl}-t-1-[tris(methylthio)methyl]-cyclopentan-r-ol as a white solid. An analytical sample, mp 200° C., was prepared by crystallization from ether.

Analysis: Calculated for $C_{26}H_{47}N_5O_8S_3$: C, 47.76; H, 7.25; N, 10.71 Found: C, 47.96; H, 7.28; N, 10.63

To a mixture of the above compound (0.5 g, 0.77 mmol), mercuric chloride (0.78 g, 2.8 mmol) and mercuric oxide (0.25 g, 1.15 mmol) was added methanol/water (16.3/1.4 mL), and the reaction mixture stirred at room temperature for 30 min. The mixture was filtered through a pad of Celite and Florisil (7 g). The cake was washed with methanol (20 mL) and the filtrate concentrated in vacuo to furnish 1.8 g of a white semisolid. The crude was purified by flash column chromatography [silica gel (20 g); 75% ethyl acetate in hexane and 10% methanol in ethyl acetate to furnish 0.35 g (82%) of methyl c-3-{[(tert-butoxycarbonylamino)(tert-butoxycarbonylimino)methyl]amino}-t-1-hydroxy-t-4-{(methylcarbonylamino)-{[(methoxy)(methyl)amino]carbonyl}methyl}cyclopentan-r-carboxylate as a white solid, mp 72–74° C. [$R_f$=0.29 and 0.15, ethyl acetate]; MS (ES+) 560.6.

To a solution of above solid (0.352 g, 0.63 mmol) in tetrahydrofuran (6.3 mL) was added 1 N sodium hydroxide (1.3 mL, 1.3 mmol) and water (5 mL) and the reaction mixture was stirred at room temperature for 1 h. Tetrahydrofuran was removed in vacuo and the aqueous layer was washed with ether (2×10 mL). The aqueous layer was acidified to pH 5-4 using glacial acetic acid, and saturated with sodium chloride and extracted with ethyl acetate (3×10 mL). The combined organic layer was dried and concentrated in vacuo to furnish 0.23 g (67%) of c-4-{[(tert-butoxycarbonylamino)(tert-butoxycarbonylimino)methyl]amino}-t-1-hydroxy-t-4-{(methyl-carbonylamino){[(methoxy)(methyl)amino]carbonyl}methyl}cyclpentan-r-carboxylic acid as a white solid, MS (ES+) 546.6.

To a solution of above acid (0.18 g, 0.33 mmol) in dichloromethane (6.6 mL) was added trifluoroacetic acid (0.51 mL, 6.6 mmol) and the reaction was stirred at room temperature overnight. Additional trifluoroacetic acid (0.25 mL, 3.3 mmol) was added and the reaction was stirred at room temperature for 1 h. The solvent was removed in vacuo and traces of excess trifluoroacetic acid were removed in vacuo by co-distilling the residue twice with dichloromethane (10 mL). The residue was dissolved in water (5 mL) and concentrated in vacuo to obtain a white solid which was triturated with ether to obtain 0.14 g (92%) of the title compound as a white solid, mp 160–16° C.

Analysis: Calculated for $C_{13}H_{23}N_5O_6C_2HF_2O_2$: C, 39.22; H, 5.26; N, 15.25 Found: C, 39.09; H, 5.29; N, 14.95

Example 20

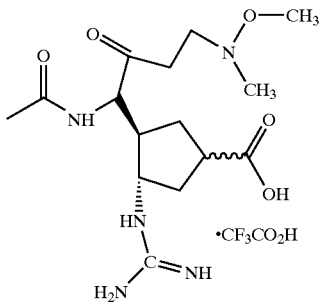

3β-{[(Amino)(imino)methyl]amino}-4α-{{4-(methoxy)(methyl)amino]-1-(methylcarbonylamino)-2-oxo}butyl}cyclopentancarboxylic Acid Trifluoroacetic Acid (1:1)

To a solution of 2-{3β-{[(tert-butoxycarbonylamino)(tert-butoxycarbonylimino)methyl]amino}-4α-[(ethoxycarbonyl)(methylcarbonylamino)methyl]-1-cyclopentylidene}-1,3-dithiane from Example 6 (6.74 g, 11.5 mmol) in ethanol (57.5 mL) and tetrahydrofuran (115 mL) was added 1 N sodium hydroxide (23 mL, 23 mmol) and water (35 mL) and the reaction mixture was stirred at room temperature for 5 h. Tetrahydrofuran was removed in vacuo and the aqueous layer was extracted with ethyl acetate (2×10 mL). The aqueous layer was acidified to pH 5-4 using glacial acetic acid. The solid obtained was collected by filtration and dried in vacuo at acetone reflux temperature to furnish 5.95 g (93%) of 2-{3β-{[(tert-butoxycarbonylamino)(tert-butoxycarbonylimino)methyl]amino}-4α-[(carboxy)(methyl-carbonylamino)methyl]-1-cyclopentylidene}-1,3-dithiane as a white solid. An analytical sample, mp 158° C., was prepared by crystallization from ethanol.

Analysis: Calculated for $C_{24}H_{38}N_4O_7S_2 \cdot 0.75C_2H_6O$: C, 51.63; H, 7.22; N, 9.44 Found: C, 51.70; H, 7.26; N, 9.18

To a solution of the above acid (0.63 g, 1.13 mmol) in dichloromethane/tetrahydrofuran (8/2 mL) cooled to 0° C. was added methyl chloroformate (0.1 mL, 1.24 mmol) and triethylamine (0.19 mL, 1.36 mmol). The reaction mixture was stirred at 0° C. for 30 min and a cold solution of N,O-dimethylhydroxylamine hydrochloride (0.17 g, 1.7 mmol) and triethylamine (0.32 mL, 2.26 mmol) in dichloromethane (5 mL) that had been stirred at 0° C. for 30 min was added. The reaction mixture was allowed to warm to room temperature and stirred overnight. Brine (5 mL), water (5 mL) and saturated sodium carbonate (5 mL) were added and the organic layer was separated. The organic layer was dried and concentrated in vacuo to furnish an oil. Purification of the crude by flash column chromatography (34 g silica gel, 50–75% ethyl acetate in hexane) gave 0.48 g (63%) of 2-{3β-{[(tert-butoxycarbonylamino)(tert-butoxycarbonylimino)methyl]amino}-4α-{{[(methoxy)(methyl)amino]carbonyl}methyl}cyclopentylidene}-1,3-dithiane. An analytical sample, mp 190–192° C., was prepared by crystallization from ether/hexane.

Analysis: Calculated for $C_{26}H_{43}N_5O_7S_2$: C, 51.89; H, 7.20; N, 11.64 Found: C, 52.32; H, 7.24; N, 11.33

To a solution of the above compound (3.4 g, 5.7 mmol) in tetrahydrofuran (50 mL) was added dropwise vinylmagnesium bromide (Aldrich, 1 M solution in tetrahydrofuran, 33.94 mL, 33.94 mmol) over a period of 10 min. The reaction mixture was stirred at room temperature for 10 min and quenched with saturated ammonium chloride solution and brine (1:1, 30 mL). Ether (25 mL) was added and the organic layer was separated. The aqueous layer was washed with ether (25 mL). The organic layers were combined, dried and concentrated in vacuo to furnish an oil. Purification of the crude by flash column chromatography (180 g silica gel, 20–70% ethyl acetate in hexane) gave 2.0 g (56%) of 2-{3β-{[(tert-butoxycarbonylamino)(tert-butoxycarbonylimino)methyl]amino}-4α-{{4-[(methoxy)(methyl)amino]-1-(methylcarbonyl-amino)-2-oxo}butyl}cyclopentylidene}-1,3-dithiane as a white solid, mp 99–101° C.

Analysis: Calculated for $C_{28}H_{47}N_5O_7S_3$: C, 53.40; H, 7.52; N, 11.12; S, 10.18 Found: C, 53.81; H, 7.48; N, 10.96; S, 10.25

To a solution of the above compound (0.55 g, 0.9 mmol) in methanol (26.4 mL) was added 6 N HCl (2.2 mL, 13.0 mmol) and the mixture was stirred at room temperature until all starting material had disappeared (TLC analysis, ethyl acetate, ~30 h). The reaction mixture was cooled to 0° C. and sodium hydroxide (0.72 g, 18 mmol) was added and the reaction was stirred at room temperature for 1 h. The reaction was quenched with glacial acetic acid (0.5 mL) and concentrated in vacuo to furnish a residue. To the residue was added ethyl acetate (10 mL) and water (10 mL). The aqueous layer was separated and extracted with ethyl acetate (10 mL). The organic layers were combined and concentrated in vacuo to furnish crude. The above crude was purified by flash column chromatography (50–80% ethyl acetate in hexane) to furnish 0.29 g (56%) of methyl 3β-{[(tert-butoxycarbonylamino)(tert-butoxycarbonylimino)methyl]amino}-4α-{{4-[(methoxy)-(methyl)amino]-1-(methylcarbonylamino)-2- oxo}butyl}cyclopentancarboxylate as an oil. The oil was crystallized from ether as a white solid.

Analysis: Calculated for $C_{26}H_{45}N_5O_9$: C, 54.63; H, 7.93; N, 12.25 Found: C, 54.66; H, 7.87; N, 11.94

To a solution of the above ester (0.2 g, 0.35 mmol) in tetrahydrofuran (3.5 mL) was added 1 N sodium hydroxide (0.88 mL, 0.88 mmol) and water (2 mL) and the reaction mixture was stirred at room temperature for 2 h. Tetrahydrofuran was removed in vacuo and water (5 mL) was added. The aqueous layer was washed with ether (2×5 mL) and acidified to pH 5–4 using glacial acetic acid. The aqueous layer was saturated with sodium chloride and extracted with ethyl acetate (3×10 mL). The combined organic layers were dried and concentrated in vacuo to furnish 0.18 g of the corresponding cyclopentancarboxylic acid as a white solid, MS (ES+) 558.3 [100%, (M+1)].

To a solution of the above acid (0.18 g, 0.33 mmol) in dichloromethane (6.6 mL) was added trifluoroacetic acid (0.51 mL, 6.6 mmol) and the reaction was stirred at room temperature overnight. Additional trifluoroacetic acid (0.25 mL, 3.3 mmol) was added and the reaction was stirred at room temperature for 1 h. The solvent was removed in vacuo and traces of excess trifluoroacetic acid were removed in vacuo by co-distilling the residue twice with dichloromethane (10 mL). The residue was washed with ether (2×10 mL), precipitated with methanol/ether and dried at toluene reflux temperature in vacuo to obtain the title compound as a tan solid, mp 189–192° C.

Analysis: Calculated for $C_{15}H_{27}N_5O_5 \cdot C_2HF_3O_2$: C, 43.31; H, 5.99; N, 14.85 Found: C, 43.38; H, 5.74; N, 14.42

Example 21

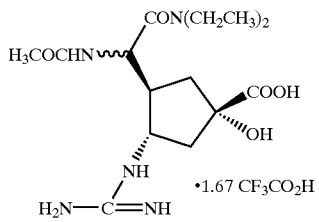

t-3-{[(Amino)(imino)methyl]amino}-c-4-[(diethylaminocarbonyl)(methylcarbonylamino)methyl]-t-1-hydroxycyclopentan-r-carboxylic acid trifluoroacetic acid (3:5)

To a stirred solution of tris(methylthio)methane (1.6 mL, 12 mmol) in tetrahydrofuran (20 mL) at −78° C. was added dropwise n-butyl lithium (2.5M, 5.3 mL, 13.3 mmol). After 30 min of stirring, 3β-tert-butoxycarbonylamino-4α-[bis(ethoxycarbonyl)(methylcarbonylamino)methyl]-cyclopentanone from Example 8 (1.0 g, 2.4 mmol) in tetrahydrofuran (15 mL) was added dropwise. The reaction mixture was stirred at −78° C. for 3 h then quenched with a saturated aqueous solution of ammonium chloride (15 mL). The separated aqueous layer was extracted with ether (4×10 mL). The combined organic extracts were washed with brine, dried ($MgSO_4$), filtered through Celite, and concentrated in vacuo to provide crude. Purification by radial PLC (silica gel, 25–35% ethyl acetate/hexane) gave 0.48 g (35%) of c-3-(tert-butoxycarbonylamino)-t-4-[bis-(ethoxycarbonyl)(methylcarbonylamino)methyl]-t-1-[tris(methylthio)methyl]cyclopentan-r-ol as a white solid, mp 98–100° C.

Analysis: Calculated for $C_{23}H_{40}N_2O_8S_3$: C, 48.57; H, 7.09; N, 4.93 Found: C, 48.74; H, 7.00; N, 4.91

To a mixture of the above compound (1.71 g, 3.0 mmol) in ethanol (15 mL) was added 1 N sodium hydroxide (15 mL) and heated at reflux for 2 h. The mixture was acidified with acetic acid and heated at reflux again for 1 h and concentrated. To the residue was added water (50 mL) and the mixture extracted with dichloromethane (3×50 mL). The combined organic extracts were dried ($MgSO_4$), filtered and concentrated to give c-3-(tert-butoxycarbonylamino)-t-4-[(carboxy)(methylcarbonylamino)methyl]-t-1-[tris(methylethio)methyl]cyclopentan-r-ol (1.2 g, 85%).

To a mixture of the above acid (1.2 g, 2.56 mmol) in tetrahydrofuran (15 mL) at −5° C. was added triethylamine (0.29 g 2.8 mmol) and ethyl chloroformate (0.31 g, 2.8 mmol) and stirred for 0.5 h. To this mixture was then added diethylamine (0.38 g, 5.2 mmol) and stirred at 0° C. for 1 h and at room temperature for 3 h. The mixture was diluted with ethyl acetate (100 mL) and water (75 mL). The organic layer was separated, washed with water (100 mL) and brine (100 mL), and dried ($MgSO_4$). After filtration, the filtrate was concentrated to give 1.1 g (82%) of crude c-3-(tert-butoxycarbonylamino)-t-4-[(diethylaminocarbonyl)(methylcarbonylamino)methyl]-t-1-[tris(methylthio)methyl]cyclopentan-r-ol.

To a mixture of the above crude amide (1.10 g, 2.10 mmol) in a methanol (12):water (1) mixture (51.0 mL) was added mercury (II) chloride (2.10 g, 7.75 mmol) and mercury (II) oxide (0.69 g, 3.18 mmol) and stirred for 2 h. The solids were removed by filtration through Celite and washed with dichloromethane (100 mL). To the filtrate was added water (100 mL) and the organic layer separated. The aqueous layer was further extracted with dichloromethane (2×80 mL). The combined organic layers were dried ($MgSO_4$), filtered and the filtrate concentrated to give 0.9 g (100%) of a syrup of crude methyl t-3-(tert-butoxycarbonylamino)-c-4-[(diethylaminocarbonyl)(methylcarbonylamino)methyl]-t-1-hydroxycyclopentan-r-carboxylate.

A mixture of the above crude ester (0.9 g) in dichloromethane (50 mL) was stirred with trifluoroacetic acid (5.0 mL) for 16 h. The reaction mixture was concentrated and dried in vacuo to give 0.93 g (100%) of the corresponding crude methyl t-3-amino-c-4-[(diethylaminocarbonyl)(methylcarbonylamino)methyl]-t-1-hydroxycyclopentan-r-carboxylate. It was used as such for the next step.

To a mixture of above amine (0.93 g, 2.1 mmol) in dimethylformamide (20 mL) were added triethylamine (1.06 g, 10.5 mmol), N,N'-bis-tert-butoxycarbonyl-S-methylisothiourea (0.61 g, 2.1 mmol), and mercury (II) chloride (0.57 g, 2.1 mmol) and the mixture stirred at room temperature for 2 h. The mixture was diluted with ethyl acetate (100 mL) and filtered through Celite. The filtrate was washed with water (2×100 mL), and brine (1×100 mL). The organic layer was dried ($MgSO_4$), filtered and concentrated to give a syrup, which was purified by passing through a column of silica gel (50 g) using 5% methanol in ethyl acetate to give 0.65 g (54%) of methyl t-3-{[(tert-butoxycarbonylamino)(tert-butoxycarbonylimino)methyl]amino}-c-4-[(diethylaminocarbonyl)(methylcarbonylamino)methyl]-t-1-hydroxycyclopentan-r-carboxylate as a white powder, mp >120° C. (dec).

Analysis: Calculated for $C_{26}H_{45}N_5O_9$: C, 54.63; H, 7.93; N, 12.25 Found: C, 54.56; H, 7.97; N, 12.04

A mixture of the above ester (0.88 g, 0.66 mmol) in 0.1 N sodium hydroxide (13.0 mL, water-1, tetrahydrofuran-1, ethanol-1 mixture) was stirred at room temperature for 2 h. It was neutralized with acetic acid after filtration through a cotton plug and stirred at room temperature for 16 h. The precipitate obtained was collected by filtration, washed with water and dried in vacuo to give 0.33 g (90%) of t-3-{[(tert-butoxycarbonylamino)(tert-butoxycarbonylimino)methyl]

amino}-c-4-[(diethylaminocarbonyl)(methylcarbonylamino)methyl]-t-1-hydroxycyclopentan-r-carboxylic acid as a white solid, mp >235° C. (dec).

Analysis: Calculated for $C_{25}H_{43}N_5O_9$: C, 53.85; H, 7.77; N, 12.56 Found: C, 53.74; H, 7.83; N, 12.56

A mixture of t-3-{[(tert-butoxycarbonylamino)(tert-butoxycarbonylimino)methyl]amino}-c-4-[(diethylaminocarbonyl)(methylcarbonylamino)methyl]-t-1-hydroxycyclopentan-r-carboxylic acid (0.9 g, 0.16 mmol) in dichloromethane (5.0 mL) was stirred with trifluoroacetic acid (0.5 mL) for 48 h. It was then concentrated and dried in vacuo to give 0.8 g (90%) the title compound as a brown powder, mp 99–103° C. (dec).

Analysis: Calculated for $C_{15}H_{27}N_5O_5 \cdot 1.67 C_2HF_3O_2$: C, 40.23; H, 5.27; N, 12.79 Found: C, 40.38; H, 5.28; N, 12.38

Example 22

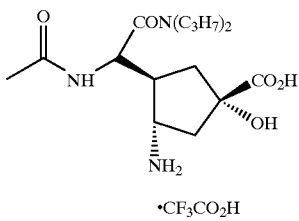

·CF$_3$CO$_2$H t-3-Amino-c-4-[(di-n-propylaminocarbonyl)(methylcarbonylamino)methyl]-t-1-hydroxy-cyclopentan-r-carboxylic acid trifluoroacetic acid (1:1) (isomer A at C-6)

To a mixture of c-3-(tert-butoxycarbonylamino)-t-4-[bis(ethoxycarbonyl)-(methylcarbonylamino)methyl]-t-1-[tris(methylthio)methyl]cyclopentan-r-ol from Example 21 (1.46 g, 2.6 mmol) in ethanol (20 mL) and water (10 mL) was added 1 N sodium hydroxide (10 mL, 10 mmol) and heated at reflux for 2 h. The mixture was concentrated in vacuo and acidified with glacial acetic acid (1.0 mL, 17.5 mmol). To the concentrate was added ethyl acetate (20 mL) and heated at reflux for 1 h. The layers were separated and the aqueous layer was extracted with ether (4×10 mL). The combined organic extracts were washed with brine, dried (MgSO$_4$), filtered through Celite, and concentrated in vacuo to provide c-3-(tert-butoxycarbonylamino)-t-4-[(carboxy)(methylcarbonylamino)methyl]-t-1-[tris(methyl-thio)methyl]cyclopentan-r-ol (0.98 g, 76%).

To a stirred mixture of the above acid (0.97 g, 2.0 mmol) in tetrahydrofuran (25 mL) at 0° C. was added ethyl chloroformate (2.1 mL, 2.2 mmol) and triethylamine (0.35 mL, 2.5 mmol). After stirring for 20 min, the reaction mixture was allowed to warm to room temperature, stirred for an additional 30 min, and filtered through Celite. The filtrate was concentrated in vacuo to give 0.85 g (100%) of crude mixed anhydride.

To a mixture of the above mixed anhydride (0.84 g, 1.56 mmol) in tetrahydrofuran (20 mL) at 0° C. was added di-n-propylamine (0.6 mL, 4.4 mmol). The reaction mixture was stirred at 0° C. for 30 min and at room temperature for 3 h. The mixture was diluted with water (10 mL) and layers were separated. The aqueous layer was extracted with ethyl acetate (4×10 mL). The combined organic extracts were washed with brine, dried (MgSO$_4$), filtered through Celite, and concentrated in vacuo to afford 1.0 g of the crude. Purification by radial PLC (silica gel, 35–50% ethyl acetate/hexane) gave 0.23 g (27%) of c-3-(tert-butoxycarbonylamino)-t-4-[(di-n-propylaminocarbonyl)(methylcarbonylamino)methyl]-t-1-[tris(methylthio)methyl]cyclopentan-r-ol (isomer A at C-6) as a single isomer.

To a mixture of the above amide (0.17 g, 0.31 mmol) in methanol (16.5 mL) and water (1.5 mL) at room temperature was added mercuric oxide (0.10 g, 0.47 mmol) and mercuric chloride (0.31 g, 1.2 mmol). After stirring for 2 h, the reaction mixture was filtered through a pad of Florisil and Celite. The filtrate was concentrated in vacuo to give 0.26 g of crude. Purification by radial PLC (silica gel, 50–75% ethyl acetate/hexane) furnished 0.14 g (96%) of methyl t-3-(tert-butoxycarbonylamino)-c-4-[(di-n-propylaminocarbonyl)(methylcarbonylamino)-methyl]-t-1-hydroxycyclopentan-r-carboxylate.

To a mixture of the above ester (0.13 g, 0.29 mmol) in tetrahydrofuran (3.5 mL) and water (2.5 mL) at room temperature was added 1 N sodium hydroxide (0.6 mL, 0.6 mmol). The reaction mixture was stirred for 1 h and concentrated in vacuo. The concentrate was acidified to pH 5–4 with glacial acetic acid and extracted with ethyl acetate (5×10 mL). The combined organic extracts were washed with brine, dried (MgSO$_4$), filtered through Celite, and concentrated in vacuo to afford 0.13 g (100%) of crude t-3-(tert-butoxycarbonylamino)-c-3-[(di-n-propylaminocarbonyl)(methylcarbonylamino)methyl]-t-1-hydroxycyclopentan-r-carboxylic acid.

A mixture of the above crude acid (0.13 g, 0.29 mmol) in dichloromethane (10 mL) with trifluoroacetic acid (0.45 mL, 5.8 mmol) was stirred at room temperature overnight. The reaction mixture was concentrated in vacuo to give 0.16 g of a thick oil which was triturated with ether to provide 0.083 g (63%) of the title compound as a tan solid, mp 168–170° C.

Analysis: Calculated for $C_{16}H_{29}N_3O_5 \cdot C_2HF_3O_2$: C, 47.26; H, 6.61; N, 9.19 Found: C, 47.47; H, 6.83; N, 9.33

Example 23

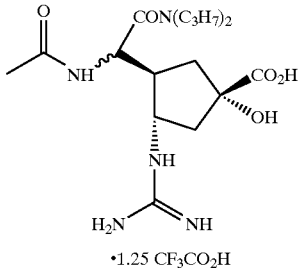

·1.25 CF$_3$CO$_2$H t-3-{[(Amino)(imino)methyl]amino}-c-4-[(di-n-propylamino carbonyl)(methylcarbonylamino)-methyl]-t-hydroxycyclpentan-r-carboxylic acid trifluoroacetic acid (4:5)

To a mixture of c-3-(tert-butoxycarbonylamino)-t-4-[bis(ethoxycarbonyl)(methyl-carbonylamino)methyl]-t-1-[tris(methylthio)methyl]cyclopentan-r-ol from Example 21 (1.46 g, 2.6 mmol) in ethanol (20 mL) and water (10 mL) was added 1 N sodium hydroxide (10 mL, 10 mmol) and heated at reflux for 2 h. The mixture was concentrated in vacuo and acidified with glacial acetic acid (1.0 mL, 17.5 mmol). To the concentrate was added ethyl acetate (20 mL) and heated at reflux for 1 h. The layers were separated and the aqueous layer was extracted with ether (4×10 mL). The combined organic extracts were washed with brine, dried (MgSO$_4$), filtered through Celite, and concentrated in vacuo to provide c-3-(tert-butoxycarbonylamino)-t-4-[(carboxy)(methylcarbonylamino)methyl]-t-1-[tris(methylthio)methyl]cyclopentan-r-ol (0.98 g, 76%).

To a stirred mixture of above solid (0.97 g, 2.0 mmol) in tetrahydrofuran (25 mL) at 0° C. was added ethyl chloroformate (0.21 mL, 2.2 mmol) and triethylamine (0.35 mL, 2.5 mmol). After stirring for 20 min, the reaction mixture was allowed to warm to room temperature, stirred for an additional 30 min, and filtered through Celite. The filtrate was concentrated in vacuo to give 0.85 g (100%) of the crude mixed anhydride.

To a mixture of above mixed anhydride (0.84 g, 1.56 mmol) in tetrahydrofuran (20 mL) at 0° C. was added di-n-propylamine (0.6 mL, 4.4 mmol). The reaction mixture was stirred at 0° C. for 30 min and at room temperature for 3 h. The mixture was diluted with water (10 mL) and the layers were separated. The aqueous layer was extracted with ethyl acetate (4×10 mL) The combined organic extracts were washed with brine, dried (MgSO$_4$), filtered through Celite, and concentrated in vacuo to afford 1.0 g of crude. Purification by radial PLC (silica gel, 35–50% ethyl acetate/hexane) gave 0.58 g (68%) of c-3-(tert-butoxycarbonylamino)-t-3-[(di-n-propylaminocarbonyl)(methylcarbonylamino)-t-1-[tris(methylthio)methyl]cyclopentan-r-ol.

To a mixture of the above amide (0.34 g, 0.63 mmol) in methanol (16.5 mL) and water (1.5 mL) at room temperature was added mercuric oxide (0.210 g, 0.97 mmol) and mercuric chloride (0.64 g, 2.4 mmol). After stirring for 2 h, the reaction mixture was filtered through a pad of Florisil and Celite. The filtrate was concentrated in vacuo to give 0.44 g of crude. Purification by radial PLC (silica gel, 50% ethyl acetate/hexane) furnished 0.27 g (94%) of methyl t-3-(tert-butoxycarbonylamino)-c-4-[(di-n-propylaminocarbonyl)(methylcarbonylamino)methyl]-t-1-hydroxycyclopentan-r-carboxylate.

A mixture of the above ester (0.15 g, 0.32 mmol) in dichloromethane (10 mL) with trifluoroacetic acid (0.5 mL, 6.6 mmol) was stirred at room temperature overnight. The reaction mixture was concentrated in vacuo to give 0.16 g of methyl t-3-amino-c-4-[(di-n-propylaminocarbonyl)(methylcarbonylamino)methyl]-t-1-hydroxycyclopentan-r-carboxylate as a thick oil.

To a mixture of above amine (0.16 g, 0.33 mmol) in dimethylformamide (3 mL) was added N,N'-bis-tert-butoxycarbonyl-S-methyl isothiourea (0.11 g, 0.37 mmol), triethylamine (0.3 mL, 2.2 mmol), and mercuric chloride (0.10 g, 0.37 mmol). The reaction mixture was stirred at room temperature for 3 h. To this mixture was added water (5 mL) and the layers were separated. The organic layer was washed with brine, dried (MgSO$_4$), filtered through Celite, and concentrated in vacuo to afford 0.22 g of a yellow solid. Purification by radial PLC (silica gel, 50–75% ethyl acetate/hexane) gave 0.13 g (67%) of methyl t-3{[(tert-butoxycarbonylamino)(tert-butoyxcarbonylimino)methyl]amino}-c-4-[(di-n-propylaminocarbonyl)(methylcarbonylamino)-methyl]-t-1-hydroxycyclopentan-r-carboxylate.

To a mixture of the above compound (0.13 g, 0.22 mmol) in tetrahydrofuran (4 mL) and water (2 mL) at room temperature was added 1 N sodium hydroxide (0.5 mL, 0.5 mmol). The reaction mixture was stirred for 2 h and concentrated in vacuo. The concentrate was acidified to pH 5–4 with glacial acetic acid and extracted with ethyl acetate (5×10 mL). The combined organic extracts were washed with brine, dried (MgSO$_4$), filtered through Celite, and concentrated in vacuo to afford 0.13 g (100%) of crude t-3-{[(tert-butoxycarbonylamino)(tert-butoxycarbonylimino)methyl]amino}-c-4-[(di-n-propylaminocarbonyl)(methylcarbonylamino)-methyl]-t-1-hydroxycyclopentan-r-carboxylic acid.

A mixture of the above acid (0.13 g, 0.22 mmol) and trifluoroacetic acid (0.5 mL, 6.6 mmol) in dichloromethane (10 mL) was stirred at room temperature overnight. The reaction mixture was concentrated in vacuo to give 0.2 g of the crude. Trituration with ether afforded 0.08 g (74%) of the title compound as a tan solid, mp 153–155° C.

Analysis: Calculated for C$_{17}$H$_{31}$N$_5$O$_5$·1.25C$_2$HF$_3$O$_2$: C, 44.36; H, 6.16; N, 13.26 Found: C, 44.34; H, 6.17; N, 13.19

Example 24

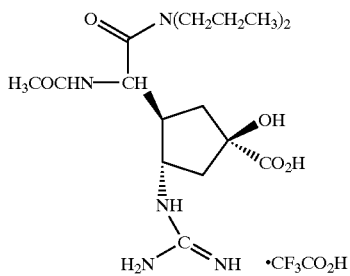

c-3-{[(Amino)(imino)methyl]amino}-t-4-[(di-n-propylaminocarbonyl)(methylcarbonylamino)-methyl]-t-1-hydroxycyclopentan-r-carboxylic acid trifluoroacetic acid (1:1) (isomer A at C-6)

To a mixture of t-3-{[(tert-butoxycarbonylamino)(tert-butoxycarbonylimino)methyl]-amino}-c-4-[(ethoxycarbonyl)(methlycarbonylamino)methyl]-t-1-[tris(methylthio)methyl]cyclo-pentan-r-ol (isomer A at C-6) from Example 16 (2.55 g, 4.0 mmol) in tetrahydrofuran (20 mL) and ethanol (10 mL) was added 1 N aqueous sodium hydroxide (7.0 mL, 7.0 mmol) and stirred at room temperature for 4 h. After neutralization with acetic acid, the mixture was concentrated. To the residue was added water (50 mL) and stirred for 4 h. The white precipitate obtained was collected by filtration, washed with water and dried in vacuo at 60° C. for 24 h to give 2.1 g (86%) of t-3-{[(tert-butoxycarbonylamino)(tert-butoxycarbonylimino)methyl]amino}-c-4-[(carboxy)(methyl-carbonylamino)methyl]-t-1-[tris(methylthio)methyl]cyclopentan-r-ol (mixture of isomers) as a white solid, mp 228–230° C. (dec).

Analysis: Calculated for C$_{24}$H$_{42}$N$_4$O$_8$S$_3$·H$_2$O: C, 45.84; H, 7.05; N, 8.91 Found: C, 45.31; H, 6.64; N, 9.05

To a mixture of the above acid (0.61 g, 1 mmol) in tetrahydrofuran (5 mL) at –5° C. was added triethylamine (0.1 g, 1 mmol) and ethyl chloroformate (0.11 g, 1 mmol) and stirred for 0.5 h. To this mixture was then added di-n-propylamine (0.1 g, 1 mmol), the mixture was stirred at 0° C. for 1 h and at room temperature for 1 h. The mixture was diluted with ethyl acetate (40 mL) and water (40 mL). The organic layer was separated, washed with water (50 mL) and brine (50 mL), and dried (MgSO$_4$). After filtration the filtrate was concentrated and the residue passed through a column of silica gel (25 g) using ethyl acetate/hexane (1:1) as an eluent to give 0.37 g (53%) of t-3-{[(tert-butoxycarbonylamino)(tert-butoxycarbonylimino)methyl]amino}-c-4-[(di-n-propylamino-carbonyl)(methylcarbonylamino)methyl]-t-1-[tris(methylthio)methyl]cyclopentan-r-ol (isomer A at C-6) as a white solid, mp 88–90° C.

Analysis: Calculated for C$_{30}$H$_{55}$N$_5$O$_7$S$_3$: C, 51.92; H, 7.99; N, 10.09 Found: C, 52.15; H, 8.04; N, 9.95

To a mixture of the above amide (0.6 g, 0.9 mmol) in methanol (12):water (1) mixture (22.0 mL) was added mercury (II) chloride (0.91 g, 3.35 mmol) and mercury (II) oxide (0.3 g, 1.40 mmol) and stirred for 0.5 h. The solids were removed by filtration through Celite and washed with dichloromethane (50 mL). To the filtrate was added water (50 mL) and an organic layer separated. The aqueous layer was further extracted with dichloromethane (2×40 mL). The combined organic layers were dried (MgSO$_4$), filtered and the filtrate concentrated to give a syrup, which was purified by passing through a column of silica gel (50 g) using ethyl acetate as an eluent to give 0.07 g (13%) of methyl c-3-{[(tert-butoxycarbonylamino)(tert-butoxycarbonylamino)-methyl]amino}-t-4-[(di-n-propylaminocarbonyl) (methylcarbonylamino)methyl]-t-1-hydroxycyclopentan-r-carboxylate (isomer A at C-6) as a white solid, mp 128–130° C. (dec).

Analysis: Calculated for C$_{28}$H$_{49}$N$_5$O$_9$: C, 56.08; H, 8.23; N, 11.68 Found: C, 56.20; H, 8.10; N, 11.84

A mixture of the above ester (0.13 g, 0.22 mmol) in tetrahydrofuran (2.0 mL) and ethanol (1.0 mL) was stirred with 1 N sodium hydroxide (0.5 mL, 0.5 mmol) for 1 h. It was neutralized with acetic acid and the precipitate obtained was collected by filtration, washed with water and dried in vacuo to give 0.08 g (67%) of c-3-{[(tert-butoxycarbonylamino)(tert-butoxycarbonylimino)methyl] amino}-t-4-[(di-n-propylaminocarbonyl) (methylcarbonylamino)-methyl]-t-1-hydroxycyclopentan-r-carboxylic acid (isomer A at C-6) as an off-white solid, mp 225–230° C. (dec).

Analysis: Calculated for C$_{27}$H$_{47}$N$_5$O$_9$.0.5H$_2$O: C, 54.53; H, 8.13; N, 11.78 Found: C, 54.25; H, 7.90; N, 11.48

A mixture of the above acid (0.66 g, 0.10 mmol) in dichloromethane (4.0 mL) was stirred with trifluoroacetic acid (1.0 mL) for 16 h. It was then concentrated and dried in vacuo to give 0.04 g (800) of the title compound as a white solid, mp 128–130° C. (dec).

Analysis: Calculated for C$_{17}$H$_{31}$N$_5$O$_5$.C$_2$HF$_3$O$_2$: C, 45.69; H, 6.46; N, 14.02 Found: C, 46.37; H, 6.69; N, 14.13

Example 25

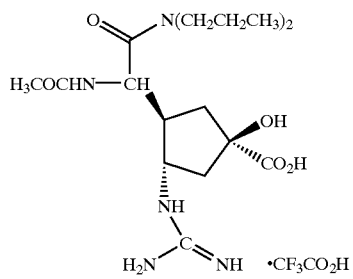

c-3-{[(Amino)(imino)methyl]amino}-t-4-[(di-n-propylaminocarbonyl)(methylcarbonylamino)-methyl]-t-1-hydroxycyclopentan-r-carboxylic acid trifluoroacetic acid (1:1) (isomer B at C-6)

To a mixture of t-3-{[(tert-butoxycarbonylamino)(tert-butoxycarbonylimino)methyl]-amino}-c-4-[(di-n-propylaminocarbonyl)(methylcarbonylamino)-methyl]-t-1-[tris(methylthio)-methyl]cyclopentan-r-ol (isomer B at C-6) which was isolated as a by-product from the preparation of isomer A in Example 24 (0.51 g, 0.73 mmol) in methanol (12):water (1) mixture (18.0 mL) was added mercury (II) chloride (0.75 g, 2.75 mmol) and mercury (II) oxide (0.24 g, 1.12 mmol) and stirred for 2 h. The solids were removed by filtration through Celite and washed with dichloromethane (50 mL). To the filtrate was added water (50 mL) and an organic layer separated. The aqueous layer was further extracted with dichloromethane (2×40 mL). The combined organic layers were dried (MgSO$_4$), filtered and the filtrate concentrated to give a white solid, which was recrystallized from ether/hexane to give 0.35 g (80%) of methyl c-3-{[(tert-butoxycarbonylamino)(tert-butoxycarbonylimino) methyl]amino}-t-4-[(di-n-propylaminocarbonyl)-(methylcarbonylamino)methyl]-t-1-hydroxycyclopentan-r-carboxylate (isomer B at C-6) as a white solid, mp 170–172° C. (dec).

Analysis: Calculated for C$_{28}$H$_{49}$N$_5$O$_9$: C, 56.08; H, 8.23; N, 11.68 Found: C, 55.96; H, 8.29; N, 11.70

To mixture of the above ester (0.25 g, 0.42 mmol) in tetrahydrofuran (3.0 mL) and ethanol (1.3 mL) was stirred with 1 N sodium hydroxide (1.0 mL, 1.0 mmol) for 2 h. The solvent was evaporated and the residue was dissolved in water (1 mL) and neutralized with acetic acid. The precipitate obtained was collected by filtration, washed with water and dried in vacuo to give 0.20 g (79%) of the corresponding acid.

A mixture of above acid (0.15 g, 0.26 mmol) in dichloromethane (10 mL) was stirred with trifluoroacetic acid (1.2 mL) for 16 h. It was then concentrated and dried in vacuo to give 0.11 g (85%) of the title compound as a white solid, mp 202–205° C. (dec).

Analysis: Calculated for C$_{17}$H$_{31}$N$_5$O$_5$.C$_2$HF$_3$O$_2$: C, 45.69; H, 6.46; N, 14.02 Found: C, 45.84; H, 6.51; N, 13.82

Example 26

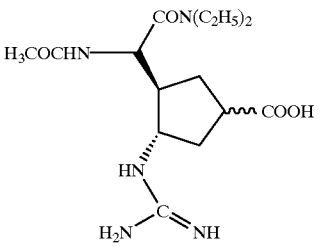

3β-{[(Amino)(imino)methyl]amino}-4α-[(diethylaminocarbonyl)(methylcarbonylamino)methyl]-cyclopentancarboxylic acid (isomer A at C-6)

To a mixture of 2-{3β-{[(tert-butoxycarbonylamino)(tert-butoxycarbonylimino)methyl]-amino}-4α-[(carboxy) (methylcarbonylamino)-1-cyclopentylidene}-1,3-dithiane from Example 20 (0.56 g, 1 mmol) in tetrahydrofuran (8 mL) at 0° C. was added triethylamine (0.11 g, 1.1 mmol) and methyl chloroformate (0.1 g, 1.1 mmol) and stirred for 0.5 h. To this mixture was then added diethylamine (0.11 g, 1.5 mmol) and stirred at 0° C. for 1 h and at room temperature for 1 h. The mixture was diluted with ethyl acetate (40 mL) and water (40 mL). The organic layer was separated, washed with water (50 mL) and brine (50 mL), and dried (MgSO$_4$). After filtration, the filtrate was concentrated and the residue passed through a column of silica gel (50 g) using ethyl acetate/hexane (1:1) as an eluent to give 0.21 g (34%) of the desired 2-{3β-{[(tert-butoxycarbonylamino)(tert-butoxycarbonylimino)methyl] amino}-4α-[(diethylaminocarbonyl)-(methylcarbonylamino)methyl]-1-cyclopentylidene}-1,3-dithiane as a white solid.

A mixture of the above amide (0.1 g, 0.016 mmol) in 0.5 N HCl in methanol (5.0 mL, 2.5 mmol) was stirred for 24 h at room temperature and 2 h at 45° C. To the mixture was added 6.0 N HCl (0.2 mL, 1.2 mmol) and heated at 45° C. for another 2 h. The reaction mixture was then concentrated and the residue stirred with 0.1 N sodium hydroxide (5.0 mL, 0.5 mmol) for 1 h, concentrated, and again stirred with 1 N sodium hydroxide (1.0 mL, 1.0 mmol) for 0.5 h. It was then filtered through a cotton plug and neutralized with dilute hydrochloric acid to give the title compound mixed with sodium chloride, MS (ES+) 342.3 (M+1, 100%).

Example 27

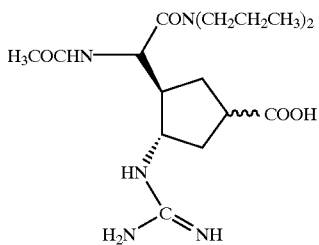

3β-{[(Amino)(imino)methyl]amino}-4α-[(di-n-propylaminocarbonyl)(methylcarbonylamino)-methyl]-cyclopentancarboxylic acid (isomer A at C-6)

To a mixture of 2-{3β-{[(tert-butoxycarbonylamino)(tert-butoxycarbonylimino)methyl]-amino}-4α-[(carboxy)(methylcarbonylamino)methyl]-1-cyclopentylidene}-1,3-dithiane (isomer A) from Example 20 (0.56 g, 1 mmol) in tetrahydrofuran (8 mL) at 0° C. was added triethylamine (0.11 g, 1.1 mmol) and methyl chloroformate (0.1 g, 1.1 mmol) and stirred for 0.5 h. To this mixture was then added di-n-propylamine (0.15 g, 1.5 mmol) and stirred at 0° C. for 1 h and at room temperature for 1 h. The mixture was diluted with ethyl acetate (40 mL) and water (40 mL). The organic layer was separated, washed with water (50 mL) and brine (50 mL), and dried (MgSO$_4$). After filtration, the filtrate was concentrated and the residue passed through a column of silica gel (50 g) using ethyl acetate/hexane (1:1) as an eluent to give 0.22 g (34%) of 2-{3β-{[(tert-butoxycarbonylamino)(tert-butoxycarbonylimino)methyl]amino}-4α-[(di-n-propylaminocarbonyl)-(methylcarbonylamino)methyl]-1-cyclopentylidene}-1,3-dithiane (isomer A) as a white solid, mp 125–126° C.

Analysis: Calculated for $C_{30}H_{51}N_5O_6S_2$: C, 56.14; H, 8.01; N, 10.91 Found: C, 56.72; H, 8.05; N, 10.76

A mixture of the above compound (0.11 g, 0.016 mmol) in 0.5 N HCl in methanol (5.0 mL, 2.5 mmol) was stirred for 24 h at room temperature and 2 h at 45° C. To the mixture was further added 6.0 N hydrochloric acid (0.2 mL, 1.2 mmol) and heated at 45° C. for another 2 h. The reaction mixture was then concentrated and the residue stirred with 0.1 N sodium hydroxide (5.0 mL, 0.5 mmol) for 1 h, concentrated, and again stirred with 1 N sodium hydroxide (1.0 mL, 1.0 mmol) for 0.5 h. It was then filtered through a cotton plug, neutralized with dilute hydrochloric acid and concentrated to give the title compound mixed with sodium chloride, MS (ES+) 370.4 (M+1, 100%).

Example 28

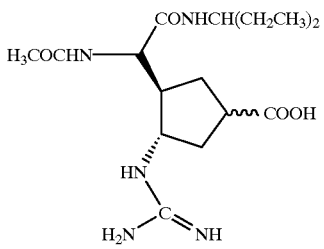

3β-{[(Amino)(imino)methyl]amino}-4α-[(methylcarbonylamino)(3-pentylaminocarbonyl)methyl]-cyclopentancarboxylic acid (isomer A at C-6)

To a mixture of 2-{3β-{[(tert-butoxycarbonylamino)(tert-butoxycarbonylimino)methyl]amino}-4α-[(carboxy)(methylcarbonylamino)methyl]-1-cyclopentyl-idene}-1,3-dithiane (isomer A) from Example 20 (0.56 g, 1 mmol) in tetrahydrofuran (8 mL) at 0° C. was added triethylamine (0.11 g, 1.1 mmol) and methyl chloroformate (0.1 g, 1.1 mmol) and stirred for 0.5 h. To this mixture was then added 3-pentylamine (0.2 g, 2.3 mmol) and stirred at 0° C. for 1 h and at room temperature for 1 h. The mixture was diluted with ethyl acetate (40 mL) and water (40 mL). The organic layer was separated, washed with water (50 mL) and brine (50 mL), and dried (MgSO$_4$). After filtration, the filtrate was concentrated and the residue passed through a column of silica gel (50 g) using ethyl acetate/hexane (1:1) as an eluent to give 0.28 g (45%) of 2-{3β-{[(tert-butoxycarbonylamino)(tert-butoxycarbonylimino)methyl]amino}-4α-[(methylcarbonylamino)(3-pentylaminocarbonyl)methyl]-1-cyclopentylidene}-1,3-dithiane (isomer A at C-6) as a white solid, mp >230° C. (dec).

Analysis: Calculated for $C_{29}H_{49}N_5O_6S_2$: C, 55.48; H, 7.86; N, 11.15 Found: C, 55.96; H, 7.92; N, 10.99

A mixture of the above compound (0,1 g, 0.016 mmol) in 0.5 N HCl in methanol (5.0 mL, 2.5 mmol) was stirred for 24 h at room temperature and 2 h at 45° C. To the mixture was further added 6.0 N hydrochloric acid (0.2 mL, 1.2 mmol) and heated at 45° C. for another 2 h. The reaction mixture was then concentrated and the residue stirred with 0.1 N sodium hydroxide (5.0 mL, 0.5 mmol) for 1 h, concentrated, and again stirred with 1 N sodium hydroxide (1.0 mL, 1.0 mmol) for 0.5 h. It was then filtered through a cotton plug, neutralized with dilute hydrochloric acid and concentrated to give the title compound mixed with sodium chloride, MS (ES+) 356.5 (M+1, 100%).

Example 29

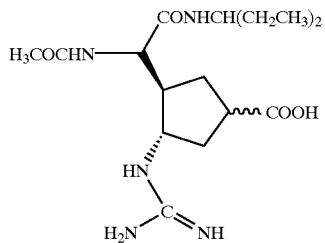

3β-{[(Amino)(imino)methyl]amino}-4α-[(methylcarbonylamino)(3-pentylaminocarbonyl)-methyl]cyclopentancarboxylic acid (isomer B at C-6)

To a mixture of 2-{3β-{[(tert-butoxycarbonylamino)(tert-butoxycarbonylimino)methyl]-amino}-4α-[(carboxy)(methylcarbonylamino) methyl]-1-cyclopentylidene}-1,3-dithiane (isomer A) from Example 20 (0.56 g, 1 mmol) in tetrahydrofuran (8 mL) at 0° C. was added triethylamine (0.11 g, 1.1 mmol) and methyl chloroformate (0.1 g, 1.1 mmol) and stirred for 0.5 h. To this mixture was then added 3-pentylamine (0.2 g, 2.3 mmol) and stirred at 0° C. for 1 h and at room temperature for 1 h. The mixture was diluted with ethyl acetate (40 mL) and water (40 mL). The organic layer was separated, washed with water (50 mL) and brine (50 mL), and dried (MgSO$_4$). After filtration, the filtrate was concentrated and the residue passed through a column of silica gel (50 g) using ethyl acetate/hexane (1:1) as an eluent to give 0.06 g (10%) of 2-{3β-{[(tert-butoxycarbonylamino)(tert-butoxycarbonylimino)methyl]amino}-4α-[(methylcarbonylamino)(3-pentylaminocarbonyl)methyl]-1-cyclopentylidene}-1,3-dithiane (isomer B at C-6) as a white solid, mp >200° C. (dec).

Analysis: Calculated for $C_{29}H_{49}N_5O_6S_2$: C, 55.48; H, 7.86; N, 11.15 Found: C, 55.21; H, 7.72; N, 11.06

To a mixture of the above compound (isomer B, 0.035 g, 0.005 mmol) in 0.5 N HCl in methanol (3.0 mL, 1.5 mmol) was stirred for 24 h at room temperature and 2 h at 45° C. To the mixture was further added 6.0 N hydrochloric acid (0.2 mL, 1.2 mmol) and heated at 45° C. for another 2 h. The reaction mixture was then concentrated and stirred with 1 N sodium hydroxide (0.4 mL, 0.4 mmol) for 4 h. It was then filtered through a cotton plug, neutralized with dilute hydrochloric acid and concentrated to give the title compound mixed with sodium chloride, MS (ES+) 356.4 (M+1, 100%).

Example 30

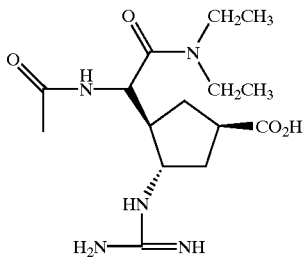

3β-{[(Amino)(imino)methyl]amino}-4α-[(diethylaminocarbonyl)(methylcarbonylamino)-methyl]cyclopentancarboxylic acid (isomer A at C-6, isomer A at C-1)

To a mixture of 2-{3β-(tert-butoxycarbonylamino)-4α-[(carboxy)(methyl-carbonylamino)methyl]cyclopentylidene}-1,3-dithiane (from Example 10) (10 g, 24.0 mmol) in tetrahydrofuran (150 mL) was added triethylamine (3.03 g, 30.0 mmol), and methyl chloroformate (2.84 g, 30.0 mmol) and stirred at room temperature for 1 h. To this mixture was added diethylamine (4.4 g, 60.0 mmol) and the mixture stirred for 16 h. The reaction mixture was diluted with ethyl acetate (200 mL) and washed with water (200 mL). The organic layer was separated, dried (MgSO₄), filtered and concentrated to give 9.1 g (81%) of a mixture of isomers at C-6 as residue. This residue was recrystallized from ethyl acetate to give 1.9 g of 2-{3β-(tert-butoxycarbonylamino)-4α-[(diethylaminocarbonyl)(methylcarbonylamino)methyl]cyclopentylidene-1,3-dithiane (isomer B at C-6).

To the above solid (1.88 g, 4.0 mmol) was added methanolic hydrochloric acid (100 mL, 0.5 N) and stirred for 16 h at 50° C. The mixture was then neutralized with methanolic sodium hydroxide and stirred for 0.5 h at room temperature. The mixture was concentrated and the residue passed through a column of silica gel (100 g) using chloroform (90): methanol (9): ammonium hydroxide (1) mixture as an eluent to give 0.6 g (50%) of methyl 3β-amino-4α-[(diethylaminocarbonyl)(methylcarbonylamino)-methyl]cyclopentancarboxylate (isomer B at C-6) as an off-white solid, mp 95° C.

Analysis: Calculated for $C_{15}H_{27}N_3O_4$: C, 57.49; H, 8.68; N, 13.41 Found: C, 57.38; H, 8.63; N, 13.33

To a mixture of the above amine (0.7 g, 2.23 mmol) in dimethylformamide (13 mL) were added triethylamine (0.81 g, 8.01 mmol), S-methyl N,N'-bis-tert-butoxycarbonylisothiourea (714 mg, 2.46 mmol) and mercury chloride (665 mg, 2.46 mmol) and the mixture stirred at room temperature for 16 h. The reaction mixture was diluted with ethyl acetate (100 mL), filtered through Celite and the filtrate washed with water (2×100 mL) and brine (1×100 mL). The organic layer was dried (MgSO₄), filtered and the filtrate concentrated. The residue was passed through a column of silica gel (100 g) using ethyl acetate as an eluent. The desired fractions were combined and concentrated to give 0.7 g (56%) of a mixture of isomers. The mixture was recrystallized from ether-hexane thrice to give 0.16 g (13%) of methyl t-3β-{[(tert-butoxylcarbonylamino)(tert-tritoxycarbonylimino)methyl]amino}-c-4-[(diethylamino-carbonyl)(methylcarbonylamino)methyl]cyclopentan-r-carboxylate (isomer A at C-6 and C-1) as a white solid, mp 140° C.

Analysis: Calculated for $C_{26}H_{45}N_5O_8$: C, 56.20; H, 8.16; N, 12.60 Found: C, 55.50; H, 8.16; N, 12.48

A mixture of the above ester (0.14 g, 0.25 mmol) in tetrahydrofuran (5 mL) was stirred with sodium hydroxide (1 N, 1.5 mL) at room temperature for 4 h. The mixture was concentrated, the residue dissolved in water (2 mL), filtered through a plug of cotton and the filtrate acidified with acetic acid. The precipitate obtained was collected by filtration, washed with water and dried to give 0.11 g (81%) of the corresponding acid.

A mixture of the above acid (0.08 g, 0.15 mmol) in dichloromethane (5 mL) was stirred with trifluoroacetic acid (1.0 mL) for 16 h at room temperature. The reaction mixture was concentrated and the residue was washed with ether (2×20 mL). The residue was dissolved in methanol and ether added. The mixture was let stand in the refrigerator for 24 h. The solvent was decanted and the residue washed two times with ether and dried to give 0.06 g of the trifluoroacetic acid salt of the title compound as a white powder, mp >110° C. (dec).

Analysis: Calculated for $C_{15}H_{27}N_5O_4 \cdot CF_3COOH$: C, 44.83; H, 6.20; N, 15.38 Found: C, 44.71; H, 6.37; N, 14.77

Example 31

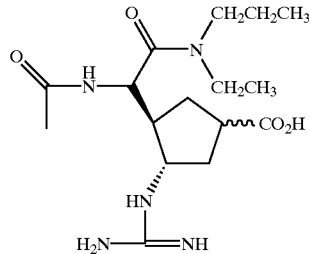

3β-{[(Amino)(imino)methyl]amino}-4α-{[(ethyl)(propyl)aminocarbonyl](methyl-carbonylamino)methyl}cyclopentancarboxylic acid (isomer A at C-6)

To a mixture of 2-{3β-{[(tert-butoxycarbonylamino)(tert-butoxycarbonyl-imino)methyl]amino}-4α-[(carboxy)(methylcarbonylamino)methyl]-1-cyclopentyl-idene}-1,3-dithiane (from Example 7) (0.5 g, 0.9 mmol) in tetrahydrofuran (15 mL) was added triethylamine (0.12 g, 1.15 mmol), and methyl chloroformate (0.11 g, 1.15 mmol) and stirred at room temperature for 1 h. To this mixture was added ethylpropylamine (0.32 g, 3.6 mmol) and stirred for 3 h at room temperature. The reaction mixture was diluted with ethyl acetate (70 mL) and washed with water (75 mL) and brine (75 mL). The organic layer was separated, dried (MgSO₄), filtered and concentrated. The residue was passed through a column of silica gel (50 g) using ethyl acetate-:hexane (1:1) mixture as an eluent to give 0.17 g (30%) of 2-{3β-{[(tert-butoxycarbonylamino)(tert-butoxycarbonylimino)methyl]amino}-4α-[(ethylpropylaminocarbonyl)(methylcarbonyl-amino)methyl]-1-cyclopentylidene}-1,3-dithiane (isomer A at C-6) as a white solid, mp 115–116° C.

Analysis: Calculated for $C_{29}H_{49}N_5O_6$: C, 55.48; H, 7.87; N, 11.15 Found: C, 55.60; H, 7.84; N, 11.23

A 0.24 g (43%) sample of isomer B at C-6 was also isolated as a white solid, mp 122–123° C.

Analysis: Calculated for $C_{29}H_{49}N_5O_6$: C, 55.48; H, 7.87; N, 11.15 Found: C, 55.57; H, 7.89; N, 11.21

A mixture of the above isomer A (0.14 g, 0.226 mmol) and hydrochloric acid in methanol (0.75 N, 6.0 mL) was stirred at room temperature for 24 h. The mixture was then neutralized with 1 N sodium hydroxide and 2 drops of additional 1 N sodium hydroxide added and mixture stirred for 2 h. After neutralization with 1 N hydrochloric acid, the mixture was concentrated, salts were removed by filtration and the filtrate concentrated. The residue was passed through a column of silica gel (20 g) using ethyl acetate: hexane (3:1) as an eluent to give 0.05 g (39%) of methyl 3β-{[(tert-butoxycarbonylamino)(tert-butoxycarbonylimino)methyl]amino}-4α-[(ethylpropyl-aminocarbonyl)(methylcarbonylamino)methyl]-1-cyclopentancarboxylate (isomer A at C-6).

A mixture of the above ester (0.04 g, 0.07 mmol) and sodium hydroxide (1 N, 0.5 mL) was stirred at room temperature for 2 h. The reaction mixture was diluted with water (2 mL) and filtered through a cotton plug. The filtrate was neutralized with acetic acid. The precipitate which formed was collected by filtration, washed with water and dried to give 0.03 g (77%) of 3β-{[(tert-butoxycarbonylamino)(tert-butoxy-carbonylimino)methyl]amino}-4α-[(ethylpropylaminocarbonyl)(methylcarbonylamino)-methyl]cyclopentancarboxylic acid (isomer A at C-6).

A mixture of the above acid (0.012 g, 0.02 mmol) in dichloromethane (2 mL) was stirred with trifluoroacetic acid (0.2 mL) for 24 h at room temperature. The reaction mixture was concentrated and evaporated twice with dichloromethane to give the title compound as residue [MS (ES+): 356.4].

Example 32

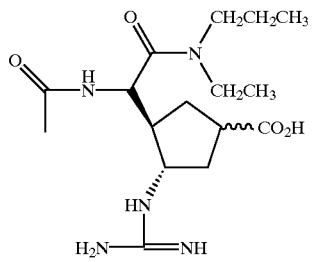

3β-{[(Amino)(imino)methyl]amino}-4α-{[(ethyl)(propyl)aminocarbonyl](methyl-carbonylamino)methyl}cyclopentancarboxylic acid (isomer B at C-6)

A mixture of 2-{3β-{[(tert-butoxycarbonylamino)(tert-butoxycarbonyl-imino)methyl]amino}-4α-[(ethylpropylaminocarbonyl)(methylcarbonylamino)methyl]-1-cyclopentylidene}-1,3-dithiane (isomer B at C-6) (from Example 31) (0.18 g, 0.288 mmol) and hydrochloric acid in methanol (0.75 N, 6.0 mL) was stirred at room temperature for 24 h. The mixture was then neutralized with 1 N sodium hydroxide and 2 drops of additional 1 N sodium hydroxide added and the mixture stirred for 2 h. After neutralization with 1 N hydrochloric acid, the mixture was concentrated, salts were removed by filtration and the filtrate concentrated. The residue was passed through a column of silica gel (20 g) using ethyl acetate:hexane (3:1) as an eluent to give 0.06 g (36%) of methyl 3β-{[(tert-butoxycarbonylamino)(tert-butoxycarbonylimino)methyl]-amino}-4α-[(ethylpropylaminocarbonyl)(methylcarbonylamino)methyl]-1-cyclopentancarboxylate (isomer B at C-6).

A mixture of the above ester (0.06 g, 0.1 mmol) and sodium hydroxide (1 N, 0.5 mL) were stirred at room temperature for 2 h. The reaction mixture was diluted with water (2 mL) and filtered through a cotton plug. The filtrate was neutralized with acetic acid. The precipitate which formed was collected by filtration, washed with water and dried to give 0.045 g (80%) of 3β-{[(tert-butoxycarbonylamino)(tert-butoxy-carbonylimino)methyl]amino}-4α-[(ethylpropylaminocarbonyl)(methylcarbonylamino)-methyl]cyclopentancarboxylic acid (isomer A at C-6).

A mixture of the above acid (0.03 g, 0.05 mmol) in dichloromethane (2 mL) was stirred with trifluoroacetic acid (0.3 mL) for 24 h at room temperature. The reaction mixture was concentrated and evaporated twice with dichloromethane to give the title compound as residue [MS (ES+): 356.3 (100%)]

Examples 33–64

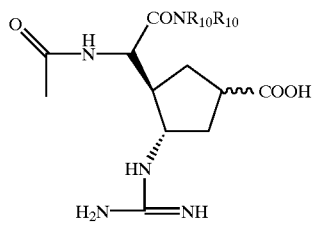

General preparation of amides through parallel synthesis resulting in a mixture of isomers at C-1 and C-6.

To a mixture of 2-{3β-{[(tert-butoxycarbonylamino)(tert-butoxycarbonyl-imino)methyl]amino}-4α-[(carboxy)(methylcarbonylamino)methyl]-1-cyclopentyl-idene}-1,3-dithiane (from Example 7) (0.093 g, 0.16 mmol) in tetrahydrofuran (3.0 mL) was added triethylamine (35 μL, 0.25 mmol), and methyl chloroformate (20 μL, 0.25 mmol) and the mixture stirred at room temperature for 1 h. To this mixture was added the appropriate amine (0.8 mmol) and stirred for 16 h. The reaction mixture was diluted with ethyl acetate (20 mL) and washed with water (20 mL). The organic layer was separated, dried ($MgSO_4$), filtered and concentrated.

To this residue was added methanolic hydrochloric acid (4.5 mL, 0.75 N), stirred for 20 h at room temperature, made basic with sodium hydroxide and stirred for 4 h at room temperature. The mixture was again neutralized with HCl, concentrated to dryness and stirred with dichloromethane (5 mL) and trifluoroacetic acid (1 mL) for 4 h. The mixture was then concentrated to dryness and the residue characterized by mass spectrum analysis. By this method the following amides were isolated:

| Example | $R_{10}$ | $R_{10}$ | MS (ES+) |
| --- | --- | --- | --- |
| 33 | $CH_3$ | $(CH_2)_2Ph$ | 404.4 |
| 34 | $CH_3$ | $(CH_2)_3CH_3$ | 356.4 |
| 35 | $C_2H_5$ | $CH_2Ph$ | 404.4 |

-continued

| Example | R$_{10}$ | R$_{10}$ | MS (ES+) |
|---|---|---|---|
| 36 | CH$_3$ | (CH$_2$)$_5$CH$_3$ | 384.4 |
| 37 |  | pyrrolidino | 340.5 |
| 38 | (CH$_2$)$_2$CH$_3$ | CH$_2$-cyclopropyl | 382.4 |
| 39 | C$_2$H$_5$ | (CH$_2$)$_2$OH | 358.5 |
| 40 | C$_2$H$_5$ | (CH$_2$)$_3$CH$_3$ | 370.4 |
| 41 | CH$_3$ | (CH$_2$)$_2$OH | 344.2 |
| 42 |  | azetidino | 326.4 |
| 43 | H | CH(CH$_3$)(C$_2$H$_5$) | 342.3 |
| 44 | C$_2$H$_5$ | CH$_2$C(CH$_3$)=CH$_2$ | 368.4 |
| 45 | CH$_3$ | CH$_2$CH=CH$_2$ | 340.3 |
| 46 | CH$_3$ | CH(CH$_3$)$_2$ | 342.3 |
| 47 | CH$_3$ | (CH$_2$)$_2$CH$_3$ | 342.3 |
| 48 | C$_2$H$_5$ | (CH$_2$)$_2$CH$_3$ | 356.4 |
| 49 | H | CH(C$_2$H$_5$)$_2$ | 356.3 |
| 50 | C$_2$H$_5$ | C$_2$H$_5$ | 342.3 |
| 51 | H | CH(CH$_3$)$_2$ | 328.4 |
| 52 | H | CH(CH$_3$)(CH$_2$CH$_2$Ph) | 418.5 |
| 53 | H | CH(CH$_3$)[CH$_2$CH(CH$_3$)$_2$] | 370.4 |
| 54 | H | CH(CH$_2$OH)(C$_3$H$_7$) | 372.3 |
| 55 | H | CH(CH$_3$)(C$_4$H$_9$) | 370.5 |
| 56 | H | CH(CH$_3$)[(CH$_2$)$_2$C(OH)(CH$_3$)$_2$] | 414.6 |
| 57 | H | CH(CH$_3$)(CH$_2$OCH$_3$) | 358.0 |
| 58 | H | CH(C$_2$H$_5$)(CH$_2$OCH$_3$) | 372.0 |
| 59 | H | CH(CH$_3$)(C$_3$H$_7$) | 356.0 |
| 60 | H | CH(C$_2$H$_5$)(C$_3$H$_7$) | 384.0 |
| 61 |  | piperidine | 354.0 |
| 62 |  | 3,4-didehydropiperidino | 352.0 |
| 63 |  | 2-methylpiperidino | 368.0 |
| 64 |  | 2-ethylpiperidino | 382.0 |

Example 65

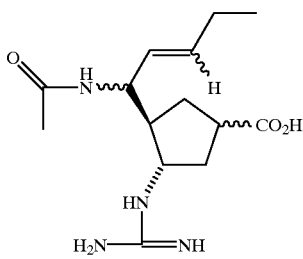

3β-{[(Amino)(imino)methyl]amino}-4α-[1-(1-methylcarbonylamino)pent-2-enyl]cyclo-pentancarboxylic acid To a suspension of propyltriphenylphosphonium bromide (0.28 g, 0.73 mmol) in tetrahydrofuran (10 mL) at −78° C. was added sodium bis(trimethylsilyl)amide (1 M/tetrahydrofuran, 0.73 mL, 0.73 mmol) dropwise. After stirring for 10 min, the reaction mixture was allowed to warm to 0° C., stirred for 20 min, and cooled to −78° C. To this mixture was added 2-{3β-(tert-butoxycarbonylamino)-4α-[(formyl)(methylcarbonyl-amino)methyl]cyclopentylidene}-1,3-dithiane (0.097 g, 0.24 mmol) (from Example 10) in tetrahydrofuran (6 mL) and the reaction mixture was stirred for 1 h. Water (10 mL) was added and the layers were separated. The aqueous layer was extracted with ether (4×10 mL). The combined organic extracts were washed with brine, dried (MgSO$_4$), filtered through Celite, and concentrated in vacuo to give 0.16 g of crude. Purification by radial PLC (SiO$_2$, 50–75% ethyl acetate/hexanes) furnished 0.093 g (91%) of 2-{3β-(tert-butoxycarbonylamino)-4α-[1-(1-methylcarbonylamino) pent-2-enyl]cyclopentyl-idene}-1,3-dithiane as a white solid, mp 175–177° C.

Analysis: Calculated for C$_{21}$H$_{34}$N$_2$O$_3$S$_2$: C, 59.12; H, 8.03; N, 6.57 Found: C, 59.21; H, 8.04; N, 6.51

To a stirred solution of the above solid (0.64 g, 1.5 mmol) in methanol (44 mL) at room temperature was added 6 N HCl (3.8 mL, 22.8 mmol) and the reaction mixture was stirred for 25 h. The reaction mixture was cooled to 0° C. and sodium hydroxide (1.0 g, 25 mmol) was added. After stirring for 50 min at room temperature, the reaction mixture was quenched with glacial acetic acid (0.41 mL, 7.0 mmol) and concentrated in vacuo to furnish a residue. To this residue was added ethyl acetate (15 mL) and water (10 mL) and the layers were separated. The aqueous layer was extracted with ethyl acetate (4×15 mL). The combined organic extracts were extracts were washed with brine, dried (MgSO$_4$), filtered through Celite, and concentrated in vacuo to give 0.37 g (66%) of methyl 3β-(tert-butoxycarbonylamino)-4α-[1-(1-methylcarbonylamino)pent-2-enyl]-cyclopentancarbonylate.

A mixture of the above ester (0.28 g, 0.66 mmol) and trifluoroacetic acid (1.0 mL, 13.0 mmol) in dichloromethane was stirred at room temperature for 5.5 h. The reaction mixture was concentrated in vacuo to give 0.29 g (100%) of methyl 3β-amino-4α-[1-(1-methylcarbonylamino)pent-2-enyl]cyclopentancarboxylate.

To the mixture of the above amine (0.29 g, 0.66 mmol) in dimethylformamide (7 mL) was added N,N'-bis-tert-butoxycarbonyl-S-methyl isothiourea (0.24 g, 0.81 mmol), triethylamine (3.0 mL, 21.5 mmol), and mercuric chloride (0.22 g, 0.81 mmol). The reaction mixture was stirred at room temperature overnight. To this mixture was added ethyl acetate (20 mL) and water (15 mL) and the layers were separated. The organic layer was washed with brine, dried (MgSO$_4$), filtered through Celite, and concentrated in vacuo to provide 0.35 g of crude. Purification by radial PLC (SiO$_2$, 50–75% ethyl acetate/hexanes) gave 0.214 g (64%) of methyl 3β-{[(tert-butoxycarbonylamino)(tert-butoxycarbonylimino)methyl]amino}-4α-[1-(1-methylcarbonylamino)pent-2-enyl]cyclo-pentancarboxylate.

To a mixture of the above ester (0.116 g, 0.23 mmol) in tetrahydrofuran (3.5 mL) and water (2 mL) at room temperature was added 1 N NaOH (0.6 mL, 0.6 mmol). The reaction mixture was stirred for 2 h and concentrated in vacuo. The concentrate was acidified with glacial acetic acid and extracted with ethyl acetate (4×10 mL). The combined organic extracts were washed with brine, dried (MgSO$_4$), filtered through Celite, and concentrated in vacuo to afford 0.114 g (100%) of 3β-{[(tert-butoxycarbonylamino)(tert-butoxycarbonylimino)methyl]amino}-4α-[1-(1-methylcarbonylamino)pent-2-enyl]cyclopentancarboxylic acid.

A mixture of the above acid (0.114 g, 0.23 mmol) and trifluoroacetic acid (0.35 mL, 4.5 mmol) in dichloromethane (8 mL) was stirred at room temperature for 24 h. The reaction mixture was concentrated in vacuo to give crude. Trituration with ether afforded 0.064 g (59%) of the title compound as a tan solid, mp 62–64° C.

Analysis: Calculated for C$_{14}$H$_{24}$N$_4$O$_3$·1.5CF$_3$CO$_2$H C, 43.68; H, 5.50; N, 11.99 Found: C, 43.48; H, 5.84; N, 12.03

Example 66

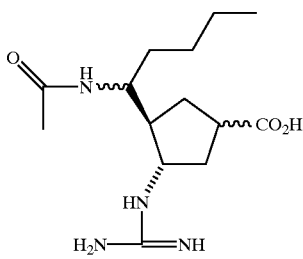

3β-{[(Amino)(imino)methyl]amino}-4α-[1-(1-methylcarbonylamino)pentyl]cyclo-pentancarboxylic acid A mixture of Example 65 (0.021 g, 0.045 mmol) and platinum oxide (0.05 g) in ethanol (6 mL) was hydrogenated at 50 psi overnight. The reaction mixture was filtered through Celite and the filtrate was concentrated in vacuo to give crude. Trituration with ether afforded 0.020 g (95%) of the title compound as a tan solid, mp 65–67° C.

Analysis: Calculated for $C_{14}H_{26}N_4O_3 \cdot 1.5CF_3CO_2H$ C, 43.50; H, 5.91; N, 11.95 Found: C, 43.63; H, 6.16; N, 12.20

Biochemistry

The in vitro assay is based on the method reported by von Itzstein et al. (EP Application 92309634.6). The neuraminidase from the H1N9 strain of influenza was obtained by the method described by Laver et al. Virology 1984, 137, p. 314–323. Values for the $IC_{50}$ were measured via a spectrofluorometric technique which uses the fluorogenic substrate 2'-(4-methylumbelliferyl)-α-D-acetylneuramic acid. This substrate is cleaved by neuraminidase to yield a fluorescent product which can be quantified. The assay mixture contains inhibitors at various concentrations (four to six points) and enzyme in 32.5 mM MES [(2-(N-morpholino) ethanesulfonic acid] buffer, 4 mM $CaCl_2$ at pH=6.5 (total volume=80 μL). The reaction is started by the addition of 20 μL of the substrate to a final concentration of 75 μM. After 10 min at 37° C., 2.4 mL of 0.1M glycine/NaOH (pH=10.2) is added to 0.1 mL of the reaction mixture to terminate the reaction. A blank is run with the same substrate solution with no enzyme. Fluorescence is read using an Aminco-Bowman fluorescence spectrophotometer (excitation: 360 nm and emission: 450 nm) and substrate blanks were subtracted from the readings. The $IC_{50}$ is calculated by plotting percent inhibition versus the inhibitor concentration, and determination of each point is performed in duplicate.

Crystallography

Complexes between neuraminidase and inhibitor molecules were prepared by transferring H1N9 neuraminidase crystals into 2 mL of the phosphate buffer solution in which the inhibitor has been dissolved. The concentration of the inhibitor compound was adjusted to be 2 mM. The crystal was allowed to equilibrate in the buffer solution for about one day and then removed from the solution and mounted in a glass capillary for X-ray diffraction data collection. All X-ray intensity measurements were recorded with a Siemens X-100 multiwire area detector on a Rigaku RU-300 rotating anode generator operating at 100 mA and 50 kV and a copper anode. The crystal to detector distance was 160 mm and the detector was offset to collect 2.4 Å data. Intensity data were measured on 0.1 oscillation frames at 240 s of exposure per frame. Each crystal yielded 600–700 frames of data before radiation damage to the crystals prevented further data collection.

The intensity data were processed using the XENGEN package of programs. The integrated intensities were scaled and merged to produce a final data set containing only unique reflections. The final data sets were complete to 2.5 Å resolution. All refinement was carried out using the program XPLOR. The starting model for refinement was the 2.0 Å refined native N9 structure. Difference Fourier maps to 2.5 Å were calculated using the calculated phases from the refined model. Analysis of the electron density maps was performed on a Silicon Graphics Indigo Extreme 2 computer graphics workstation using the graphics program QUANTA. Idealized models for the inhibitor molecules were manually fitted to the difference electron density. These inhibitor models were later included in the XPLOR refinement.

Biological Data

| Example No. | Inhibition of H1N9 Influenza Neuraminidase $IC_{50}$ (μm) |
|---|---|
| 3 | 115 |
| 5 | 280 |
| 6 | 90 |
| 7 | 3800 |
| 9 | 600 |
| 10 | 600 |
| 12 | 7.5 |
| 13 | 4.3 |
| 14 | 40 |
| 15 | 50 |
| 16 | 70 |
| 17 | 2000 |
| 19 | 16 |
| 20 | 8 |
| 21 | 1.6 |
| 23 | 0.47 |
| 24 | 4.9 |
| 25 | 2300 |
| 26 | 0.041 |

Dosage and Formulation

The antiviral compounds of this invention can be administered as treatment for viral infections by any means that produces contact of the active agent's site of action with the viral neuraminidase in the body of a human, mammal, bird, or other animal. They can be administered by an conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the preferred dose being 0.1 to about 30 mg/kg.

Dosage forms (compositions suitable for administration) contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation. Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company, a standard reference text in this field.

Useful pharmaceutical dosage forms for administration of the compounds according to the present invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mu of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Moreover, the compounds of the present invention can be administered in the form of nose drops or a nasal inhaler.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

What is claimed is:
1. A compound represented by the formula

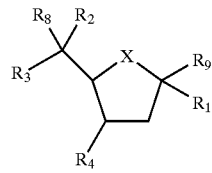

1 wherein
X is $CH_2$, O or S
$R_1$ is H, OH, $NH_2$, or $OR_{11}$;
$R_9$ is $CO_2H$, $SO_3H$, $PO_3H_2$, $NO_2$, esters thereof, or salts thereof;

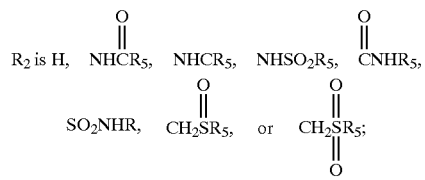

each of $R_3$ and $R_8$ individually is H, $(CH_2)_n CO_2 R_{10}$, $(CH_2)_m OR_{10}$, $CON(R_{10})_m$, $(CH_2)_n N(R_{10})_m$, $CH(R_{10})_m$, $(CH_2)_n (R_{10})_m$, $CH_2 CH(OR_{10})CH_2 OR_{10}$, $CH(OR_{10})CH(OR_{10})CH_2 OR_{10}$, $CH_2 OR_{10}$, $CH(OR_{10})CH_2 NHR_{10}$, $CH_2 CH(OR_{10})CH_2 NHR_{10}$, $CH(OR_{10})CH(OR_{10})CH_2 NHR_{10}$, or $NR_{10}C(=NR_{10})N(R_{10})_m$;
provided that at least one of $R_2$, $R_3$ and $R_8$ is other than H;
$R_4$ is $(CH_2)_n OH$, $(CH_2)_n NH_2$, $(CH_2)_n C(=NH)NH_2$, $(CH_2)_n NHC(=NR_7)NH_2$, $(CH_2)_n CN$ or $(CH_2)_n N_3$;
$R_5$ is H, lower alkyl, branched chain alkyl, cyclic alkyl or $CF_3$;
$R_7$ is H, OH, CN, $NH_2$ or $NO_2$;
$R_{10}$ is H, lower alkyl, lower alkylene, branched alkyl, cyclic alkyl, substituted cyclic alkyl, $(CH_2)_n$ aromatic, $(CH_2)_n$-substituted aromatic, and when m is 2 both $R_{10}$ groups can also be interconnected to form an N-heterocyclic ring;
$R_{11}$ is lower alkyl, branched alkyl, or $(CH_2)_m$ aromatic;
m is 1 or 2;
n is 0–4;
and further provided that when x is O or S, $R_3$ and $R_8$ is other than $CH(OR_{10})CH(OR_{10})CH_2 OR_{10}$;
and pharmaceutically acceptable salts thereof.

2. The compound of claim 1, wherein said lower alkyl group of $R_5$, $R_{10}$ and $R_{11}$ contains 1 to about 8 carbon atoms; and said lower alkylene group contains 2 to about 8 carbon atoms.

3. The compound of claim 1, wherein said lower alkyl group of $R_5$, $R_{10}$ and $R_{11}$ contains 1 to about 3 carbon atoms; and said lower alkylene group contains 2 to 3 carbon atoms.

4. The compound of claim 1, wherein said alkyl group of $R_5$, $R_{10}$ and $R_{11}$ is selected from the group consisting of methyl, ethyl, propyl, isopropyl, t-butyl, cyclopentyl, and cyclohexyl, the aromatic group is selected from the group consisting of phenyl and alkyl substituted aromatic groups; the substituted cycloalkyl group contains 3–8 carbon atoms in the ring and are substituted with 1 or 2 alkyl groups having 1–6 carbon atoms, hydroxy group or both; and the alkylene group is selected from the group consisting of vinyl, 1-propenyl, allyl, isopropenyl, 2-methyl-2-propenyl and cyclopentenyl.

5. The compound of claim 1, wherein said salt is from an acid selected from the group consisting of hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic, trifluoroacetic and benzenesulphonic acid.

6. The compound of claim 1, wherein said salt is a sodium or ammonium salt.

7. The compound of claim 1 being cis-3-[(methylcarbonylamino)methyl]cyclopentanecarboxylic acid or salt thereof.

8. The compound of claim 1 being trans-3-amino-c-4-(methylcarbonylamino)methyl-r-cyclopentanecarboxylic acid or salt thereof.

9. The compound of claim 1 being trans-3-{[(amino)(imino)methyl]amino}-c-4-[(methylcarbonylamino)methyl]cyclopentan-r-carboxylic acid or salt thereof.

10. The compound of claim 1 being 4β-{[(amino)(imino)methyl]amino}-3α-[(2-hydroxy-1-methylcarbonylamino)ethyl]-1-cyclopentanecarboxylic acid or salt thereof.

11. The compound of claim 1 being sodium 3β-{[amino)(imino)methyl]amino}-4α-[(2-hydroxy)(1-methylcarbonylamino)ethyl]cyclopentan-r-carboxylate.

12. The compound of claim 1 being trans-3-amino-trans-1-hydroxy-cis-4[(hydroxymethyl)(methylcarbonylamino)methyl]cyclopentan-r-carboxylic acid or salt thereof.

13. The compound of claim 1 being trans-3-{[(amino)(imino)methyl]amino}-trans-1-hydroxy-cis-4-[(2-hydroxymethyl)(1-methylcarbonylamino)ethyl]cyclopentan-r-carboxylic acid or salt thereof.

14. The compound of claim 1 being 3β-amino-4α-[(1-methylcarbonylamino)(2,3,4-trihydroxy)butyl]cyclopentancarboxylic acid or salt thereof.

15. The compound of claim 1 being 3β-{[(amino)(imino)methyl]amino}-4α-[(1-methylcarbonylamino)(2,3,4-trihydroxy)butyl]-cyclopentancarboxylic acid or salt thereof.

16. The compound of claim 1 being cis-3-{[(amino)(imino)methyl]amino}-trans-1-hydroxy-trans-4-[(1-methylcarbonylamino)(2-trifluoromethyl-carbonyloxy)ethyl]cyclopentan-r-carboxylic acid or salt thereof.

17. The compound of claim 1 being t-3-amino-c-4-[(1-methylcarbonylamino)(2-phenylmethoxy)ethyl]-t-1-hydroxycyclopentan-r-carboxylic acid or salt thereof.

18. The compound of claim 1 being c-3-{[(amino(imino)methyl]amino}-t-1-hydroxy-t-4-{(methylcarbonylamino){[(methyl)-(methoxy)amino]carbonyl}methyl}cyclopentan-r-carboxylic acid or salt thereof.

19. The compound of claim 1 being t-3-{[(amino)(imino)methyl]amino}-c-4-[(diethylaminocarbonyl)(methylcarbonylamino)methyl]-t-1-hydroxycyclopentan-r-carboxylic acid or salt thereof.

20. The compound of claim 1 being t-3-amino-c-4-[(di-n-propylaminocarbonyl)(methylcarbonylamino)methyl]-t-1-hydroxy-cyclopentan-r-carboxylic acid or salt thereof.

21. The compound of claim 1 being t-3-{[(amino)(imino)methyl]amino}-c-4-[di-n-propylaminocarbonyl)(methylcarbonylamino)methyl]-t-hydroxycyclopentan-r-carboxylic acid or salt thereof.

22. The compound of claim 1 being c-3-{[(amino)(imino)methyl]amino}-t-4-[(di-n-propylaminocarbonyl)(methylcarbonylamino)methyl]-t-1-hydroxycyclopentan-r-carboxylic acid or salt thereof.

23. The compound of claim 1 being 3β-{[(amino)(imino)methyl]amino}-4α-[(di-n-propylaminocarbonyl)(methylcarbonylamino)-methyl]cyclopentancarboxylic acid or salt thereof.

24. The compound of claim 1 being 3β-{[(amino)(imino)methyl]amino}-4α-[(methylcarbonylamino)(3-pentylaminocarbonyl)methyl]cyclopentancarboxylic acid or salt thereof.

25. The compound of claim 1 being 3β-{[Amino)(imino)methyl]amino}-4α-[(diethylaminocarbonyl)methylcarbonylamino)-methyl]cyclopentancarboxylic acid or salt thereof.

26. The compound of claim 1 being 3β-{[(Amino)(imino)methyl]amino}-4α-{[(ethyl)(propyl)aminocarbonyl](methyl-carbonylamino)methyl}cyclopentancarboxylic acid or salt thereof.

27. The compound of claim 1 represented by the formula:

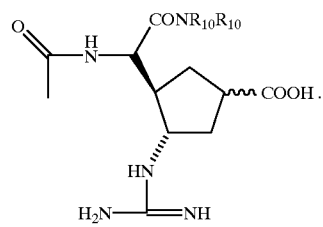

28. The compound of claim 1 being 3β-{[(Amino)(imino)methyl]amino}-4α-[1-(1-methylcarbonylamino)pent-2-enyl]cyclo-pentancarboxylic acid or salt thereof.

29. The compound of claim 1 being 3β-{[(Amino)(imino)methyl]amino}-4α-[1-(1-methylcarbonylamino)pentyl]cyclopentan-carboxylic acid or salt thereof.

30. A composition for inhibiting influenza virus neruaminidase, comprising:

a pharmaceutically acceptable carrier and an amount effective for inhibiting influenza virus neruaminidase of a compound according to claim 1.

31. A method for inhibiting influenza virus neruaminidase, comprising the step of:

administering to a patient in need thereof a composition comprising a pharmaceutically acceptable carrier and an amount effective for inhibiting influenza virus neruaminidase of a compound according to claim 1.

* * * * *